(12) United States Patent
Yan et al.

(10) Patent No.: US 6,638,738 B2
(45) Date of Patent: Oct. 28, 2003

(54) ISOLATED HUMAN LIPASE PROTEINS, NUCLEIC ACID MOLECULES ENCODING HUMAN LIPASE PROTEINS, AND USES THEREOF

(75) Inventors: Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/811,825

(22) Filed: Mar. 20, 2001

(65) Prior Publication Data
US 2002/0144297 A1 Oct. 3, 2002

(51) Int. Cl.[7] .................................. C12P 21/06
(52) U.S. Cl. .................... 435/69.1; 536/23.2; 536/23.5; 424/93.2; 435/320.1; 435/325; 435/455; 435/243; 435/348; 435/353; 435/354; 435/410; 435/358; 435/254.11; 435/252.3

(58) Field of Search .............................. 435/320.1, 69.1, 435/455, 440, 325, 348, 353, 354, 243, 410, 358, 254.11, 252.3; 536/23.1, 27.2, 23.5

(56) References Cited
FOREIGN PATENT DOCUMENTS
WO    WO 200077239    *    3/2001

* cited by examiner

Primary Examiner—Scott D. Priebe
Assistant Examiner—Brian Whiteman
(74) Attorney, Agent, or Firm—Celera Genomics; Lin Sun-Hoffman

(57) ABSTRACT

The present invention provides amino acid sequences of peptides that are encoded by genes within the human genome, the lipase peptides of the present invention. The present invention specifically provides isolated peptide and nucleic acid molecules, methods of identifying orthologs and paralogs of the lipase peptides, and methods of identifying modulators of the lipase peptides.

16 Claims, 14 Drawing Sheets

```
   1 TATATGGAGC TAAAACTGCT CTTCAGAGAT GTCCTACGTT GGGCTGAGAT
  51 GACCAGGCCT TTAGACCGCA AACAGAGTGA AATCATCCAA CATCAAGGCT
 101 ATCCCTGTGA GGAATATGAA GTCGCAACTG AAGATGGGTA TATCCTTTCT
 151 GTTAACAGGA TTCCTCGAGG CCTAGTGCAA CCTAAGAAGA CAGGTTCCAG
 201 GCCTGTGGTG TTACTGCAGC ATGGCCTAGT TGGAGGTGCT AGCAACTGGA
 251 TTTCCAACCT GCCCAACAAT AGCCTGGGCT TCATTCTGGC AGATGCTGGT
 301 TTTGACGTGT GGATGGGGAA CAGCAGGGGA AACGCCTGGT CTCGAAAACA
 351 CAAGACACTC TCCATAGACC AAGATGAGTT CTGGGCTTTC AGTTATGATG
 401 AGATGGCTAG GTTTGACCTT CCTGCAGTGA TAAACTTTAT TTTGCAGAAA
 451 ACGGGCCAGG AAAAGATCTA TTATGTCGGC TATTCACAGG GCACCACCAT
 501 GGGCTTTATT GCATTTTCCA CCATGCCAGA GCTGGCTCAG AAAATCAAAA
 551 TGTATTTTGC TTTAGCACCC ATAGCCACTG TTAAGCATGC AAAAAGCCCC
 601 GGGACCAAAT TTTTGTTGCT GCCAGATATG ATGATCAAGG GATTGTTTGG
 651 CAAAAAAGAA TTTCTGTATC AGACCAGATT TCTCAGACAA CTTGTTATTT
 701 ACCTTTGTGG CCAGGTGATT CTTGATCAGA TTTGTAGTAA TATCATGTTA
 751 CTTCTGGGTG GATTCAACAC CAACAATGA GAGCCAAGTGT
 801 ATATGCTGCC CACACTCTTG CTGGAACATC TGTGCAAAAT ATTCTACACT
 851 GGAGCCAGGC AGTGAATTCT GGTGAACTCC GGGCATTTGA CTGGGGGAGT
 901 GAGACCAAAA ATCTGGAAAA ATGCAATCAG CCAACTCCTG TAAGGTACAG
 951 AGTCAGAGAT ATGACGGTCC CTACAGCAAT GTGGACAGGA GGTCAGGACT
1001 GGCTTTCAAA TCCAGAAGAC GTGAAAATGC TGCTCTCTGA GGTGACCAAC
1051 CTCATCTACC ATAAGAATAT TCCTGAATGG GCTCACGTGG ATTTCATCTG
1101 GGGTTTGGAT GCTCCTCACC GTATGTACAA TGAAATCATC CATCTGATGC
1151 AGCAGGAGGA GACCAACCTT TCCCAGGGAC GGTGTGAGGC CGTATTGTGA
1201 ATAAAG
(SEQ ID NO: 1)

FEATURES:
5'UTR:        1 - 3
Start Codon:  4
Stop Codon:   1198
3'UTR:        1201

Homologous proteins:
Top 10 BLAST Hits:
```

|  | Score (bits) | E Value |
|---|---|---|
| Sequences producing significant alignments: |  |  |
| CRA\|118000039469997 /dataset=FastAlert /length=390 /altid=Derwe... | 779 | 0.0 |
| CRA\|118000039469993 /dataset=FastAlert /length=423 /altid=Derwe... | 779 | 0.0 |
| CRA\|1000686000121 /dataset=FastAlert /length=399 /altid=Derwent... | 492 | e-139 |
| CRA\|1000686016033 /dataset=FastAlert /length=398 /altid=Derwent... | 426 | e-120 |
| CRA\|118000039469999 /dataset=FastAlert /length=221 /altid=Derwe... | 425 | e-119 |
| CRA\|118000039470003 /dataset=FastAlert /length=144 /altid=Derwe... | 309 | 1e-84 |
| CRA\|108000023796376 /dataset=FastAlert /length=233 /altid=Derwe... | 258 | 3e-69 |
| CRA\|118000039470001 /dataset=FastAlert /length=25 /altid=Derwen... | 54 | 9e-08 |

EST:

|  | Score (bits) | E Value |
|---|---|---|
| Sequences producing significant alignments: |  |  |
| gi\|3145270 /dataset=dbest /taxon=9606 ... | 184 | 4e-44 |
| gi\|2278431 /dataset=dbest /taxon=9606 ... | 180 | 6e-43 |
| gi\|13331316 /dataset=dbest /taxon=96... | 145 | 3e-32 |
| gi\|12880079 /dataset=dbest /taxon=960... | 145 | 3e-32 |
| gi\|12877067 /dataset=dbest /taxon=960... | 145 | 3e-32 |
| gi\|12872283 /dataset=dbest /taxon=960... | 145 | 3e-32 |
| gi\|10996401 /dataset=dbest /taxon=96... | 145 | 3e-32 |
| gi\|10950737 /dataset=dbest /taxon=96... | 145 | 3e-32 |
| gi\|10353116 /dataset=dbest /taxon=960... | 145 | 3e-32 |
| gi\|12951723 /dataset=dbest /taxon=960... | 137 | 8e-30 |

FIGURE 1A

EXPRESSION INFORMATION FOR MODULATORY USE:
gi|3145270   Colon tumor
gi|2278431   Colon
gi|13331316  Kidney renal cell adenocarcinoma
gi|12880079  Placenta
gi|12877067  Placenta
gi|12872283  Placenta
gi|10996401  Placenta
gi|10950737  Teratocarcinoma
gi|10353116  Skin melanotic melanom
gi|12951723  B cell from Burkitt's lymphoma Tissue Expression:
Library of Mixed tissues (Brain, Heart, Kidney, Lung, Spleen, Testis, Leukocyte)

FIGURE 1B

```
  1 MELKLLFRDV LRWAEMTRPL DRKQSEIIQH QGYPCEEYEV ATEDGYILSV
 51 NRIPRGLVQP KKTGSRPVVL LQHGLVGGAS NWISNLPNNS LGFILADAGF
101 DVWMGNSRGN AWSRKHKTLS IDQDEFWAFS YDEMARFDLP AVINFILQKT
151 GQEKIYYVGY SQGTTMGFIA FSTMPELAQK IKMYFALAPI ATVKHAKSPG
201 TKFLLLPDMM IKGLFGKKEF LYQTRFLRQL VIYLCGQVIL DQICSNIMLL
251 LGGFNTNNMN MSRASVYAAH TLAGTSVQNI LHWSQAVNSG ELRAFDWGSE
301 TKNLEKCNQP TPVRYRVRDM TVPTAMWTGG QDWLSNPEDV KMLLSEVTNL
351 IYHKNIPEWA HVDFIWGLDA PHRMYNEIIH LMQQEETNLS QGRCEAVL
    (SEQ ID NO:2)
```

FEATURES:
Functional domains and key regions:
[1] PDOC00001 PS00001 ASN_GLYCOSYLATION
N-glycosylation site Number of matches: 3
    1    88-91   NNSL
    2   260-263  NMSR
    3   388-391  NLSQ

---

[2] PDOC00004 PS00004 CAMP_PHOSPHO_SITE
cAMP- and cGMP-dependent protein kinase phosphorylation site 22-25   RKQS

---

[3] PDOC00005 PS00005 PKC_PHOSPHO_SITE
Protein kinase C phosphorylation site

Number of matches: 2
    1   113-115  SRK
    2   192-194  TVK

---

[4] PDOC00006 PS00006 CK2_PHOSPHO_SITE
Casein kinase II phosphorylation site

Number of matches: 4
    1   130-133  SYDE
    2   150-153  TGQE
    3   173-176  TMPE
    4   335-338  SNPE

---

[5] PDOC00007 PS00007 TYR_PHOSPHO_SITE
Tyrosine kinase phosphorylation site 149-157  KTGQEKIYY

---

[6] PDOC00008 PS00008 MYRISTYL
N-myristoylation site

Number of matches: 6
    1    74-79   GLVGGA
    2    77-82   GGASNW
    3   105-110  GNSRGN
    4   109-114  GNAWSR
    5   163-168  GTTMGF
    6   252-257  GGFNTN

---

[7] PDOC00009 PS00009 AMIDATION
Amidation site 215-218  FGKK

---

[8] PDOC00110 PS00120 LIPASE_SER
Lipases, serine active site 155-164  IYYVGYSQGT Membrane spanning structure and domains:
Helix Begin  End   Score  Certainty
    1   155  175   1.310  Certain

FIGURE 2A

BLAST Alignment to Top Hit:
>CRA|118000039469997 /dataset=FastAlert /length=390
        /altid=Derwent|WO200077239.49
        Length = 390

Score =  779 bits (1991), Expect = 0.0
 Identities = 374/374 (100%), Positives = 374/374 (100%)
 Frame = +1

Query:   73  SEIIQHQGYPCEEYEVATEDGYILSVNRIPRGLVQPKKTGSRPVVLLQHGLVGGASNWIS 252
             SEIIQHQGYPCEEYEVATEDGYILSVNRIPRGLVQPKKTGSRPVVLLQHGLVGGASNWIS
Sbjct:   17  SEIIQHQGYPCEEYEVATEDGYILSVNRIPRGLVQPKKTGSRPVVLLQHGLVGGASNWIS 76

Query:  253  NLPNNSLGFILADAGFDVWMGNSRGNAWSRKHKTLSIDQDEFWAFSYDEMARFDLPAVIN 432
             NLPNNSLGFILADAGFDVWMGNSRGNAWSRKHKTLSIDQDEFWAFSYDEMARFDLPAVIN
Sbjct:   77  NLPNNSLGFILADAGFDVWMGNSRGNAWSRKHKTLSIDQDEFWAFSYDEMARFDLPAVIN 136

Query:  433  FILQKTGQEKIYYVGYSQGTTMGFIAFSTMPELAQKIKMYFALAPIATVKHAKSPGTKFL 612
             FILQKTGQEKIYYVGYSQGTTMGFIAFSTMPELAQKIKMYFALAPIATVKHAKSPGTKFL
Sbjct:  137  FILQKTGQEKIYYVGYSQGTTMGFIAFSTMPELAQKIKMYFALAPIATVKHAKSPGTKFL 196

Query:  613  LLPDMMIKGLFGKKEFLYQTRFLRQLVIYLCGQVILDQICSNIMLLLGGFNTNNMNMSRA 792
             LLPDMMIKGLFGKKEFLYQTRFLRQLVIYLCGQVILDQICSNIMLLLGGFNTNNMNMSRA
Sbjct:  197  LLPDMMIKGLFGKKEFLYQTRFLRQLVIYLCGQVILDQICSNIMLLLGGFNTNNMNMSRA 256

Query:  793  SVYAAHTLAGTSVQNILHWSQAVNSGELRAFDWGSETKNLEKCNQPTPVRYRVRDMTVPT 972
             SVYAAHTLAGTSVQNILHWSQAVNSGELRAFDWGSETKNLEKCNQPTPVRYRVRDMTVPT
Sbjct:  257  SVYAAHTLAGTSVQNILHWSQAVNSGELRAFDWGSETKNLEKCNQPTPVRYRVRDMTVPT 316

Query:  973  AMWTGGQDWLSNPEDVKMLLSEVTNLIYHKNIPEWAHVDFIWGLDAPHRMYNEIIHLMQQ 1152
             AMWTGGQDWLSNPEDVKMLLSEVTNLIYHKNIPEWAHVDFIWGLDAPHRMYNEIIHLMQQ
Sbjct:  317  AMWTGGQDWLSNPEDVKMLLSEVTNLIYHKNIPEWAHVDFIWGLDAPHRMYNEIIHLMQQ 376

Query: 1153  EETNLSQGRCEAVL 1194
             EETNLSQGRCEAVL
Sbjct:  377  EETNLSQGRCEAVL 390 (SEQ ID NO:4)

Hmmer search results (Pfam):
Scores for sequence family classification (score includes all domains):
Model      Description                                    Score    E-value  N
--------   -----------                                    -----    -------  ---
PF00561    alpha/beta hydrolase fold                       53.9    1.6e-15  1
PF00067    Cytochrome P450                                  1.8        9.9  1

Parsed for domains:
Model      Domain  seq-f  seq-t    hmm-f  hmm-t      score    E-value
--------   ------  -----  -----    -----  -----      -----    -------
PF00067     1/1     207    226 ..   472    497 .]      1.8        9.9
PF00561     1/1     100    379 ..     1    233 []     53.9    1.6e-15

FIGURE 2B

```
   1 AGAGGAGAGG CTACCTCCAG ATGAGTAAGA CGATCATGTG CAATGTTCAT
  51 GTTCCAGAGA TTTATCTAAC AAACTCTCAG AAAATGGAAC TTTAACATGT
 101 ATTTTATACCG ATTTAAGACC CTTTCTACAG AAGCTTCCTT ATATGGGTTC
 151 AAAAACTGAG AGGAAATAGA AATATTCTGT ATCTGCATGG TGCTGAATAT
 201 CAGGTTTCTT TTGACTATTC AATGATTAGG TGGTTTGTCT AGGTAGTTAG
 251 CACATTGGTG TCAGTCCTCA GGAGTCATCC TTCTGGCCCT GAGACTGTCC
 301 CACTTGAATT CCTCTGGTTT GGAGGTGAGG GGAATCTCTG CAGTGGCAGA
 351 CAGAGATGAT CTTCCTGGGC CCCACCCACT GCGTGTACCC AGCACCTATA
 401 CACTACTGGG GCTTCAGGAG TCTGTAGACT AAAGCCCATT GAATTGGGCT
 451 CTGCCTTTAA GCAGCTATGC CTGGAAAAAA ACAAAGTAAA ATAGAAAATT
 501 CGTACGATTG GTGTAAATTC AACAAAATAG AATAAAAGTA GTTGCAAGTT
 551 TGAACTGGTT CTGAGGTAGG AGAAGGGCAG GACTTACTTT CTGGTCCCAA
 601 CAGGATACAG TGAATAAACA AGCACAAACC AGCAGGTGGT GAAAAAAAAA
 651 CAGCAAGAAC CAGCAGTGGC CTGGAAGGCA TCCTTTAGTT GCCCCGGCTG
 701 CTCATTAGCA TAAGACACTC CTACCAGAAC CATGACAGTT TACAAATGTC
 751 ATAGCAATGA CCCACGAGTT AGTACCCCTT TCCATGGCAA TGGCCCAGAA
 801 GTTACTGTCC CGTTTCTGGA GATTTCTGAA TAACCTGCCC CTTAATTTGC
 851 ATGAAATTAA TAGTTTATAAG TAGGCATAAA TACAGCTGCC AATAGCCCAT
 901 ACACTGCTGA CTCTGGGAGC ACTGCCTATG AATTAGCTCT GCTTTTCAAG
 951 GAGCAGTACC ATTCAGTAAA AGATTACTGT CTAGTATTAC CGGCTCGCCC
1001 TTGAATTCTT TCCTGGGCAA AGCCAAGAAC CTTCCCAGGG TAAGCCCCAA
1051 TTTTGGAGCT TGTCTGTCCT GCATTGATTT GACTCTGTAT ATTCATGCAT
1101 ATGGATTATG GTCTATCTTA TACTTTGATG AATAACTGGC CTTATGCATG
1151 TATTTTTTAA GCAAGTGTTT ACTGAGCACC TACTAGGTCC ATGATATTGT
1201 GTTATGTACT AAGGTTAGAC AGATCTAAGA ATATTAAAAG CCCTGACTTT
1251 ATGGAGCTTA TAGTCCAGCA GGAAGGACAG ATCATCAATT AGTCATTATA
1301 AAAGCAATGA AATAAAAGAA GAAAACATAA AATAGGGGGA ACTAATCCAG
1351 AAAGCTTTTGC TGAAGAAGGG TTTCAAAGCC TGAAATCTGA AAGATAAATG
1401 GCAGTTGCTT GAGAGGGTGG TAGCAAAAAG GTCAGCACAT AGGACAGCTG
1451 GAGCAGCTAA GAACATGCCA GATTCAAGGA GCTGAAAGCA GCTTATATCT
1501 GGATGGTCTT TTAAACATTG ACTTTTTTAT ACTATTACAA AAGCAATATA
1551 TGCTCATTAT AGAAAATTTA AAAAATACAA AAGAAGGCAA TAGTCACCAA
1601 TGTACTCTGC ACCAAGAACT GCTTTGTCAT GCCTTTATCT TCATTCTAAA
1651 TCTGTGAGGT TTTGTTTTCT TAAGAAGAAA TGTCATGCAC AATTTACTAT
1701 TTTCCAACTT TTTTTCTGCT AAACAATGTA TATCATGAAG AATTTCCCAA
1751 CGTTTTAAAT ACCCTTCTAC AACATCATTT CACCTTGCTG CATTATGTTC
1801 CATTTTTTTA AATAAGTATT TGCCCCAGGT TGGATTTTCT GGGGGACAGA
1851 CTCTGAGGCA GAATTCATAC AATAATGTTT ATTAAGGAGA ATCATCATCA
1901 TCGCCTGTGG AAAGGAAGTA GAGAATCAGG AGTAAGGAAA GAGATAAATC
1951 AAAACTGTGAT ACAGACTTCA AAACAGCCAG ACTCAACTCC ATGAGGAGCT
2001 ATGGAGCTAA AACTGCTCTT CAGAGATGTC CTACGTTGGG CTGAATGAC
2051 CAGGCCTTTA GACCGCAAAC AGGTCAGTCA CTGGATGTGG CAGGAAGGGA
2101 CGTGAACTTG GAGGAAGTGG CTTTCTACAG CTAAGGCCAT TCCTACAGAA
2151 AATGACAGCC AAGGGTGATC TGTTGACAGC ACTTCCAGTG GATGGGACCA
2201 GTCCTTTATT GCCTGCATAA ATTTTCCTGC CAAGTATGAC ATGTTGACCA
2251 TCTTGCCACC TGTAGACAAT GTTTGCAGCA TTTGTAGTTC TTTTTCTTCT
2301 CAGATGTCCA TGTCCCTATC CCTACCTCCT TGGCTCTTTT GAGCAACTTC
2351 TATTCAATCC TCAAGGCCCA GTTCAAATTC TTCCTCCATA AGACCTTGCC
2401 TGTCCAGCCC TGCTCATTTT GCTCTTCCTG CTCAGAATTC CTTTGCTTCT
2451 TCCTTCACTC TCATCCTTCA TCCCTCATCT GACACATTAC ACATATCCTC
2501 TCAATAACTA CTTGTCAGAT GTCCTCCATT CTCATGTTTT TATATATATT
2551 TATCTCCCCA AATAGTTGAC AACAGTGGTT CCTGAAGGAT AGTTGTCAGA
2601 TCAGCAACAT CTGCTTTGCC TGGGAACTTG TATATCAATT TTTGGGTTC
2651 CACACAGACC TGCTGTATCA GACTGTGAGT GGGGTCCCGC AATTTGTGTT
2701 TTAACAAACC CTCTAAGTAA TTCTGATGCA TGCTAAAATT TGAGACACTT
2751 CTATAAATTT TTTTTTCTTT GAGATGGAGT CTCGCTCTGT CACCAGGTTG
2801 GAGTGCAGTG GCGCGATCTT GGCTCACTGT AACCTCCGCC TCCCAGATTC
2851 AAGCAATTCC TCTTCCTCAG CCTCCCAAGT AGCTAGGACT ATAGGCATGC
2901 ACCACCACGC CCGGCTAATT TTTTTTATTA TTATTTTAGT AGAGATGGTG
2951 TTTCACCATG TTGGCCAGGA TGGTCTCGAT CTCCTGACCT TGTGATCCAC
3001 CCACCCTCAAC CTCCCAAAGT GCTGGGATTA CAGGTGTGAG CCACTGTGCC
3051 CGGCCTATAC ATTTTTTTAA GGTTAAGTAT ACAATGGTGT CTCACACACA
3101 TACATGCACA CATATACACT GCATTCCATA ATATTCGGTT AATTGAGTTT
3151 TAATTATAGT GGTAGTTAAT GCTTATTGAG TTCCTACTAT GTGCTGGGAA
3201 TTACAGTTAG TGTTTATGTGT GCATTATCTT TTTGCATTTA TTGCAACAGT
3251 CCCATGGAGT ATGAACCATT AGAATTCCTA ATTTACAGAT GCATGAACTG
3301 AAGCATAGGA GCAGTTTAAC TAAATTTCTC AAGATTATAC AGCTAGTTTA
3351 TGTAATAGTG TTAGAACCAG TGTTAAAACT CAAACAGTGG GACCCAGGAG
3401 CTTTCTCCTA ATGACTATGC TTTGTTTTTG CCCTATATTC TACCTGGGCA
3451 TGTGATGTTT GGCCTTCTCT CTTGCTCTTT TTTAAAGCAG CCCCTGATGC
3501 AAATGGTTCT CTCCTTCTCT CTGAGTGATA ACAATGGGCA AGAATAGTGA
3551 GGATGCTTAG AAGATATTTG CAGCTACAAA TTTTCCAAAG AATGTCTACA
3601 TGTAACTACT GTATAGAGTA AGGATTCTTA ACCAGGGGTT CGTATGTAGG
3651 CAACAAGATA TCTGAAACTC CTGAAATTGA ATGCAAAACC ATGTTTTTGT
3701 ATCCATTGTA TATCCATTTT TATAGTTCTC CTCAAATTCA CAGAGGGAAC
3751 TTTAACCTGA AAATGTTAGG AATCAATGCT CTTGAGTCTG TGGTTTTAGA
3801 ACTGGAAAGA ACCTTAGGAA ATGCATGGCC CAGGAATGCT CATAAGTTGT
```

FIGURE 3A

```
3851 CCTGGAACAG GTGCCCCACT GGCTGCTTTA GAACCATCTT ATCTGTAACC
3901 TGAAGTGGGC TCAAGACTCT GTATGTTTCA ATGCCCAGAA GATTCTGATG
3951 CACAACGAGG TTTTGGAATC AATGTTCTGA TCCAGTGGTT CTCAAACATT
4001 AGGGTACATC AAAATTCCCT AAAGAGCTTG AGACACAAAC TGCTGGGCCC
4051 AGTCCTCTGA GTTCCTGATT CAGTAGGTTT GGTTGGAATT TGCATATCTA
4101 ACAGATTAGT CCAAGTGATG CTGATGCCTT TGTCCCAAGG CCCATACTTT
4151 GAGAACCATA ATTCTATTCC GGTTTCCATA TTAAGACAAA GAAAGTAAGG
4201 ACTAGAGAGG GTTAGCAGAT TTTTCTAAGG TAACATGATT AGCTAGGGAA
4251 AAGCAAGGAC TTTCACTGTG TTTTACAGCA TCAAGGAATC TACTCTTACT
4301 TTTGGATCAT TGAGAATATG GCCACAGAGA ACTGAACCTA AAAGAAATTG
4351 TGCTTTTTCC ATAGAGTGAA ATCATCCAAC ATCAAGGCTA TCCCTGTGAG
4401 GAATATGAAG TCGCAACTGA AGATGGGTAT ATCCTTTCTG TTAACAGGAT
4451 TCCTCGAGGC CTAGTGCAAC CTAAGAAGAC AGGTGTGGGT CACCCCATGT
4501 CACCGCAACA CAGCAGTCTT CTCTGCAGTC ACGATTTCCT TGTGATTTGA
4551 ATGTAGAAGA GAGCCTGGGT TCTTAGTGCA GAGTGAGGTC CATTGTTCAG
4601 GTCAAAGGAT GGTGTCAGTT CCCCCATAGT CTCCATCACC ACCACCGTGT
4651 CCGTCCCCAC TGCCACCAAT TATCTCAATT AAACATACAG TGTTTGCTTT
4701 TCAAAACACT CCTTCAAGAA AAGTTCATTT CTTGACTTAT TTTAGCGCTT
4751 AACCCATTCC CCAAAACTCC TCCTATGTAG ACATTCTAAA ATATTTACTG
4801 ACAATTCCTT GAACAGACCA TATCAACCTC TGATTATGAA GAATTCAAGC
4851 TTCTTTATGG CACCTGGTAC CCGCTCCTGT ATACTCTGTA TTCCTCATCT
4901 AAAGAGCACT TAAAATATTT AAGATGTTGC CTAGCTTTTT ACTAAGGGCT
4951 TTTGAAAAAC GAAAGTTCTA TACATACATT TTATTTTATT TTATTTTATT
5001 TTATTTTATT TTATTTTATT TTGAGGTGG AGTTTTGCAC TTGTTGCCCA
5051 GGCTGGAGTG CAGTGGTAGG ATCTCAGCTC ACCGCAACCT CCGCCTCCTG
5101 GGTTCAAGCA ATTCTCCTGC TTCAGCCTCC CAAGTAGCTG GGATTACAGG
5151 CATACACCAC CACACCTGGC TAATTTTTGT ATTTTTGGTA GAGACAGAGT
5201 TTCTCCATGT TGGTCAGGCT GGTCTTGAAC TCCCGACCTC AGGTGATCCA
5251 CCCGCCTCCA CCTCCCAAAG TGCTGGGATT ACAGGCATGA GCCACCGCGC
5301 CTGGCTATAC ATACATTTTA AATGTTTGAT ACATGTCTCC ATAGTTCATA
5351 CAATTCCACC CTTTTGTATG TGGGATTTTC AGCTATTGTT ATTTTTTAAA
5401 CATTTGTTTT CATTACTAAA ATATGCCTAT TTTTCATTTC TATTTGGCTG
5451 GATTCTTTTT AATACTCTAG CAGTAGGTTT ATAGTAGCAA CTATATTGTC
5501 TTTCTTGTGT ATAGGTAATA TAATTTCTTG TGTTATTTTG ATATGCCAGA
5551 TACACTGATA AGTGCTTTAT TTGTATTAGT CTCATTTAAT TTTCACAATT
5601 ACCCTAAGAA ACTGCTACTC ACATATGTTA AGCAACTTGC CCAAAACGTC
5651 TGTGCTAGTG CTTGCTAGTG AGTTGTAAAA CCTGCACTCA AATCAAATCT
5701 GTCTCTCTGC CATTATAGCC CGTGTTCTTA ACTAGGACCA GAAAATGCTG
5751 GACAAATGCT ATTGGGCTTT GGTGTAAAGA AACGTTGGGG TTCTGTTTTA
5801 CTCCAATTTG TACTTGTGTA GCTTTTTGAA ACCACCTTTT TTTTTCTCAC
5851 TAGCTGCACA GCTGCGCCTT ATACATGTCT AGCGTGCACC TGCCTTAGTG
5901 TCTTTGAACT TAAATTTCTC CCTCTGGACC ACTGTTTCAT CAGATGTCTA
5951 TGCAGCTTGC CTTGGCCCTT CTTTCAGCCA ACTTTATCAG AGTTCTTCCC
6001 TGGCCACCCT ATTCAAAATT GCAGTTCTAG GCTACCTATT GAGTTCTAGC
6051 CCCTTACCCT GCTTACTTTT CCATATAGCA CTTACCATCA CCTGATATAA
6101 TAGATATTTG CATGTTTGTC TATTGTCTGT CTCCCCCCAG TCAGAGTGTA
6151 AACTCAGTGA GAGCAGAGAC ATCATTTGTT TTGCTCAAGG CTAGAACCAG
6201 TAACTAAATG AGTGCTGAGC ACATTCTGGT GCTAATAAAT ATTTGCGGGA
6251 TGAATTATAG ATTTTGTATA AATAAATGAA TAGCCTGGGG ACACAGCCCC
6301 ACGAATCTCA GGGGAGTGGT AAAAGCACAG TTCTTCCAAG CAGTCGAGTG
6351 ACTTAGCAAT TACTAAGCAT GGGGGTCACC TGCAGCCCCT ATTCTATGGA
6401 TGGAATTTGT TTTCTTACAT CCTGTTGATT CAGACTGTTC ACACATTGCC
6451 CAGGTGTTTG AGGTTCAAGG AATCTGCCTC CTTGTTCCAG TCCGTGCAGA
6501 ATACTTCCCT CTAGTGGCCA ATGTTGTTGG CATGTGCCTC TTCAGAGGCA
6551 ATCTCCCATA TCAAAAAAAA AAAAAAAAAT TCACCAACCA AGAAAGCCAA
6601 TGAAATTCTT ATTGAAAACA ACTGAAAAAT GTTTACTGTA AAGCTTATAG
6651 CTTGTGGTAG CGGCCTTTTT ATCTTTATCA AAGAATCTTA GTTGGCTTCA
6701 ATATCAAGAG AGAAAATAGG CTGGGCCATC CTCAGAAATG ACAGCTGTGT
6751 AAGTGTAGCC CTTACACACT TACCTGCTGG GTGTAAATTA AATAGAAGAC
6801 CTAGGGGATG TTTGAAATGA TATAAATGGA CCATTCCTCT TGTTAGGGGA
6851 ATCACAAGAA CAAACTATAT GACTAAGTAG AACCAAGGTG ACCTTAACCA
6901 TGGGAAATGC CCGGACTCTC AAGGGGAGCA TTGATCACCT TGGTTTGATT
6951 GTCCTGTGTT AACACAGCTG AGGTCACCTC CCTGAGAACT AAGAGGATGA
7001 ACTAAATGAC CAGATTAGAT TTTCAAGGAA AATCTAAAAT AACACTGAGT
7051 TCCTTCCTCC TGGCCCTTCA CTCACAGTCC ACAGTGACCC ACACGTTCTC
7101 TCCCTTGAGA GACAAAATGA GGCAGATGGA ATTCATGAAG ACTGTCAAGA
7151 TGCTGGATGA GTTTGGTGTA GAAGGCTTTT GTCCTACAGG GAGACTGCAT
7201 GTGTGTTTGG TGCCCGTTTA TAGCAATAAC AACAAGAGCT ACCCATCTGA
7251 TCTGAGGTCG GGCAGCATGC TGAGTGCTTA ATGCACAGTA CCGCATTTAA
7301 CCCTCCCCTG CCAAAACCCT GTGAGGTGGG CAATTGTCCT CATTTTGCTA
7351 ATGAGAACAC TGAAGCTCAG AAAGTCACTT GCTTTAGAGA ATTATAACAA
7401 TAATAATGAA ACAATAAGG CTGTTTTTTA CTGCAGGCTT TTCTGAGCC
7451 AATACTGAGG TGTGGATATT GCATTCATGA TTTGATTTAA TTCTCACAAG
7501 TCCTGTTGAG GGCATGACAT ATTTTTTACT CCTAATAGGG CAGCACCTTA
7551 TTAATCTTTC AGCCAAATTT GCTAATGTCA AAATAATATA TATGCCTTAA
7601 TTTATTGAAC ATATTAGAAT TCTTAAAACC CTTCATCCTT CTCTATTCTC
7651 TACTGATATT CTTATAATTC TTTATTTTGA TATAATTTCC AATTTATGGA
```

FIGURE 3B

```
7701 AAAGTCCTGG GAATAGTACA AGGGACTTCC ATATGCCCTT TGCCCTGATT
7751 TACCAACTGT TTACAGTTTT ACCCCATTTA TTTTATCATT ATCTCTCCCC
7801 CATCTCTTAC GTGTATCTTA ATACTTTTTC CAAAACCTTT GATGGTAAAT
7851 TTGAGACATA CATCATGCCT ATTTGCCCCT AAGTACTTCA GTGAGTATTT
7901 TCTAAGAACA AGAGTATTCT CTTCTATAAC TGCAATACCT TTATCAAAGT
7951 TAGAAAACAA ACATTGATTG ACATTAGTGT TTAATTCGTA GTCTATATCC
8001 AAATTTTGTC AATTGTCCCA AAGTCCTTTA CAGCTGTTTT CCCTCCTCTG
8051 GTCCATAATC TAATCCAGGA TCATTTACTA TACATTTGGC CACCAAGTCT
8101 GTCTCCTTCA TAAACAAACA ATTCCTAAGG TTTTGTCTTT TTGATTTTTG
8151 CATTTTTGAA GAGTTTTGGA CAGGGATTTA ATTTGCTTTA TCTGATGTTT
8201 CTTCATGGTG TGATTCAAGT TATATGTTTT TGGCAGGAAT AACCCAAAAG
8251 TGAAGTTATA TCTTTCTTGG TTCATCATAT TATGAAGCAA ATAATGTTGG
8301 CTTGTTCCAA TACTGATAAT AACTTTAATG ACTTCATTAA GGTGGTATCT
8351 GCCAGGTTTT TCTAAAGTTA GTATTTTTCC TTTTGTAATT AACAAATAAG
8401 TTATGGGAAG ATAATTTCAG GATATGTAGT ATTCTGTCTT TAAATTTTAC
8451 TCACTAATTT TAACATTCAC TGATAATTTC AATCTTTCTG AATTTGTTAG
8501 TGGGTATTGT ACTGTAAATC AATGTTTTGT ATTTACTAAT TGGCATTCTG
8551 TAAATAAGAG CTTTTCCTTC CAATTATTTA TTTGTTCATT TATTTATTGG
8601 TCTCTATATG GACTTGAACA TTCTTAATTT ATTCAATGGG ATATAATTAT
8651 TTACTATAAT TATTTTGATG CTCAATATTT CTGTATTTGA ACAGTGGGAG
8701 CTCCTTCAAG CTGGCTTGTG GGTCCTTTTG ACATGAAGGT CTCTTAATCA
8751 CTAAACCATT ATATATATGT GGTATACATA TACCTTAATA ATCATACTAT
8801 ACCATCTACT GGGGCACTTT CAATATTTCT GAAGAGCCCA GACAAGTCTG
8851 ATAATAATTA CACAAAACAA AGAACAGAAG TTAAACTTTA TAGATTCTTT
8901 TTCTGCCGGG CAACATGCCA TCCATTTCTT GTGCTCTATT TTATTAAAGC
8951 ATAACAAAAA TCTTTATTTTA CTGATGAGGA AATCAAGGCA CACACCAAAG
9001 GTCAAGTAAT TGGCCAAGAT AACTAAGCTA GCAAGCAGCT GAATCAAGAT
9051 CTGAACACAG GTTTGTTTGA TTTGAAAGCT CTTATTCATT ACTGGACAAC
9101 AAGAAAGGGA GAGAACATTT CATACAGTTG AAATTTTCTC TTTTTGCAGG
9151 TTCCAGGCCT GTGGTGTTAC TGCAGCATGG CCTAGTTGGA GGTGCTAGCA
9201 ACTGGATTTC CAACCTGCCC AACAATAGCC TGGGCTTCAT TCTGGCAGAT
9251 GCTGGTTTTG ACGTGTGGAT GGGGAACAGC AGGGGAAACG CCTGGTCTCG
9301 AAAACACAAG ACACTCTCCA TAGACCAAGA TGAGTTCTGG GCTTTCAGGT
9351 ATATGATAAT CTCGAGAACA GAGGTAGACA TGTCTGTCTT TCAAAAAAAA
9401 TGGGTAAAAA ATTACGGCTT CTAGTATTTG GTTGATTTAT TTTGGTTGAG
9451 TCATCATTAT CTTAACATGA TATCCCCCAG TTTTCTTAAT TAACTAGTGA
9501 TTCCTTGGTT GAAGTAGTGA GGAATGCTGA GTTCCCATG TAGAAGGTGG
9551 GTCTAGCTAA TAGGGTGAGA ATGGTGGTTG GTGTCAGGTG ACTAAGATTG
9601 GAATGAGAGA AGTGTAGATC AATTTCCTCA TGGGGAGGGG CGGGTAATAG
9651 TATAATAGTA CTCCAGAAGG AAAAGAGACC AGGCAGCATT AAAAAAAAAG
9701 AAAGGAAACT ATTAAGCCTA GTGTGTTAGT CCGTTTTCAC ACTGCTGTAA
9751 AGAACTGCCC GAGACTAAGT AATTTATAAA GTAAAGGGTT TTAATTTACT
9801 CACAGTTCAG CGGGGCTGGG GAGGCCTCAG GAAACTTACA ATCATGGCAG
9851 AAGGTGAAGG GGAAGCAAGG CACCCTTTTC ACAAGGCTGC AGCAAGAAGT
9901 GCTGAGCAAA AGGGGGAAGA GCCCTTTATA AAACAATCAG ATCTTATGAG
9951 AACTCACTAT CACGAGAACA GCACAGGGGA AACCACTCCC ATGATTCAAC
10001 TACCTCCACC TGGTCTCTCC CTTGACACAT GGGGATTACA GGGATTATGG
10051 GGATTACAAT TCAAGATGAG ATTTGAGTGG GAACACAAGG CCTAACCATA
10101 TCACCTAGGG ACCATCGATT TGACTTACCT CTCATGTTCT TACAAAAGAT
10151 TTTTAACTCT TTTATTTAAA TTACCTATTG ATGTTCAACT CACTTTTTAT
10201 GGCTATCAGA GACGGACCAC TTCAGCATCT TTACACATAT TCCTGTAAAT
10251 GAATCTGCAG AGCCCTGTGC GGTTCTGCTT AACAGTAGAA CAGGACACTT
10301 CCACTAGCAG TTGCGTTATG TGCTCAGTAA ATATTCACTG AAGATAGTTA
10351 TTGCTACGTG ATAACATCTA GAGAAAACAG CAGTTTGCTG ACAGCCTGTG
10401 ACTCCAGAGG CACCCATGCT TCATAGGTTT GAAAGAAATC CATTCTGAGT
10451 GTTGTGAGGG ACACGGTAAC AAGCTGTCAG AGTTGACAAC TCAAGGGCTT
10501 GTTTGTAAAC CTGGTGTGGG GGGGAGCTTT TGTTTGTTTC TGATTATAAT
10551 TTTTCATATA ACTTTGTCTT TTCCCCTTGT AGTTATGATG AGATGGCTAG
10601 GTTTGACCTT CCTGCAGTGA TAAACTTTAT TTTGCAGAAA ACGGGCCAGG
10651 AAAAGATCTA TTATGTCGGC TATTCACAGG GCACCACCAT GGGTAGGTTC
10701 AAAGAAAAGC AGGTTTGTAT ACTCGGAAGA AATGTGAGCA TACGACACTA
10751 GCTATCCCTG AAATCTGTCA CCTTGTGCTT CCTTCAGACC TGCTCTTTTC
10801 ATCTTCAGAA TCTACTAGTC CCAGCAATG TGTCTAGCAT ATAGACATAT
10851 GTGCTAGATA TAGCATATCT CTGTGCTATA TGTGTCTAGA TATAGCATAT
10901 CTCTCAATAT AAATATTTTC TCAAAGCCAA CATCGTGTTA TTCAATTATT
10951 TATTTAACTC ATTGAGCACC TACTACTTGA AAGCAAATAT GCTGGTGTCA
11001 TAAGGACCTT ATAATTTTAT AGGGAGGGTA AGATGCAGTC ACATATATAC
11051 TTATTGAAAT ATGTATTTAA AAGCAAAATA TACATTTTAT GAGTTCTAAA
11101 AATATTTCGT ATTCATGTTG ACATATTTCT TCTTTTGCAG GCTTTATTGC
11151 ATTTTCCACC ATGCCAGAGC TGGCTCAGAA AATCAAAATG TATTTTGCTT
11201 TAGCACCCAT AGCCACTGTT AAGCATGCAA AAAGCCCCGG GACCAAATTT
11251 TTGTTGCTGC CAGATATGAT GATCAAGGTA TGAGACTCCT CAGAAAACTT
11301 CCTGTGTACG TAGAAAAATC TTCCAGCCCA ATTTCCTAAA ACATAAACTT
11351 TTAAATTACA GTCACATCTT TTCTGTCTGT CATGTCTATG TCACTTCATA
11401 TTTTCACAGG GATTGTTTGG CAAAAAGAA TTTCTGTATC AGACCAGATT
11451 TCTCAGACAA CTTGTTATTT ACCTTTGTGG CCAGGTGATT CTTGATCAGA
11501 TTTGTAGTAA TATCATGTTA CTTCTGGGTG GATTCAACAC CAACAATATG
```

FIGURE 3C

```
11551 AACATGGTAA GTGGGAGCCT AGTAAATTCC CAGCATCCCA GCATAAAGCT
11601 GGGAGTCATA TGGCTCACCC CTGGAGGGAG AGCTAATGCC AGTGAAGACT
11651 CAGAGTAATG ATATATTCTC AGTAACTCAG TTCTCTGCAA ACTGTAAGGA
11701 AATAAGGGAA ATGCTTCAGT ATGGACTGAA ACAAGGTTAA CATAAGGGCA
11751 TTGCTGATAT TAAATCACAG ATTATAGATG GAAGAGGTCT GAAAGCAGCT
11801 TTACTACAGT GAATTAAATT AAAAAGAGCA ATTAGCACAT GTTAGACAAC
11851 AGAGACAACT GTCATGCATC ATCCACCTCT ACCCTGCACT GGGGTCCTGT
11901 AGGTTTGTAG TTTAAGTTCT TTGATGGAAC ATCAGGGACC TTCATTTTGG
11951 CTTAGGCTAC CAGTTGGTAT CACTGGGTGG GTTCCCTAGG AAGCATACTC
12001 TGAGATGGAG GTTAATGTGA ACAATGATTT GGGTCCTGCT CTAGGGATAA
12051 TACCTAGAGA AGGAAAAGAA ACAGGACTAG GTAGGTGAAA AAGTCAAGTA
12101 GTGATGCAGT CTCAATAGGA GACTTAGTTG ATCCTGCAGG GATTTTTGAA
12151 GATAGGATGA CCCTTCAGAA CCGTCTCAAG TTAGGAAGAG AGGGTTGGGT
12201 CTTTATACAC CATATCAGTC AGTCATTTAA TGTAGCCATA CCAGTAACAG
12251 GGTAGCACTG GGCAATGTAT CTGCCTACAA TTGGTGCAAT CCTCAAAGCA
12301 GACTGAGAGT GGAGGGCTGT TTGCCAGCAG CACTCCCAGC AGCTGGGGCA
12351 ACATTTCCTT AATTCTGAAT ATTTTTTCTT CTTCTTTAAG ATTAATAATT
12401 TGATTTATAG TAAGGATATG AAAAGTATAT ATTATGTATC AGGCTAATTT
12451 ATTACCTATA CCAAGCCTAT GAGTGTTATT AATATCCCCA CTTTGCAGAT
12501 TAGTATACTA AGATTTAGTA GATTAAGTGA CTCACTCAAA TTCACCTAAA
12551 AATTAAACTG CAGAACTAGG ATTTGAATAC AGGCCCAATG CTAGAGCCCT
12601 CATCCTAAAT ATCACTAGTA AAATTTTTTT TAATTAGGGG CCAGATCTCT
12651 GATGAGAACC TATTCTCAGA TGAAAAATAC CGGTGTCTGG CAATACATTT
12701 AATGACATTT TATTTACGTG CATGTACATA TTTTTGTTTC ATAGATAATT
12751 GCTGATAACT TAATAATGTT ACCATTTCTT AGTCTGACAC CCTGGAGATT
12801 TGGTCTTGAC AGGGTATACA TCTTGTGAGT TTTTCTATGT CCCCCAGAAT
12851 ACTCATGGTT TGTTACAGAG CCGAGCAAGT GTATATGCTG CCCACACTCT
12901 TGCTGGAACA TCTGTGCAAA ATATTCTACA CTGGAGCCAG GTAAGAATGT
12951 TGAATTTGCA GTCTTTGCTA AATGTCCTGT TATATTTTGT GTAGAATAGT
13001 CAAAGGACAC CATTTAGATA AGCCAGGGAT TATTTCACAC TTATTCTAAG
13051 ATGAAATGCA GTATCGTCGA TGCTATTTTG ATGGAGAATT TGATCTAGAT
13101 CACTGAAACT TTTCAAGAAA TGGGAAGAAA GGACAGAAGT AGCCTAAGAA
13151 CTTCTTTAGA TCTTAAAAGT ATGAATTTAG ATGATCCAAG TGAGACTTCT
13201 CTCTGTCTCT AGACACCTCA AAGATGTGGC TGGAGATAAT TATGTTTCTA
13251 CATCTTCTCT TCAGCTCCTC CAACAATACA GTCAAGTAGA AACAAAAATG
13301 CTAATGTGGG GTCTGTCAAA AGAGATATTC ACAGGAGTCC TTCACACTGC
13351 AAACTTTACC TGCAATTACA GGAAACACAC ACCTCTGTGT GTCTATGTGG
13401 TGTGTGTGAA AGAGAGGGAT GGGGGAAGGA GAGAGTTCTC TCTGTTGACA
13451 GGTAGGGAGA GACAGAGAGA GAGAGAGCAA TTGTACCATC AAAACCAGAG
13501 AAGAATTATA AGTTCAATTA AATTTTGGTT GCTATCTTCC AGGATCACCA
13551 CATTGCACAA TTCCAGGGCA CGATTCCCCA TTGTAGCCCA CACAGTTGTG
13601 GAGGATACCC ACTCACATTA ATTACAATGA AGATGCACTT CCTGGAGTTG
13651 CTAATGCAAT GATCAAGAAT TTATGTAGTC CCTCTTTCTT CTCAAAAGGC
13701 CTCATTCTTG TCTTACCATT TTCCTGAGAC GCTTATCCCA ACATTGAATG
13751 GAAGAGCAGC TCAACCATTG CTCTCTCCTT CCCTCATGAG TGCACACTGG
13801 GTAGCACATT TCCACCACCC CACCACGTCT ATCCACTGAG ACGTTGGAAT
13851 TCCTTGTAAA TTTTTGTCTC CTTTTAGGCA GTGAATTCTG GTGAACTCCG
13901 GGCATTTGAC TGGGGGAGTG AGACCAAAAA TCTGGAAAAA TGCAATCAGG
13951 TAAGAAAATC AAATACCATC TGCTGAAAAT ATATACATTG GAAATGTATG
14001 ACAGGGACGT TATAATGACA GTTTATTCTA GATATGGGAA TAAAATATGA
14051 AAATTTAAGC AGAAAATAAT GGTTCATGTT TGACTCCATT TGAAAATGGT
14101 TAAGTTCACA GCTGATCCAA GAAACCTCTC TGCTTTTACA ATGGAGTAGG
14151 AGGCCTTTTT AGCTGAGGCT GTCTCCCTAA ACAAGGTACT GGGCTTCTCA
14201 GGAGCAAGAT GAAGTAGATT TAGTCAAGAG AAGAGTGTAG TCTATGGTGG
14251 ATACTAGAAG GATTATTTTA GAATTAAAAA AAATGGGATG GTGGCAGTAA
14301 GTTTGTTTCA TGGCACAGTA AAAGGAACAT TAAATGGCAA GTGAGGATTG
14351 CTGTGTAAGT TTTGCCTCTG CACTATAAAC TTCTGTAATA GGAGGGAGGC
14401 TGCTTTAATT TTTCAGGCTT CAATTTCTTT ACCTTGAAAA TAAAAATTTT
14451 GGGCTTAGAA AATCCATAGG CATTCTCCCT AGTTATACTT TAAATGAATC
14501 TGTAATTTGC AAGTTACATT TTTTAAAAAT GTTATTCAT TACCCAAGAA
14551 AATATGTAGC TAATGCTATG AACTAAAATT AGATATCAAA GTGTGGAGAT
14601 TCAGAATTGC ACAGGTATGC CCTTTAGAAC ATAAAATCTT CTGAAGATTT
14651 TTGGTAATCA TGTGTATGAA TGTAAATAAA TATTTACCAT AGAAACAATA
14701 CTGGAAGGGG CAGATTAGAC ACAGCTTAGT CTTTCTTTGA GACCCTCACA
14751 TCATAAATTA ACATCCGCTG CCATATGTCT ATCTAGATGT AAAATGCTAG
14801 GAAACTGGAC AAACTGTGCA GTGCCCCTGG ATAGCGAACT CTCAATCTCT
14851 GGTATCAGCT GCTTCTCTTG AAGTCTTTCT TCACTGTTTC CCAAAATATG
14901 TCTTTAGAGA AAGTATTTCT GTTCAAAGAT GTTTTTTTAA TTATATTTAT
14951 TTACTTTTGA GACAGAATCT TGCTCTGTCA CCCAGGCTGG AGTGCAGTGG
15001 CGCAGTCTCG GCTCACTGAA AACTCTGCCT CCTAGCTTTG AGCCATTCTC
15051 TTGCCTCAGC CTCCCGAGTA GCTGGGACTA CAGGTGCACG CCACCATGCT
15101 CAGCTAATTT TTTTTTTGTA CTTTTAGGGA TGGGGTTTCA CCATGTTGGT
15151 CAGGCTGGTC TCAAACTCCT GACCTCAAGT GATCCACCTA CCTCAGCCTC
15201 CCAAAGTGCT GGGATTACAG GCGTGAGCCA CTGTGCCCGG CCCTAAGATG
15251 GCTTTAATTT ATCAACATTT AATGACTGA GTTCTAGAGA AATTGATTCA
15301 TGCAGAATAG GCACCAGAAA ATGGGAGTGG AAGGGAAGAG TAAACAAACA
15351 CACAAAAAAA ATCATAGAAT CACAGAAACT CAGAGCGAGA TATGACATTC
```

FIGURE 3D

```
15401 AGTTCAATCT TTTCACCTGT AAGATGACAA AAAAAATTAC TAGCCCCATA
15451 GAATTTTTCA ACCTTCCTTA TCCAAATTAG GCCATAACTG AGCCACAAAG
15501 AGAAACCAGA GCATCTAGGA TTGGAGCCAA GACTCCATGG TGGATTTCCT
15551 GAGTAAGAAA TGGGCCTTAC CACTTCTGAG GAAAGTTCTG GATGCTGATT
15601 AATCTCAAGG GCTCAGCCGG CTAGGCTAAT TCTACTAACA CTGCATAAAT
15651 ACGGAAAGTT CCCAGGTATT AGGAATACTA ATTGGTATAT TTGGTGGGGA
15701 AGGGTGAGGA ATAAGGATTG GAGCAGGTAT TTAACTTTTA CTTCCCTTTA
15751 GCTCAAATTA CCTGAGTGCC ATAGGCCATG GTTCTGGCAA ATGCAGTCAA
15801 GCCGGGTCTG CCTCAAAGGC TGCCTGGGAT CACATAAAGA CTGTGAAGAT
15851 GCAGAGCCCT TCCCAGCAGA TTCCTTGCTT TTCTCTGTGG AATATAATTC
15901 TTCTTTCATG AAATGTTTGT GAAATTATCT TTTAAAAGAA CAGGGGCATT
15951 ATTTTTAAAA ACAATTTGTT TACAAAATAT TTAATAGGAA GAAAAAGAA
16001 ATACAAGGCA TTACATGTTT TTATGTGTTT TGTCATTTGA TCTAGCAAGT
16051 TATTACAGAT ATTATCCCCA GTCACAGAAG AAGAAACTGA GGTTCAATAA
16101 TGTTAAGTAA TTTTACCTTA AAGTAAGGGC GGGAACAGAA ATTCTTAACA
16151 GAGTTGTGTG GCTCTAACAC CCATGTACCC TTCACCACAA CAGATGGCAT
16201 GTTTATTATG TCTATTTGAA ACATAAATTA TGAGCCTGAA AGTCCAAATG
16251 TTACCTAGAG TTAAGAACTA TTCCTTTTCT CTAGCCAACT CCTGTAAGGT
16301 ACAGAGTCAG AGATATGACG GTCCCTACAG CAATGTGGAC AGGAGGTCAG
16351 GACTGGCTTT CAAATCCAGA AGACGTGAAA ATGCTGCTCT CTGAGGTGAC
16401 CAACCTCATC TACCATAAGA ATATTCCTGA ATGGGCTCAT GTGGATTTCA
16451 TCTGGGGTTT GGATGCTCCT CACCGTATGT ACAATGAAAT CATCCATCTG
16501 ATGCAGCAGG AGGAGACCAA CCTTTCCCAG GGACGGTGTG AGGCCGTATT
16551 GTGAAGCATC TGACACTGAC GATCTTAGGA CAACCTCCTG AGGGATGGGG
16601 CTAGGACCCA TGAAGGCAGA ATTACGGAGA GCAGAGACCT AGTATACATT
16651 TTTCAGATTC CCTGCACTTG GCACTAAATC CGACACTTAC ATTTACATTT
16701 TTTTTCTGTA AATTAAAGTA CTTATTAGGT AAATAGAGGT TTTGTATGCT
16751 ATTATATATT CTACCATCTT GAAGGGTAGG TTTTACCTGA TAGCCAGAAA
16801 ATATCTAGAC ATTCTCTATA TCATTCAGGT AAATCTCTTT AAAACACCTA
16851 TTGTTTTTTC TATAAGCCAT ATTTTTGGAG CACTAAAGTA AAATGGCAAA
16901 TTGGGACAGA TATTGAGGTC TGGAGTCTGT GGATTATTGT TGACTTTGAC
16951 AAAATAAGCT AGACATTTTC ACCTTGTTGC CACAGAGACA TAACACTACC
17001 TCAGGAAGCT GAGCTGCTTT AAGGACAACA ACAACAAAAT CAGTGTTACA
17051 GTATGGATGA AATCTATGTT AAGCATTCTC AGAATAAGGC CAAGTTTTAT
17101 AGTTGCATCT CAGGGAAGAA AATTTTATAG GATGTTTATG AGTTCTCCAA
17151 TAAATGCATT CTGCATTACA TAAAGCATGT ATGTGCATTT CAGTGTCTAG
17201 ATTCTAGTCC AAGCTTGTTG GAAGGTTTAC AGCTTGTTGC TAGGAGACCT
17251 AATGACTAAA AATTTCTGGC TCAATTTTCT GCCTCCAAAA ATTAAAAGCT
17301 AGGGAGAAAA TTGCATAATG TCATGAGCAT GATGAAACAA ATTGTCATAT
17351 ACTTTATCCT TTAATCTTGA CAAAGTTAAT GTCAGACAGT CTCTGCAACT
17401 CATTGACAAA CCATGCATTTA TTTCTTCAGA AAATTATTCC ACTTTTACAC
17451 AATTTCAAAG ATGACAGTTG TAAATTACAT TGGTACTATT TTGCAAAATC
17501 TCTGAAACCA AATCAAAGGT TTGTGTGTGT CAAAAGTATA TTGTTGAAGG
17551 TATACTGGTG TGTGAAATTC ACTTGTGTGG GTTTTTTGTC CCCAAGGGTC
17601 ACCTGGTAGC TCAGCTCAAT GCCAGTGAAT CTTAATTTAT TAAGACACGT
17651 TTAAAGACTT CAGAATCTAT ATCTACACAC TATTACTTCC TTCATAAAAT
17701 AAGTTTCTTA AATCCTGTAC ACAGTTGAAT ATATATTGCT GGATTTGATT
17751 TTCATTAGAG CTTTCAAGGA TGGTAAATCT TTCATTCTTA TACTGTACTT
17801 GTTACCACAT ACAAAGAGGC TGGCTTAGTT CCTGTCTGCA GCTATGTGAG
17851 ATTCAGTCTT GATTTTCAAA ATTCAGTCAT ATTTTTAAAG TGAATTTATT
17901 TCTACTCTGT GTCATTCACA GAAGAAGTGA GACAGATATT TTGATATTCG
17951 CAATCTCTCA CTTAGACAAA TAATCCAGAT CCTACCTCAT TGTATAGCTC
18001 TGTTTCTTTT GAAGAACTTT ATCCAAATAA GTTACAATAA TATTTTACAT
18051 CTATCAATAA AATAAACAAA ACTAACAAGC TTGGCAACCA CCTTGTATTT
18101 ACAAAAGGAT CATGAAGATT TTTTTAAACG AACATTTTCA TAGTTGCATA
18151 GTCTTGCTCA AACCAAGATG GCTTTTATTT GTAAACCGAA ATCTCTAGTG
18201 GTATGCTGGT AAACGAACTT TATGGAAAGT AAAAAACAAA AAAACAAAAA
18251 CAAACTCTGA TTTGTCAATT TGCCACTTTC TGTGGTGTAA ACACACTCAC
18301 CGCTGACACT TGATAGATGT TTTTATTGAA ATTCCTTCAC CAAAGGAATA
18351 TTTACTTGTG AATCTCTAAG CCCACACACA TACACAAATA CCATTCTGTA
18401 CAAACATACG TATTTAATAA TTTGATTCTT CTGCTCAATA CTCAAAGGGG
18451 GCTGGGAGGA ACAGTTTGTC TCCTAGGGCA TGACATAGAC TGGACAGTCT
18501 TTTTATAAGA GTGATACAAC TGGGAAGGGA GAACGCTGTT TCAGAAGATA
18551 ACTC
(SEQ ID NO: 3)

FEATURES:
Start:   2001
Exon:    2001-2072
Intron:  2073-4364
Exon:    4365-4482
Intron:  4483-9149
Exon:    9150-9348
Intron:  9349-10582
Exon:    10583-10692
Intron:  10693-11140
Exon:    11141-11277
```

FIGURE 3E

```
Intron:  11278-11409
Exon:    11410-11556
Intron:  11557-12868
Exon:    12869-12940
Intron:  12941-13877
Exon:    13878-13949
Intron:  13950-16284
Exon:    16285-16551
Stop:    16552
```

SNPs:

| DNA Position | Major | Minor | Domain | Protein Position | Major | Minor |
|---|---|---|---|---|---|---|
| 1709 | T | G | Beyond ORF(5') | | | |
| 1816 | G | A | Beyond ORF(5') | | | |
| 1981 | A | G | Beyond ORF(5') | | | |
| 2174 | T | A | Intron | | | |
| 2285 | T | C | Intron | | | |
| 3069 | C | G A | Intron | | | |
| 3086 | G | T | Intron | | | |
| 3104 | A | G | Intron | | | |
| 3217 | G | A | Intron | | | |
| 3293 | A | G | Intron | | | |
| 3355 | A | T | Intron | | | |
| 3371 | T | G | Intron | | | |
| 3588 | G | A | Intron | | | |
| 4320 | G | A | Intron | | | |
| 4960 | C | T | Intron | | | |
| 5722 | G | A | Intron | | | |
| 6018 | G | A | Intron | | | |
| 6563 | A | - | Intron | | | |
| 6574 | A | - | Intron | | | |
| 6600 | G | A | Intron | | | |
| 10518 | G | C | Intron | | | |
| 10857 | G | C | Intron | | | |
| 11109 | G | A | Intron | | | |
| 13112 | C | T | Intron | | | |
| 15905 | T | C | Intron | | | |
| 15968 | G | A | Intron | | | |
| 16626 | G | A | Beyond ORF(3') | | | |

Context:

DNA Position

```
1709    TTGAGAGGGTGGTAGCAAAAAGGTCAGCACATAGGACAGCTGGAGCAGCTAAGAACATGC
        CAGATTCAAGGAGCTGAAAGCAGCTTATATCTGGATGGTCTTTTAAACATTGACTTTTTT
        ATACTATTACAAAAGCAATATATGCTCATTATAGAAAATTTAAAAAAATACAAAAGAAGGC
        AATAGTCACCAATGTACTCTGCACCAAGAACTGCTTTGTCATGCCTTTATCTTCATTCTA
        AATCTGTGAGGTTTTGTTTTCTTAAGAAGAAATGTCATGCACAATTTACTATTTTCCAAC
        [T,G]
        TTTTTTTCTGCTAAACAATGTATATCATGAAGAATTTCCCAACGTTTTAAATACCCTTCTA
        CAACATCATTTCACCTTGCTGCATTATGTTCCATTTTTTTTAAATAAGTATTTGCCCCAGG
        TTGGATTTTCTGGGGGACAGACTCTGAGGCAGAATTCATACAATAATGTTTATTAAGGAG
        AATCATCATCATCGCCTGTGGAAAGGAAGTAGAGAATCAGGAGTAAGGAAAGAGATAAAT
        CAAACTGTGATACAGACTTCAAAACAGCCAGACTCAACTCCATGAGGAGCTATGGAGCTA

1816    CATTGACTTTTTTATACTATTACAAAAGCAATATATGCTCATTATAGAAAATTTAAAAAA
        TACAAAAGAAGGCAATAGTCACCAATGTACTCTGCACCAAGAACTGCTTTGTCATGCCTT
        TATCTTCATTCTAAATCTGTGAGGTTTTGTTTTCTTAAGAAGAAATGTCATGCACAATTT
        ACTATTTTCCAACTTTTTTTCTGCTAAACAATGTATATCATGAAGAATTTCCCAACGTTT
        TAAATACCCTTCTACAACATCATTTCACCTTGCTGCATTATGTTCCATTTTTTTTAAATAA
        [G,A]
        TATTTGCCCCAGGTTGGATTTTCTGGGGGACAGACTCTGAGGCAGAATTCATACAATAAT
        GTTTATTAAGGAGAATCATCATCATCGCCTGTGGAAAGGAAGTAGAGAATCAGGAGTAAG
        GAAAGAGATAAATCAAACTGTGATACAGACTTCAAAACAGCCAGACTCAACTCCATGAGG
        AGCTATGGAGCTAAAACTGCTCTTCAGAGATGTCCTACGTTGGGCTGAGATGACCAGGCC
        TTTAGACCGCAAACAGGTCAGTCACTGGATGTGGCAGGAAGGGACGTGAACTTGGAGGAA

1981    TGTCATGCACAATTTACTATTTTCCAACTTTTTTTCTGCTAAACAATGTATATCATGAAG
        AATTTCCCAACGTTTTAAATACCCTTCTACAACATCATTTCACCTTGCTGCATTATGTTC
        CATTTTTTTTAAATAAGTATTTGCCCCAGGTTGGATTTTCTGGGGGACAGACTCTGAGGCA
        GAATTCATACAATAATGTTTATTAAGGAGAATCATCATCATCGCCTGTGGAAAGGAAGTA
        GAGAATCAGGAGTAAGGAAAGAGATAAATCAAACTGTGATACAGACTTCAAAACAGCCAG
```

FIGURE 3F

```
            [A,G]
            CTCAACTCCATGAGGAGCTATGGAGCTAAAACTGCTCTTCAGAGATGTCCTACGTTGGGC
            TGAGATGACCAGGCCTTTAGACCGCAAACAGGTCAGTCACTGGATGTGGCAGGAAGGGAC
            GTGAACTTGGAGGAAGTGGCTTTCTACAGCTAAGGCCATTCCTACAGAAAATGACAGCCA
            AGGGTGATCTGTTGACAGCACTTCCAGTGGATGGGACCAGTCCTTTATTGCCTGCATAAA
            TTTTCCTGCCAAGTATAGCATGTTGACCATCTTGCCACCTGTAGACAATGTTTGCAGCAT

2174    AATGTTTATTAAGGAGAATCATCATCATCGCCTGTGGAAAGGAAGTAGAGAATCAGGAGT
            AAGGAAAGAGATAAATCAAACTGTGATACAGACTTCAAAACAGCCAGACTCAACTCCATG
            AGGAGCTATGGAGCTAAAACTGCTCTTCAGAGATGTCCTACGTTGGGCTGAGATGACCAG
            GCCTTTAGACCGCAAACAGGTCAGTCACTGGATGTGGCAGGAAGGGACGTGAACTTGGAG
            GAAGTGGCTTTCTACAGCTAAGGCCATTCCTACAGAAAATGACAGCCAAGGGTGATCTGT
            [T,A]
            GACAGCACTTCCAGTGGATGGGACCAGTCCTTTATTGCCTGCATAAATTTTCCTGCCAAG
            TATAGCATGTTGACCATCTTGCCACCTGTAGACAATGTTTGCAGCATTTGTAGTTCTTTT
            TCTTCTCAGATGTCCATGTCCCTATCCCTACCTCCTTGGCTCTTTTGAGCAACTTCTATT
            CAATCCTCAAGGCCCAGTTCAAATTCTTCCTCCATAAGACCTTGCCTGTCCAGCCCTGCT
            CATTTTGCTCCTCCTGCTCAGAATTCCTTTGCTCCTTCCTTCACTCTCATCCTTCATCCC

2285    AACTCCATGAGGAGCTATGGAGCTAAAACTGCTCTTCAGAGATGTCCTACGTTGGGCTGA
            GATGACCAGGCCTTTAGACCGCAAACAGGTCAGTCACTGGATGTGGCAGGAAGGGACGTG
            AACTTGGAGGAAGTGGCTTTCTACAGCTAAGGCCATTCCTACAGAAAATGACAGCCAAGG
            GTGATCTGTTGACAGCACTTCCAGTGGATGGGACCAGTCCTTTATTGCCTGCATAAATTT
            TCCTGCCAAGTATAGCATGTTGACCATCTTGCCACCTGTAGACAATGTTTGCAGCATTTG
            [T,C]
            AGTTCTTTTTCTTCTCAGATGTCCATGTCCCTATCCCTACCTCCTTGGCTCTTTTGAGCA
            ACTTCTATTCAATCCTCAAGGCCCAGTTCAAATTCTTCCTCCATAAGACCTTGCCTGTCC
            AGCCCTGCTCATTTTGCTCCTCCTGCTCAGAATTCCTTTGCTCCTTCCTTCACTCTCATC
            CTTCATCCCTCATCTGACACATTACACATATCCTCTCAATAACTACTTGTCAGATGTCCT
            CCATTCTCATGTTTTTATATATATTTATCTCCCCAAATAGTTGACAACAGTGGTTCCTGA

3069    TTGAGATGGAGTCTCGCTCTGTCACCAGGTTGGAGTGCAGTGGCGCGATCTTGGCTCACT
            GTAACCTCCGCCTCCCAGATTCAAGCAATTCCTCTTCCTCAGCCTCCCAAGTAGCTAGGA
            CTATAGGCATGCACCACCACGCCCGGCTAATTTTTTTTATTATTATTTTAGTAGAGATGG
            TGTTTCACCATGTTGGCCAGGATGGTCTCGATCTCCTGACCTTGTGATCCACCCACCTCA
            ACCTCCCAAAGTGCTGGGATTACAGGTGTGAGCCACTGTGCCCGGCCTATACATTTTTTT
            [C,G,A]
            AGGTTAAGTATACAATGGTGTCTCACACACATACATGCACACATATACACTGCATTCCAT
            AATATTCGGTTAATTGAGTTTTAATTATAGTGGTAGTTAATGCTTATTGAGTTCCTACTA
            TGTGCTGGGAATTACAGTTAGTGTTATGTGTGCATTATCTTTTTGCATTTATTGCAACAG
            TCCCATGGAGTATGAACCATTAGAATTCCTAATTTACAGATGCATGAACTGAAGCATAGG
            AGCAGTTTAACTAAATTTCTCAAGATTATACAGCTAGTTTATGTAATAGTGTTAGAACCA

3086    TCTGTCACCAGGTTGGAGTGCAGTGGCGCGATCTTGGCTCACTGTAACCTCCGCCTCCCA
            GATTCAAGCAATTCCTCTTCCTCAGCCTCCCAAGTAGCTAGGACTATAGGCATGCACCAC
            CACGCCCGGCTAATTTTTTTTATTATTATTTTAGTAGAGATGGTGTTTCACCATGTTGGC
            CAGGATGGTCTCGATCTCCTGACCTTGTGATCCACCCACCTCAACCTCCCAAAGTGCTGG
            GATTACAGGTGTGAGCCACTGTGCCCGGCCTATACATTTTTTTAAGGTTAAGTATACAAT
            [G,T]
            GTGTCTCACACACATACATGCACACATATACACTGCATTCCATAATATTCGGTTAATTGA
            GTTTTAATTATAGTGGTAGTTAATGCTTATTGAGTTCCTACTATGTGCTGGGAATTACAG
            TTAGTGTTATGTGTGCATTATCTTTTTGCATTTATTGCAACAGTCCCATGGAGTATGAAC
            CATTAGAATTCCTAATTTACAGATGCATGAACTGAAGCATAGGAGCAGTTTAACTAAATT
            TCTCAAGATTATACAGCTAGTTTATGTAATAGTGTTAGAACCAGTGTTAAAACTCAAACA

3104    TGCAGTGGCGCGATCTTGGCTCACTGTAACCTCCGCCTCCCAGATTCAAGCAATTCCTCT
            TCCTCAGCCTCCCAAGTAGCTAGGACTATAGGCATGCACCACCACGCCCGGCTAATTTTT
            TTTATTATTATTTTAGTAGAGATGGTGTTTCACCATGTTGGCCAGGATGGTCTCGATCTC
            CTGACCTTGTGATCCACCCACCTCAACCTCCCAAAGTGCTGGGATTACAGGTGTGAGCCA
            CTGTGCCCGGCCTATACATTTTTTTAAGGTTAAGTATACAATGGTGTCTCACACACATAC
            [A,G]
            TGCACACATATACACTGCATTCCATAATATTCGGTTAATTGAGTTTTAATTATAGTGGTA
            GTTAATGCTTATTGAGTTCCTACTATGTGCTGGGAATTACAGTTAGTGTTATGTGTGCAT
            TATCTTTTTGCATTTATTGCAACAGTCCCATGGAGTATGAACCATTAGAATTCCTAATTT
            ACAGATGCATGAACTGAAGCATAGGAGCAGTTTAACTAAATTTCTCAAGATTATACAGCT
            AGTTTATGTAATAGTGTTAGAACCAGTGTTAAAACTCAAACAGTGGGACCCAGGAGCTTT

3217    AATTTTTTTTATTATTATTTTAGTAGAGATGGTGTTTCACCATGTTGGCCAGGATGGTCT
            CGATCTCCTGACCTTGTGATCCACCCACCTCAACCTCCCAAAGTGCTGGGATTACAGGTG
            TGAGCCACTGTGCCCGGCCTATACATTTTTTTAAGGTTAAGTATACAATGGTGTCTCACA
            CACATACATGCACACATATACACTGCATTCCATAATATTCGGTTAATTGAGTTTTAATTA
            TAGTGGTAGTTAATGCTTATTGAGTTCCTACTATGTGCTGGGAATTACAGTTAGTGTTAT
            [G,A]
            TGTGCATTATCTTTTTGCATTTATTGCAACAGTCCCATGGAGTATGAACCATTAGAATTC
            CTAATTTACAGATGCATGAACTGAAGCATAGGAGCAGTTTAACTAAATTTCTCAAGATTA
            TACAGCTAGTTTATGTAATAGTGTTAGAACCAGTGTTAAAACTCAAACAGTGGGACCCAG
            GAGCTTTCTCCTAATGACTATGCTTTGTTTTTGCCCTATATTCTACCTGGGCATGTGATG
```

FIGURE 3G

```
        TTTGGCCTTCTCTCTTGCTCTTTTTTAAAGCAGCCCCTGATGCAAATGGTTCTCTCCTTC
3293    TGATCCACCCACCTCAACCTCCCAAAGTGCTGGGATTACAGGTGTGAGCCACTGTGCCCG
        GCCTATACATTTTTTTAAGGTTAAGTATACAATGGTGTCTCACACACATACATGCACACA
        TATACACTGCATTCCATAATATTCGGTTAATTGAGTTTTAATTATAGTGGTAGTTAATGC
        TTATTGAGTTCCTACTATGTGCTGGGAATTACAGTTAGTGTTATGTGTGCATTATCTTTT
        TGCATTTATTGCAACAGTCCCATGGAGTATGAACCATTAGAATTCCTAATTTACAGATGC
        [A,G]
        TGAACTGAAGCATAGGAGCAGTTTAACTAAATTTCTCAAGATTATACAGCTAGTTTATGT
        AATAGTGTTAGAACCAGTGTTAAAACTCAAACAGTGGGACCCAGGAGCTTTCTCCTAATG
        ACTATGCTTTGTTTTTGCCCTATATTCTACCTGGGCATGTGATGTTTGGCCTTCTCTCTT
        GCTCTTTTTTAAAGCAGCCCCTGATGCAAATGGTTCTCTCCTTCTCTCTGAGTGATAACA
        ATGGGCAAGAATAGTGAGGATGCTTAGAAGATATTTGCAGCTACAAATTTTCCAAAGAAT
3355    CTATACATTTTTTTAAGGTTAAGTATACAATGGTGTCTCACACACATACATGCACACATA
        TACACTGCATTCCATAATATTCGGTTAATTGAGTTTTAATTATAGTGGTAGTTAATGCTT
        ATTGAGTTCCTACTATGTGCTGGGAATTACAGTTAGTGTTATGTGTGCATTATCTTTTTG
        CATTTATTGCAACAGTCCCATGGAGTATGAACCATTAGAATTCCTAATTTACAGATGCAT
        GAACTGAAGCATAGGAGCAGTTTAACTAAATTTCTCAAGATTATACAGCTAGTTTATGTA
        [A,T]
        TAGTGTTAGAACCAGTGTTAAAACTCAAACAGTGGGACCCAGGAGCTTTCTCCTAATGAC
        TATGCTTTGTTTTTGCCCTATATTCTACCTGGGCATGTGATGTTTGGCCTTCTCTCTTGC
        TCTTTTTTAAAGCAGCCCCTGATGCAAATGGTTCTCTCCTTCTCTCTGAGTGATAACAAT
        GGGCAAGAATAGTGAGGATGCTTAGAAGATATTTGCAGCTACAAATTTTCCAAAGAATGT
        CTACATGTAACTACTGTATAGAGTAAGGATTCTTAACCAGGGGTTCGTATGTAGGCAACA
3371    GGTTAAGTATACAATGGTGTCTCACACACATACATGCACACATATACACTGCATTCCATA
        ATATTCGGTTAATTGAGTTTTAATTATAGTGGTAGTTAATGCTTATTGAGTTCCTACTAT
        GTGCTGGGAATTACAGTTAGTGTTATGTGTGCATTATCTTTTTGCATTTATTGCAACAGT
        CCCATGGAGTATGAACCATTAGAATTCCTAATTTACAGATGCATGAACTGAAGCATAGGA
        GCAGTTTAACTAAATTTCTCAAGATTATACAGCTAGTTTATGTAATAGTGTTAGAACCAG
        [T,G]
        GTTAAAACTCAAACAGTGGGACCCAGGAGCTTTCTCCTAATGACTATGCTTTGTTTTTGC
        CCTATATTCTACCTGGGCATGTGATGTTTGGCCTTCTCTCTTGCTCTTTTTTAAAGCAGC
        CCCTGATGCAAATGGTTCTCTCCTTCTCTCTGAGTGATAACAATGGGCAAGAATAGTGAG
        GATGCTTAGAAGATATTTGCAGCTACAAATTTTCCAAAGAATGTCTACATGTAACTACTG
        TATAGAGTAAGGATTCTTAACCAGGGGTTCGTATGTAGGCAACAAGATATCTGAAACTCC
3588    GATGCATGAACTGAAGCATAGGAGCAGTTTAACTAAATTTCTCAAGATTATACAGCTAGT
        TTATGTAATAGTGTTAGAACCAGTGTTAAAACTCAAACAGTGGGACCCAGGAGCTTTCTC
        CTAATGACTATGCTTTGTTTTTGCCCTATATTCTACCTGGGCATGTGATGTTTGGCCTTC
        TCTCTTGCTCTTTTTTAAAGCAGCCCCTGATGCAAATGGTTCTCTCCTTCTCTCTGAGTG
        ATAACAATGGGCAAGAATAGTGAGGATGCTTAGAAGATATTTGCAGCTACAAATTTTCCA
        [G,A]
        AGAATGTCTACATGTAACTACTGTATAGAGTAAGGATTCTTAACCAGGGGTTCGTATGTA
        GGCAACAAGATATCTGAAACTCCTGAAATTGAATGCAAAACCATGTTTTTGTATCCATTG
        TATATCCATTTTTATAGTTCTCCTCAAATTCACAGAGGGAACTTTAACCTGAAAATGTTA
        GGAATCAATGCTCTTGA
4320    TAAAGAGCTTGAGACACAAACTGCTGGGCCCAGTCCTCTGAGTTCCTGATTCAGTAGGTT
        TGGTTGGAATTTGCATATCTAACAGATTAGTCCAAGTGATGCTGATGCCTTTGTCCCAAG
        GCCCATACTTTGAGAACCATAATTCTATTCCGGTTTCCATATTAAGACAAAGAAAGTAAG
        GACTAGAGAGGGTTAGCAGATTTTTTCTAAGGTAACATGATTAGCTAGGGAAAAGCAAGGA
        CTTTCACTGTGTTTTACAGCATCAAGGAATCTACTCTTACTTTTGGATCATTGAGAATAT
        [G,A]
        GCCACAGAGAACTGAACCTAAAAGAAATTGTGCTTTTTCCATAGAGTGAAATCATCCAAC
        ATCAAGGCTATCCCTGTGAGGAATATGAAGTCGCAACTGAAGATGGGTATATCCTTTCTG
        TTAACAGGATTCCTCGAGGCCTAGTGCAACCTAAGAAGACAGGTGTGGGTCACCCCATGT
        CACCGCAACACAGCAGTCTTCTCTGCAGTCACGATTTCCTTGTGATTTGAATGTAGAAGA
        GAGCCTGGGTTCTTAGTGCAGAGTGAGGTCCATTGTTCAGGTCAAAGGATGGTGTCAGTT
4960    CTGCCACCAATTATCTCAATTAAACATACAGTGTTTGCTTTTCAAAACACTCCTTCAAGA
        AAAGTTCATTTCTTGACTTATTTTAGCGCTTAACCCATTCCCCAAAACTCCTCCTATGTA
        GACATTCTAAAATATTTACTGACAATTCCTTGAACAGACCATATCAACCTCTGATTATGA
        AGAATTCAAGCTTCTTTATGGCACCTGGTACCCGCTCCTGTATACTCTGTATTCCTCATC
        TAAAGAGCACTTAAAATATTTAAGATGTTGCCTAGCTTTTTACTAAGGGCTTTTGAAAAA
        [C,T]
        GAAAGTTCTATACATACATTTTATTTTATTTTATTTTATTTTATTTTATTTTATTTTATT
        TTTGAGGTGGAGTTTTGCACTTGTTGCCCAGGCTGGAGTGCAGTGGTAGGATCTCAGCTC
        ACCGCAACCTCCGCCTCCTGGGTTCAAGCAATTCTCCTGCTTCAGCCTCCCAAGTAGCTG
        GGATTACAGGCATACACCACCACACCTGGCTAATTTTTGTATTTTTGGTAGAGACAGAGT
        TTCTCCATGTTGGTCAGGCTGGTCTTGAACTCCCGACCTCAGGTGATCCACCCGCCTCCA
5722    TATGCCTATTTTTCATTTCTATTTGGCTGGATTCTTTTTAATACTCTAGCAGTAGGTTTA
        TAGTAGCAACTATATTGTCTTTCTTGTGTATAGGTAATATAATTTCTTGTGTTATTTTGA
        TATGCCAGATACACTGATAAGTGCTTTATTTTGTATTAGTCTCATTTAATTTTCACAATTA
        CCCTAAGAAACTGCTACTCACATATGTTAAGCAACTTGCCCAAAACGTCTGTGCTAGTGC
```

FIGURE 3H

```
               TTGCTAGTGAGTTGTAAAACCTGCACTCAAATCAAATCTGTCTCTCTGCCATTATAGCCC
               [G,A]
               TGTTCTTAACTAGGACCAGAAAATGCTGGACAAATGCTATTGGGCTTTGGTGTAAAGAAA
               CGTTGGGGTTCTGTTTTACTCCAATTTGTACTTGTGTAGCTTTTTGAAACCACCTTTTTT
               TTTCTCACTAGCTGCACAGCTGCGCCTTATACATGTCTAGCGTGCACCTGCCTTAGTGTC
               TTTGAACTTAAATTTCTCCCTCTGGACCACTGTTTCATCAGATGTCTATGCAGCTTGCCT
               TGGCCCTTCTTTCAGCCAACTTTATCAGAGTTCTTCCCTGGCCACCCTATTCAAAATTGC

6018      GCCCGTGTTCTTAACTAGGACCAGAAAATGCTGGACAAATGCTATTGGGCTTTGGTGTAA
               AGAAACGTTGGGGTTCTGTTTTACTCCAATTTGTACTTGTGTAGCTTTTTGAAACCACCT
               TTTTTTTTCTCACTAGCTGCACAGCTGCGCCTTATACATGTCTAGCGTGCACCTGCCTTA
               GTGTCTTTGAACTTAAATTTCTCCCTCTGGACCACTGTTTCATCAGATGTCTATGCAGCT
               TGCCTTGGCCCTTCTTTCAGCCAACTTTATCAGAGTTCTTCCCTGGCCACCCTATTCAAA
               [G,A]
               TTGCAGCTCTTTGCTACCTATTGAGTTCTAGCCCCTTACCCTGCTTACTTTTCCATATAG
               CACTTACCATCACCTGATATAATAGATATTTGCATGTTTGTCTATTGTCTGTCTCCCCCC
               AGTCAGAGTGTAAACTCAGTGAGAGCAGAGACATCATTTGTTTTGCTCAAGGCTAGAACC
               AGTAACTAAATGAGTGCTGAGCACATTCTGGTGCTAATAAATATTTGCGGGATGAATTAT
               AGATTTTGTATAAATAAATGAATAGCCTGGGGACACAGCCCCACGAATCTCAGGGGAGTG

6563      TTTGTATAAATAAATGAATAGCCTGGGGACACAGCCCCACGAATCTCAGGGGAGTGGTAA
               AAGCACAGTTCTTCCAAGCAGTCGAGTGACTTAGCAATTACTAAGCATGGGGGTCACCTG
               CAGCCCCTATTCTATGGATGGAATTTGTTTTCTTACATCCTGTTGATTCAGACTGTTCAC
               ACATTGCCCAGGTGTTTGAGGTTCAAGGAATCTGCCTCCTTGTTCCAGTCCGTGCAGAAT
               ACTTCCCTCTAGTGGCCAATGTTGTTGGCATGTGCCTCTTCAGAGGCAATCTCCCATATC
               [A,-]
               AAAAAAAAAAAAAAAATTCACCAACCAAGAAAGCCAATGAAATTCTTATTGAAAACAACT
               GAAAAATGTTTACTGTAAAGCTTATAGCTTGTGGTAGCGGCCTTTTTATCTTTATCAAAG
               AATCTTAGTTGGCTTCAATATCAAGAGAGAAAATAGGCTGGGCCATCCTCAGAAATGACA
               GCTGTGTAAGTGTAGCCCTTACACACTTACCTGCTGGGTGTAAATTAAATAGAAGACCTA
               GGGGATGTTTGAAATGATATAAATGAGCCATTCCTCTTGTTAGGGGAATCACAAGAACAA

6574      AAATGAATAGCCTGGGGACACAGCCCCACGAATCTCAGGGGAGTGGTAAAAGCACAGTTC
               TTCCAAGCAGTCGAGTGACTTAGCAATTACTAAGCATGGGGGTCACCTGCAGCCCCTATT
               CTATGGATGGAATTTGTTTTCTTACATCCTGTTGATTCAGACTGTTCACACATTGCCCAG
               GTGTTTGAGGTTCAAGGAATCTGCCTCCTTGTTCCAGTCCGTGCAGAATACTTCCCTCTA
               GTGGCCAATGTTGTTGGCATGTGCCTCTTCAGAGGCAATCTCCCATATCAAAAAAAAAAA
               [A,-]
               AAAAATTCACCAACCAAGAAAGCCAATGAAATTCTTATTGAAAACAACTGAAAAATGTTT
               ACTGTAAAGCTTATAGCTTGTGGTAGCGGCCTTTTTATCTTTATCAAAGAATCTTAGTTG
               GCTTCAATATCAAGAGAGAAAATAGGCTGGGCCATCCTCAGAAATGACAGCTGTGTAAGT
               GTAGCCCTTACACACTTACCTGCTGGGTGTAAATTAAATAGAAGACCTAGGGGATGTTTG
               AAATGATATAAATGAGCCATTCCTCTTGTTAGGGGAATCACAAGAACAAACTATATGACT

6600      CACGAATCTCAGGGGAGTGGTAAAAGCACAGTTCTTCCAAGCAGTCGAGTGACTTAGCAA
               TTACTAAGCATGGGGGTCACCTGCAGCCCCTATTCTATGGATGGAATTTGTTTTCTTACA
               TCCTGTTGATTCAGACTGTTCACACATTGCCCAGGTGTTTGAGGTTCAAGGAATCTGCCT
               CCTTGTTCCAGTCCGTGCAGAATACTTCCCTCTAGTGGCCAATGTTGTTGGCATGTGCCT
               CTTCAGAGGCAATCTCCCATATCAAAAAAAAAAAAAAAATTCACCAACCAAGAAAGCCA
               [G,A]
               TGAAATTCTTATTGAAAACAACTGAAAAATGTTTACTGTAAAGCTTATAGCTTGTGGTAG
               CGGCCTTTTTATCTTTATCAAAGAATCTTAGTTGGCTTCAATATCAAGAGAGAAAATAGG
               CTGGGCCATCCTCAGAAATGACAGCTGTGTAAGTGTAGCCCTTACACACTTACCTGCTGG
               GTGTAAATTAAATAGAAGACCTAGGGGATGTTTGAAATGATATAAATGAGCCATTCCTCT
               TGTTAGGGGAATCACAAGAACAAACTATATGACTAAGTAGAACCAAGGTGACCTTAACCA

10518      CACTTCAGCATCTTTACAACTATTCCTGTAAATGAATCTGCAGAGCCCTGTGCGGTTCTG
               CTTAACAGTAGAACAGGACACTTCCACTAGCAGTTGCGTTATGTGCTCAGTAAATATTCA
               CTGAAGATAGTTATTGCTACGTGATAACATCTAGAGAAAACAGCAGTTTGCTGACAGCCT
               GTGACTCCAGAGGCACCCATGCTTCATAGGTTTGAAAGAAATCCATTCTGAGTGTTGTGA
               GGGACACGGTAACAAGCTGTCAGAGTTGACAACTCAAGGGCTTGTTTGTAAACCTGGTGT
               [G,C]
               GGGGGGAGCTTTTGTTTGTTTCTGATTATAATTTTTTCATATAACTTTGTCTTTTCCCCTT
               GTAGTTATGATGAGATGGCTAGGTTTGACCTTCCTGCAGTGATAAACTTTATTTTGCAGA
               AAACGGGCCAGGAAAAGATCTATTATGTCGGCTATTCACAGGGCACCACCATGGGTAGGT
               TCAAAGAAAGCAGGTTTGTATACTCGGAAGAAATGTGAGCATACGACACTAGCTATCCC
               TGAAATCTGTCACCTTGTGCTTCCTTCAGACCTGCTCTTTTCATCTTCAGAATCATGTAG

10857      TATAACTTTGTCTTTTCCCCTTGTAGTTATGATGAGATGGCTAGGTTTGACCTTCCTGCA
               GTGATAAACTTTATTTTGCAGAAAACGGGCCAGGAAAAGATCTATTATGTCGGCTATTCA
               CAGGGCACCACCATGGGTAGGTTCAAAGAAAAGCAGGTTTGTATACTCGGAAGAAATGTG
               AGCATACGACACTAGCTATCCCTGAAATCTGTCACCTTGTGCTTCCTTCAGACCTGCTCT
               TTTCATCTTCAGAATCATGTAGTCCCCAGCAATGTGTCTAGCATATAGACATATGTGCTA
               [G,C]
               ATATAGCATATCTCTGTGCTATATGTGTCTAGATATAGCATATCTCTCAATATAAATATT
               TTCTCAAAGCCAACATCGTGTTATTCAATTATTTATTTAACTCATTGAGCACCTACTACT
               TGAAAGCAAATATGCTGGTGTCATAAGGACCTTATAATTTTATAGGAGAGGTAAGATGCA
```

FIGURE 3I

```
         GTCACATATATACTTATTGAAATATGTATTTAAAAGCAAAATATACATTTTATGAGTTCT
         AAAAATATTTCGTATTCATGTTGACATATTTCTTCTTTTGCAGGCTTTATTGCATTTTCC

11109    AATCATGTAGTCCCCAGCAATGTGTCTAGCATATAGACATATGTGCTAGATATAGCATAT
         CTCTGTGCTATATGTGTCTAGATATAGCATATCTCTCAATATAAATATTTTCTCAAAGCC
         AACATCGTGTTATTCAATTATTTATTTAACTCATTGAGCACCTACTACTTGAAAGCAAAT
         ATGCTGGTGTCATAAGGACCTTATAATTTTATAGGAGAGGTAAGATGCAGTCACATATAT
         ACTTATTGAAATATGTATTTAAAAGCAAAATATACATTTTATGAGTTCTAAAAATATTTC
         [G,A]
         TATTCATGTTGACATATTTCTTCTTTTGCAGGCTTTATTGCATTTTCCACCATGCCAGAG
         CTGGCTCAGAAAATCAAAATGTATTTTGCTTTAGCACCCATAGCCACTGTTAAGCATGCA
         AAAAGCCCCGGGACCAAATTTTTGTTGCTGCCAGATATGATGATCAAGGTATGAGACTCC
         TCAGAAAACTTCCTGTGTACGTAGAAAAATCTTCCAGCCCAATTTCCTAAAACATAAACT
         TTTAAATTACAGTCACATCTTTTCTGTCTGTCATGTCTATGTCACTTCATATTTTCACAG

13112    GGGTATACATCTTGTGAGTTTTTCTATGTCCCCCAGAATACTCATGGTTTGTTACAGAGC
         CGAGCAAGTGTATATGCTGCCCACACTCTTGCTGGAACATCTGTGCAAAATATTCTACAC
         TGGAGCCAGGTAAGAATGTTGAATTTGCAGTCTTTGCTAAATGTCCTGTTATATTTTGTG
         TAGAATAGTCAAAGGACACCATTTAGATAAGCCAGGGATTATTTCACACTTATTCTAAGA
         TGAAATGCAGTATCGTCGATGCTATTTTGATGGAGAATTTGATCTAGATCACTGAAACTT
         [C,T]
         TCAAGAAATGGGAAGAAAGGACAGAAGTAGCCTAAGAACTTCTTTAGATCTTAAAAGTAT
         GAATTTAGATGATCCAAGTGAGACTTCTCTCTGTCTCTAGACACCTCAAAGATGTGGCTG
         GAGATAATTATGTTTCTACATCTTCTCTTCAGCTCCTCCAACAATACAGTCAAGTAGAAA
         CAAAAATGCTAATGTGGGGTCTGTCAAAAGAGATATTCACAGGAGTCCTTCACACTGCAA
         ACTTTACCTGCAATTACAGGAAACACACACCTCTGTGTGTCTATGTGGTGTGTGTGAAAG

15905    TCAAGGGCTCAGCCGGCTAGGCTAATTCTACTAACACTGCATAAATACGGAAAGTTCCCA
         GGTATTAGGAATACTAATTGGTATATTTGGTGGGGAAGGGTGAGGAATAAGGATTGGAGC
         AGGTATTTAACTTTTACTTCCCTTTAGCTCAAATTACCTGAGTGCCATAGGCCATGGTTC
         TGGCAAATGCAGTCAAGCCGGGTCTGCCTCAAAGGCTGCCTGGGATCACATAAAGACTGT
         GAAGATGCAGAGCCCTTCCCAGCAGATTCCTTGCTTTTCTCTGTGGAATATAATTCTTCT
         [T,C]
         TCATGAAATGTTTGTGAAATTATCTTTTAAAAGAACAGGGGCATTATTTTTAAAAACAAT
         TTGTTTACAAAATATTTAATAGGAAGAAAAAAGAAATACAAGGCATTACATGTTTTTATG
         TGTTTTGTCATTTGATCTAGCAAGTTATTACAGATATTATCCCCAGTCACAGAAGAAGAA
         ACTGAGGTTCAATAATGTTAAGTAATTTTACCTTAAAGTAAGGGCGGGAACAGAAATTCT
         TAACAGAGTTGTGTGGCTCTAACACCCATGTACCCTTCACCACAACAGATGGCATGTTTA

15968    ATTAGGAATACTAATTGGTATATTTGGTGGGGAAGGGTGAGGAATAAGGATTGGAGCAGG
         TATTTAACTTTTACTTCCCTTTAGCTCAAATTACCTGAGTGCCATAGGCCATGGTTCTGG
         CAAATGCAGTCAAGCCGGGTCTGCCTCAAAGGCTGCCTGGGATCACATAAAGACTGTGAA
         GATGCAGAGCCCTTCCCAGCAGATTCCTTGCTTTTCTCTGTGGAATATAATTCTTCTTTC
         ATGAAATGTTTGTGAAATTATCTTTTAAAAGAACAGGGGCATTATTTTTAAAAACAATTT
         [G,A]
         TTTACAAAATATTTAATAGGAAGAAAAAAGAAATACAAGGCATTACATGTTTTTATGTGT
         TTTGTCATTTGATCTAGCAAGTTATTACAGATATTATCCCCAGTCACAGAAGAAGAAACT
         GAGGTTCAATAATGTTAAGTAATTTTACCTTAAAGTAAGGGCGGGAACAGAAATTCTTAA
         CAGAGTTGTGTGGCTCTAACACCCATGTACCCTTCACCACAACAGATGGCATGTTTATTA
         TGTCTATTTGAAACATAAATTATGAGCCTGAAAGTCCAAATGTTACCTAGAGTTAAGAAC

16626    TACAGCAATGTGGACAGGAGGTCAGGACTGGCTTTCAAATCCAGAAGACGTGAAAATGCT
         GCTCTCTGAGGTGACCAACCTCATCTACCATAAGAATATTCCTGAATGGGCTCATGTGGA
         TTTCATCTGGGGTTTGGATGCTCCTCACCGTATGTACAATGAAATCATCCATCTGATGCA
         GCAGGAGGAGACCAACCTTTCCCAGGGACGGTGTGAGGCCGTATTGTGAAGCATCTGACA
         CTGACGATCTTAGGACAACCTCCTGAGGGATGGGGCTAGGACCCATGAAGGCAGAATTAC
         [G,A]
         GAGAGCAGAGACCTAGTATACATTTTTCAGATTCCCTGCACTTGGCACTAAATCCGACAC
         TTACATTTACATTTTTTTTCTGTAAATTAAAGTACTTATTAGGTAAATAGAGGTTTTGTA
         TGCTATTATATATTCTACCATCTTGAAGGGTAGGTTTTACCTGATAGCCAGAAAATATCT
         AGACATTCTCTATATCATTCAGGTAAATCTCTTTAAAACACCTATTGTTTTTTCTATAAG
         CCATATTTTTGGAGCACTAAAGTAAAATGGCAAATTGGGACAGATATTGAGGTCTGGAGT

Chromosome map:
Chromosome 10
```

FIGURE 3J

ISOLATED HUMAN LIPASE PROTEINS, NUCLEIC ACID MOLECULES ENCODING HUMAN LIPASE PROTEINS, AND USES THEREOF

FIELD OF THE INVENTION

The present invention is in the field of lipase proteins that are related to the lysosomal acid lipase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Lipases

The lipases comprise a family of enzymes with the capacity to catalyze hydrolysis of compounds including phospholipids, mono-, di-, and triglycerides, and acyl-coa thioesters. Lipases play important roles in lipid digestion and metabolism. Different lipases are distinguished by their substrate specificity, tissue distribution and subcellular localization.

Lipases have an important role in digestion. Triglycerides make up the predominant type of lipid in the human diet. Prior to absorption in the small intestine, triglycerides are broken down to monoglycerides and free fatty acids to allow solubilization and emulsification before micelle formation in conjunction with bile acids and phospholipids secreted by the liver. Secreted lipases that act within the lumen include lingual, gastric and pancreatic lipases, each having the ability to act under appropriate pH conditions. Modulating the activity of these enzymes has the potential to alter the processing and absorption of dietary fats. This may be important in the treatment of obesity or malabsorption syndromes such as those that occur in the presence of pancreatic insufficiency.

Lipases have an important role in lipid transport and lipoprotein metabolism. Subsequent to absorption across the intestinal mucosa, fatty acids are transported in complexes with cholesterol and protein molecules termed apoliporoteins. These complexes include particles known as chylomicrons, very low density lipoproteins ("VLDLs"), low density lipoproteins ("LDLs") and high density lipoproteins ("HDLs") depending upon their particular forms. Lipoprotein lipase and hepatic lipase are bound to act at the endothelial surfaces of extrahepatic and hepatic tissues, respectively. Deficiencies of these enzymes are associated with pathological levels of circulating lipoprotein particles. Lipoprotein lipase functions as a homodimer and has the dual functions of triglyceride hydrolase and ligand/bridging factor for receptor-mediated lipoprotein uptake. Severe mutations that cause LPL deficiency result in type I hyperlipoproteinemia, while less extreme mutations in LPL are linked to many disorders of lipoprotein metabolism.

Lipases have an important role in lipolysis. Free fatty acids derived from adipose tissue triglycerides are the most important fuel in mammals, providing more than half the caloric needs during fasting. The enzyme hormone-sensitive lipase plays a vital role in the mobilization of free fatty acids from adipose tissue by controlling the rate of lipolysis of stored triglycerides. Hormone sensitive lipase is activated by catecholamines through cyclic AMP-mediated phosphorylation of serine-563. Dephosphorylation is induced by insulin. While mice with homozygous-null mutations of their hormone-sensitive lipase genes induced by homologous recombination have been shown to enlarged adipocytes in their brown adipose tissue and to a lesser extent their white adipose tissue, they are not obese. White adipose tissue from homozygous null mice retain 40% of their wild type triacylglycerol lipase activity suggesting that one or more other, as yet uncharacterized, enzymes also mediate the hydrolysis of triglycerides stored in adipocytes. Hormone-sensitive lipase does not show sequence homology to the other characterized mammalian lipase proteins.

As identified above and in the cited references, lipase proteins are a major target for drug action and development. Accordingly, it is valuable to the field of pharmaceutical development to identify and characterize previously unknown members of the lipase family of proteins. The present invention advances the state of the art by providing previously unidentified human proteins that have homology to known members of the lipase family of proteins.

Lysosomal acid lipase (LAL) hydrolyzes cholesteryl esters and triglycerides that are delivered to the lysosomes by low density lipoprotein receptor-mediated endocytosis.

Molecular cloning of a full-length cDNA for human lysosomal acid lipase/cholesteryl ester hydrolase (EC 3.1.1.13) reveals that it is structurally related to previously described enteric acid lipases, but lacks significant homology with any characterized neutral lipases.

Its amino acid sequence, as deduced from the 2.6-kilobase cDNA nucleotide sequence, is 58 and 57% identical to those of human gastric lipase and rat lingual lipase, respectively, both of which are involved in the preduodenal breakdown of ingested triglycerides. Notable differences in the primary structure of the lysosomal lipase that may account for discrete catalytic and transport properties include the presence of 3 new cysteine residues, in addition to the 3 that are conserved in this lipase gene family, and of two additional potential N-linked glycosylation sites.

The human LAL cDNA and chromosomal gene have been characterized, and the locus maps to human chromosome 10q23.2-23.3(3, 4). The gene has 10 exons spread over 36 kilobase pairs. Several hLAL mutations have been detected in cDNAs derived from mRNAs of CESD and WD patient cells. In CESD, a splice donor site G to A transition leads to aberrant splicing of exon 8 and a 72-base pair (24-amino acid) deletion. An AG deletion leads to frameshift at amino acid 302 (AG302) and a truncated lipase with a 34-amino acid C-terminal deletion. Two proline to leucine substitutions (L179P and L336P) have been detected in different CESD patients. In WD, a T insertion at nucleotide 635 results in a frameshift (fs177) and premature translation termination at amino acid 189.

Deficient activity of lysosomal acid lipase (LAL) is associated with two autosomal recessive traits which expressed as two major phenotypes: Wolman disease and cholesterol ester storage disease (CESD). Wolman disease occurs in infancy and is nearly always fatal before the age of 1 year. Hepatosplenomegaly, steatorrhea, abdominal distension, adrenal calcification, and failure to thrive are observed in the first weeks of life. On the other hand, CESD has a more benign clinical course. CESD may not be detected until adulthood, and moderate hyperbetalipoproteinemia, hypertriglyceridemia, and hepatomegaly may be the only clinical signs. In addition, low plasma HDL cholesterol (HDL-C) and premature atherosclerosis occur in most cases with CESD. The enzymatic defect has been demonstrated in several types of cells and tissues, including liver, spleen, lymph nodes, aorta, peripheral blood leukocytes, and cultured skin fibroblasts. Higher residual activity of LAL in intact fibroblasts was found from patients with CESD than in those with Wolman disease, providing a biochemical explanation for the less severe phenotype associated with CESD.

Anderson et al., Proc. Nat. Acad. Sci. 91: 2718–2722, 1994; Anderson et al., Genomics 15: 245–247, 1993; Anderson et al., J. Biol. Chem. 266: 22479–22484, 1991; Aslanidis et al., Genomics 20: 329–331, 1994; Aslanidis et al., Genomics 33: 85–93, 1996; Assmann et al., Metabolic Basis of Inherited Disease. New York: McGraw-Hill (pub.) (5th ed.) 1983. Pp. 803–819; Beaudet et al., J. Pediat. 90: 910–914, 1977; Besley et al., Clin. Genet. 26: 195–203, 1984; Burton et al., Am. J. Hum. Genet. 33: 203–208, 1981; Byrd et al., Acta Neuropath. 45: 37–42, 1979; Cagle et al., Am. J. Med. Genet. 24: 711–722, 1986; Chatterjee et al., Clin. Genet. 29: 360–368, 1986; Christomanou et al., Hum. Genet. 57: 440–441, 1981; Coates et al., Am. J. Med. Genet. 2: 397–407, 1978; Crocker et al., Pediatrics 35: 627–640, 1965; Desai et al., Am. J. Med. Genet. 26: 689–698, 1987; Di Bisceglie et al., Hepatology 11: 764–772, 1990; Du et al., Hum. Molec. Genet. 7: 1347–1354, 1998; Fujiyama et al., Hum. Mutat. 8: 377–380, 1996; Hoeg et al., Am. J. Hum. Genet. 36: 1190–1203, 1984; Kahana et al., Pediatrics 42: 70–76, 1968.; Klima et al., J. Clin. Invest. 92: 2713–2718, 1993; Koch et al., Somat. Cell Genet. 7: 345–358, 1981; Koch et al., Cell Genet. 25: 174, 1979; Konno et al., Tohoku J. Exp. Med. 90: 375–389, 1966; Lake et al., J. Clin. Path. 24: 617–620, 1971; Lake et al., J. Pediat. 76: 262–266, 1970; Lough et al., Arch. Path. 89: 103–110, 1970; Marshall et al., Arch. Dis. Child. 44: 331–341, 1969; Maslen et al., Am. J. Hum. Genet. 53 (suppl.): A926, 1993; Muntoni et al., Hum. Genet. 95: 491–494, 1995; Muntoni et al., Hum. Genet. 97: 265–267, 1996; Pagani et al., Hum. Molec. Genet. 5: 1611–1617, 1996; Patrick et al., Nature 222: 1067–1068, 1969; Roytta et al., Clin. Genet. 42: 1–7, 1992; Schaub et al., Europ. J. Pediat. 135: 45–53, 1980; Schiff et al., Am. J. Med. 44: 538–546, 1968; Schmitz et al., The Metabolic Basis of Inherited Disease. New York: McGraw-Hill (pub.) (6th ed.) 1989. Pp. 1623–1644; Sloan et al., J. Clin. Invest. 51: 1923–1926, 1972; Spiegel-Adolf et al., Confin. Neurol. 28: 399–406, 1966; Wolman et al., Pediatrics 28: 742–757, 1961; Yokoyama et al., Metab. Dis. 15: 291–292, 1992; Yoshida et al., Lab. Animal Sci. 40: 486–489, 1990; Young et al., Arch. Dis. Child. 45: 664–668, 1970.

Lipase proteins, particularly members of the lysosomal acid lipase subfamily, are a major target for drug action and development. Accordingly, it is valuable to the field of pharmaceutical development to identify and characterize previously unknown members of this subfamily of lipase proteins. The present invention advances the state of the art by providing a previously unidentified human lipase proteins that have homology to members of the lysosomal acid lipase subfamily.

SUMMARY OF THE INVENTION

The present invention is based in part on the identification of amino acid sequences of human lipase peptides and proteins that are related to the lysosomal acid lipase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate lipase activity in cells and tissues that express the lipase. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte.

DESCRIPTION OF THE FIGURE SHEETS

FIG. 1 (e.g. FIGS. 1A–1B) provides the nucleotide sequence of a cDNA molecule or transcript sequence that encodes the lipase protein of the present invention. (SEQ ID NO:1). In addition, structure and functional information is provided, such as ATG start, stop and tissue distribution, where available, that allows one to readily determine specific uses of inventions based on this molecular sequence. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte.

FIG. 2 (e.g. FIGS. 2A–2B) provides the predicted amino acid sequence of the lipase of the present invention. (SEQ ID NO:2) In addition structure and functional information such as protein family, function, and modification sites is provided where available, allowing one to readily determine specific uses of inventions based on this molecular sequence.

FIG. 3 (e.g. FIGS. 3A–3J) provides genomic sequences that span the gene encoding the lipase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, including insertion/deletion variants ("indels"), were identified at 27 different nucleotide positions as set forth in SEQ ID NOS:5–30.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a lipase protein or part of a lipase protein and are related to the lysosomal acid lipase subfamily. Utilizing these sequences, additional genomic sequences were assembled and transcript and/or cDNA sequences were isolated and characterized. Based on this analysis, the present invention provides amino acid sequences of human lipase peptides and proteins that are related to the lysosomal acid lipase subfamily, nucleic acid sequences in the form of transcript sequences, cDNA sequences and/or genomic sequences that encode these lipase peptides and proteins, nucleic acid variation (allelic information), tissue distribution of expression, and information about the closest art known protein/peptide/domain that has structural or sequence homology to the lipase of the present invention.

In addition to being previously unknown, the peptides that are provided in the present invention are selected based on their ability to be used for the development of commercially important products and services. Specifically, the present peptides are selected based on homology and/or structural relatedness to known lipase proteins of the lysosomal acid lipase subfamily and the expression pattern observed. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known lysosomal acid lipase family or subfamily of lipase proteins.

Specific Embodiments

Peptide Molecules

The present invention provides nucleic acid sequences that encode protein molecules that have been identified as being members of the lipase family of proteins and are related to the lysosomal acid lipase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the lipase peptides of the present invention, lipase peptides, or peptides/proteins of the present invention.

The present invention provides isolated peptide and protein molecules that consist of, consist essentially of, or comprise the amino acid sequences of the lipase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the lipase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated lipase peptide can be purified from cells that naturally express it, purified from cells that have been altered to express it (recombinant), or synthesized using known protein synthesis methods. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. For example, a nucleic acid molecule encoding the lipase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the lipase peptides of the present invention are the naturally occurring mature proteins. A brief description of how various types of these proteins can be made/isolated is provided below.

The lipase peptides of the present invention can be attached to heterologous sequences to form chimeric or fusion proteins. Such chimeric and fusion proteins comprise a lipase peptide operatively linked to a heterologous protein having an amino acid sequence not substantially homologous to the lipase peptide. "Operatively linked" indicates that the lipase peptide and the heterologous protein are fused in-frame. The heterologous protein can be fused to the N-terminus or C-terminus of the lipase peptide.

In some uses, the fusion protein does not affect the activity of the lipase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant lipase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A lipase peptide-encoding nucleic acid can be cloned into such an expression vector such that the fusion moiety is linked in-frame to the lipase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the lipase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al, *Nucleic Acids Res.* 12(1):387 (1984)) using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the lipase peptides of the present invention as well as being encoded by the same genetic locus as the lipase peptide provided herein. As indicated by the data presented in FIG. 3, the map position was determined to be on chromosome 10 by ePCR.

Allelic variants of a lipase peptide can readily be identified as being a human protein having a high degree (significant) of sequence homology/identity to at least a portion of the lipase peptide as well as being encoded by the same genetic locus as the lipase peptide provided herein. Genetic locus can readily be determined based on the genomic information provided in FIG. 3, such as the genomic sequence mapped to the reference human. As indicated by the data presented in FIG. 3, the map position was determined to be on chromosome 10 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a lipase peptide encoding nucleic acid molecule under stringent conditions as more fully described below.

FIG. 3 provides information on SNPs that have been found in the gene encoding the transporter protein of the present invention. SNPs were identified at 27 different nucleotide positions in introns and regions 5' and 3' of the ORF. Such SNPs in introns and outside the ORF may affect control/regulatory elements.

Paralogs of a lipase peptide can readily be identified as having some degree of significant sequence homology/identity to at least a portion of the lipase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a lipase peptide encoding nucleic acid molecule under moderate to stringent conditions as more fully described below.

Orthologs of a lipase peptide can readily be identified as having some degree of significant sequence homology/identity to at least a portion of the lipase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a lipase peptide encoding nucleic acid molecule under moderate to stringent conditions, as more fully described below, depending on the degree of relatedness of the two organisms yielding the proteins.

Non-naturally occurring variants of the lipase peptides of the present invention can readily be generated using recombinant techniques. Such variants include, but are not limited to deletions, additions and substitutions in the amino acid sequence of the lipase peptide. For example, one class of substitutions are conserved amino acid substitution. Such substitutions are those that substitute a given amino acid in a lipase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant lipase peptides can be fully functional or can lack function in one or more activities, e.g. ability to bind substrate, ability to hydrolyze substrate, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al, *Science* 244:1081–1085 (1989)), particularly using the results provided in FIG. 2. The latter procedure introduces single alanine mutations at every residue in the molecule. The resulting mutant molecules are then tested for biological activity such as lipase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the lipase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a lipase peptide. Such fragments can be chosen based on the ability to retain one or more of the biological activities of the lipase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the lipase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in lipase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N. Y Acad. Sci* 663:48–62 (1992)).

Accordingly, the lipase peptides of the present invention also encompass derivatives or analogs in which a substituted amino acid residue is not one encoded by the genetic code, in which a substituent group is included, in which the mature lipase peptide is fused with another compound, such as a compound to increase the half-life of the lipase peptide (for example, polyethylene glycol), or in which the additional amino acids are fused to the mature lipase peptide, such as a leader or secretory sequence or a sequence for purification of the mature lipase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a lipase-effector protein interaction or lipase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, lipases isolated from humans and their human/mammalian orthologs serve as targets for identifying agents for use in mammalian therapeutic applications, e.g. a human drug, particularly in modulating a biological or pathological response in a cell or tissue that expresses the lipase. Experimental data as provided in FIG. 1 indicaetes that lipase proteins of the present invention are expressed in the the colon tumor, colon, kidney renal cell adenocarcinoma, placenta, teratocarcinoma, skin melanotic melanom, B cell from burkitt's lymphoma by a virtual northern blot. In addition, PCR-based tissue screening panel indicates expression in mixed pool tissues of brain, heart, kidney, lung, spleen, testis, leukocyte. A large percentage of pharmaceutical agents are being developed that modulate the activity of lipase proteins, particularly members of the lysosomal acid lipase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. Such uses can readily be determined using the information provided herein, that which is known in the art, and routine experimentation.

The proteins of the present invention (including variants and fragments that may have been disclosed prior to the present invention) are useful for biological assays related to lipases that are related to members of the lysosomal acid lipase subfamily. Such assays involve any of the known lipase functions or activities or properties useful for diagnosis and treatment of lipase-related conditions that are specific for the subfamily of lipases that the one of the present invention belongs to, particularly in cells and tissues that express the lipase. Experimental data as provided in FIG. 1 indicates that lipase proteins of the present invention are expressed in the colon tumor, colon, kidney renal cell adenocarcinoma, placenta, teratocarcinoma, skin melanotic melanom, B cell from burkitt's lymphoma by a virtual northern blot. In addition, PCR-based tissue screening panel indicates expression in mixed pool tissues of brain, heart, kidney, lung, spleen, testis, leukocyte.

The proteins of the present invention are also useful in drug screening assays, in cell-based or cell-free systems. Cell-based systems can be native, i.e., cells that normally express the lipase, as a biopsy or expanded in cell culture. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. In an alternate embodiment, cell-based assays involve recombinant host cells expressing the lipase protein.

The polypeptides can be used to identify compounds that modulate lipase activity of the protein in its natural state or an altered form that causes a specific disease or pathology associated with the lipase. Both the lipases of the present invention and appropriate variants and fragments can be used in high-throughput screens to assay candidate compounds for the ability to bind to the lipase. These compounds can be further screened against a functional lipase to determine the effect of the compound on the lipase activity. Further, these compounds can be tested in animal or invertebrate systems to determine activity/effectiveness. Compounds can be identified that activate (agonist) or inactivate (antagonist) the lipase to a desired degree.

Further, the proteins of the present invention can be used to screen a compound for the ability to stimulate or inhibit interaction between the lipase protein and a molecule that normally interacts with the lipase protein, e.g. a substrate. Such assays typically include the steps of combining the lipase protein with a candidate compound under conditions that allow the lipase protein, or fragment, to interact with the target molecule, and to detect the formation of a complex between the protein and the target or to detect the biochemical consequence of the interaction with the lipase protein and the target, such as any of the associated effects of hydrolysis.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant lipases or appropriate fragments containing mutations that affect lipase function and thus compete for substrate. Accordingly, a fragment that competes for substrate, for example with a higher affinity, or a fragment that binds substrate but does not allow release, is encompassed by the invention.

Any of the biological or biochemical functions mediated by the lipase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the lipase can be assayed. Experimental data as provided in FIG. 1 indicates that lipase proteins of the present invention are expressed in the colon tumor, colon, kidney renal cell adenocarcinoma, placenta, teratocarcinoma, skin melanotic melanom, B cell from burkitt's lymphoma by a virtual northern blot. In addition, PCR-based tissue screening panel indicates expression in mixed pool tissues of brain, heart, kidney, lung, spleen, testis, leukocyte.

Binding and/or activating compounds can also be screened by using chimeric lipase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native lipase. Accordingly, a different set of signal transduction components is available as an end-point assay for activation. This allows for assays to be performed in other than the specific host cell from which the lipase is derived.

The proteins of the present invention are also useful in competition binding assays in methods designed to discover compounds that interact with the lipase (e.g. binding partners and/or ligands). Thus, a compound is exposed to a lipase polypeptide under conditions that allow the compound to bind or to otherwise interact with the polypeptide. Soluble lipase polypeptide is also added to the mixture. If the test compound interacts with the soluble lipase polypeptide, it decreases the amount of complex formed or activity from the lipase target. This type of assay is particularly useful in cases in which compounds are sought that interact with specific regions of the lipase. Thus, the soluble polypeptide that competes with the target lipase region is designed to contain peptide sequences corresponding to the region of interest.

To perform cell free drug screening assays, it is sometimes desirable to immobilize either the lipase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of lipase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a lipase-binding protein and a candidate compound are incubated in the lipase protein-presenting wells and the amount of complex trapped in the well can be quantitated. Methods for detecting such complexes, in addition to those described above for the GST-immobilized complexes, include immunodetection of complexes using antibodies reactive with the lipase protein target molecule, or which are reactive with lipase protein and compete with the target molecule, as well as enzyme-linked assays which rely on detecting an enzymatic activity associated with the target molecule.

Agents that modulate one of the lipases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of lipase protein activity identified according to these drug screening assays can be used to treat a subject with a disorder mediated by the lipase pathway, by treating cells or tissues that express the lipase. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. These methods of treatment include the steps of administering a modulator of lipase activity in a pharmaceutical composition to a subject in need of such treatment, the modulator being identified as described herein.

In yet another aspect of the invention, the lipase proteins can be used as "bait proteins" in a two-hybrid assay or three-hybrid assay (see, e.g., U.S. Pat. No. 5,283,317; Zervos et al. (1993) *Cell* 72:223–232; Madura et al (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the lipase and are involved in lipase activity.

The two-hybrid system is based on the modular nature of most transcription factors, which consist of separable DNA-binding and activation domains. Briefly, the assay utilizes two different DNA constructs. In one construct, the gene that codes for a lipase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a lipase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the lipase protein.

This invention further pertains to novel agents identified by the above-described screening assays. Accordingly, it is within the scope of this invention to further use an agent identified as described herein in an appropriate animal model. For example, an agent identified as described herein (e.g., a lipase-modulating agent, an antisense lipase nucleic acid molecule, a lipase-specific antibody, or a lipase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The lipase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. The method involves contacting a biological sample with a compound capable of interacting with the lipase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered lipase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the lipase protein in which one or more of the lipase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and lipase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. Accordingly, methods for treatment include the use of the lipase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the lipase proteins. Antibodies can be prepared from any region of the peptide as described herein. However, preferred regions will include those involved in function/activity and/or lipase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that lipase proteins of the present invention are expressed in the colon tumor, colon, kidney renal cell adenocarcinoma, placenta, teratocarcinoma, skin melanotic melanom, B cell from burkitt's lymphoma by a virtual northern blot. In addition, PCR-based tissue screening panel indicates expression in mixed pool tissues of brain, heart, kidney, lung, spleen, testis, leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. Thus, where a specific protein has been correlated with expression in a specific tissue, antibodies that are specific for this protein can be used to identify a tissue type.

The antibodies are also useful for inhibiting protein function, for example, blocking the binding of the lipase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a lipase peptide or protein of the present invention (cDNA, transcript and genomic sequence). Such nucleic acid molecules will consist of, consist essentially of, or comprise a nucleotide sequence that encodes one of the lipase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the lipase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the lipase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 10 by ePCR.

FIG. 3 provides information on SNPs that have been found in the gene encoding the transporter protein of the present invention. SNPs were identified at 27 different nucleotide positions in introns and regions 5' and 3' of the ORF. Such SNPs in introns and outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion variants ("indels"), were identified at 27 different nucleotide positions.

The probe can correspond to any sequence along the entire length of the nucleic acid molecules provided in the Figures. Accordingly, it could be derived from 5' noncoding regions, the coding region, and 3' noncoding regions.

However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 10 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that lipase proteins of the present invention are expressed in the the colon tumor, colon, kidney renal cell adenocarcinoma, placenta, teratocarcinoma, skin melanotic melanom, B cell from burkitt's lymphoma by a virtual northern blot. In addition, PCR-based tissue screening panel indicates expression in mixed pool tissues of brain, heart, kidney, lung, spleen, testis, leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in lipase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a lipase protein, such as by measuring a level of a lipase-encoding nucleic acid in a sample of cells from a subject e.g., mRNA or genomic DNA, or determining if a lipase gene has been mutated. Experimental data as provided in FIG. 1 indicates that lipase proteins of the present invention are expressed in the the colon tumor, colon, kidney renal cell adenocarcinoma, placenta, teratocarcinoma, skin melanotic melanom, B cell from burkitt's lymphoma by a virtual northern blot. In addition, PCR-based tissue screening panel indicates expression in mixed pool tissues of brain, heart, kidney, lung, spleen, testis, leukocyte.

Nucleic acid expression assays are useful for drug screening to identify compounds that modulate lipase nucleic acid expression.

The invention thus provides a method for identifying a compound that can be used to treat a disorder associated with nucleic acid expression of the lipase gene, particularly biological and pathological processes that are mediated by the lipase in cells and tissues that express it. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte. The method typically includes assaying the ability of the compound to modulate the expression of the lipase nucleic acid and thus identifying a compound that can be used to treat a disorder characterized by undesired lipase nucleic acid expression. The assays can be performed in cell-based and cell-free systems. Cell-based assays include cells naturally expressing the lipase nucleic acid or recombinant cells genetically engineered to express specific nucleic acid sequences.

The assay for lipase nucleic acid expression can involve direct assay of nucleic acid levels, such as mRNA levels. In this embodiment the regulatory regions of these genes can be operably linked to a reporter gene such as luciferase.

Thus, modulators of lipase gene expression can be identified in a method wherein a cell is contacted with a candidate compound and the expression of mRNA determined. The level of expression of lipase mRNA in the presence of the candidate compound is compared to the level of expression of lipase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate lipase nucleic acid expression in cells and tissues that express the lipase. Experimental data as provided in FIG. 1 indicates that lipase proteins of the present invention are expressed in the colon tumor, colon, kidney renal cell adenocarcinoma, placenta, teratocarcinoma, skin melanotic melanom, B cell from burkitt's lymphoma by a virtual northern blot. In addition, PCR-based tissue screening panel indicates expression in mixed pool tissues of brain, heart, kidney, lung, spleen, testis, leukocyte. Modulation includes both up-regulation (i.e. activation or agonization) or down-regulation (suppression or antagonization) or nucleic acid expression.

Alternatively, a modulator for lipase nucleic acid expression can be a small molecule or drug identified using the screening assays described herein as long as the drug or small molecule inhibits the lipase nucleic acid expression in the cells and tissues that express the protein. Experimental data as provided in FIG. 1 indicates expression in the colon tumor, colon, kidney renal cell adenocarcinoma, placenta, teratocarcinoma, skin melanotic melanom, B cell from burkitt's lymphoma and mixed pool tissues of brain, heart, kidney, lung, spleen, testis, leukocyte.

The nucleic acid molecules are also useful for monitoring the effectiveness of modulating compounds on the expression or activity of the lipase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in lipase nucleic acid expression, and particularly in qualitative changes that lead to pathology. The nucleic acid molecules can be used to detect mutations in lipase genes and gene expression products such as mRNA. The nucleic acid molecules can be used as hybridization probes to detect naturally occurring genetic mutations in the lipase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the lipase gene associated with a dysfunction provides a diagnostic tool for an active disease or susceptibility to disease when the disease results from overexpression, underexpression, or altered expression of a lipase protein.

Individuals carrying mutations in the lipase gene can be detected at the nucleic acid level by a variety of techniques. FIG. 3 provides information on SNPs that have been found in the gene encoding the transporter protein of the present invention. SNPs were identified at 27 different nucleotide positions in introns and regions 5' and 3' of the ORF. Such SNPs in introns and outside the ORF may affect control/regulatory elements. As indicated by the data presented in FIG. 3, the map position was determined to be on chromosome 10 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a lipase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant lipase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/161 01; Cohen et al, *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the lipase gene in an individual in order to select an appropriate compound or dosage regimen for treatment. FIG. 3 provides information on SNPs that have been found in the gene encoding the transporter protein of the present invention. SNPs were identified at 27 different nucleotide positions in introns and regions 5' and 3' of the ORF. Such SNPs in introns and outside the ORF may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control lipase gene expression in cells, tissues, and organisms. A DNA antisense nucleic acid molecule is designed to be complementary to a region of the gene involved in transcription, preventing transcription and hence production of lipase protein. An antisense RNA or DNA nucleic acid molecule would hybridize to the mRNA and thus block translation of mRNA into lipase protein.

Alternatively, a class of antisense molecules can be used to inactivate mRNA in order to decrease expression of lipase nucleic acid. Accordingly, these molecules can treat a disorder characterized by abnormal or undesired lipase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the lipase protein, such as substrate binding.

The nucleic acid molecules also provide vectors for gene therapy in patients containing cells that are aberrant in lipase gene expression. Thus, recombinant cells, which include the patient's cells that have been engineered ex vivo and returned to the patient, are introduced into an individual where the cells produce the desired lipase protein to treat the individual.

The invention also encompasses kits for detecting the presence of a lipase nucleic acid in a biological sample. Experimental data as provided in FIG. 1 indicates that lipase proteins of the present invention are expressed in the colon tumor, colon, kidney renal cell adenocarcinoma, placenta, teratocarcinoma, skin melanotic melanom, B cell from burkitt's lymphoma by a virtual northern blot. In addition, PCR-based tissue screening panel indicates expression in mixed pool tissues of brain, heart, kidney, lung, spleen, testis, leukocyte. For example, the kit can comprise reagents such as a labeled or labelable nucleic acid or agent capable of detecting lipase nucleic acid in a biological sample; means for determining the amount of lipase nucleic acid in the sample; and means for comparing the amount of lipase nucleic acid in the sample with a standard. The compound or agent can be packaged in a suitable container. The kit can further comprise instructions for using the kit to detect lipase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the lipase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the lipase gene of the present invention. FIG. 3 provides information on SNPs that have been found in the gene encoding the transporter protein of the present invention. SNPs were identified at 27 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al, *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified lipase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterolipase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed,* Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as lipases, appropriate secretion signals are incorporated into the vector. The signal sequence can be endogenous to the peptides or heterologous to these peptides.

Where the peptide is not secreted into the medium, which is typically the case with lipases, the protein can be isolated from the host cell by standard disruption procedures, including freeze thaw, sonication, mechanical disruption, use of lysing agents and the like. The peptide can then be recovered and purified by well-known purification methods including anunonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a lipase protein or peptide that can be further purified to produce desired amounts of lipase protein or fragments. Thus, host cells containing expression vectors are useful for peptide production.

Host cells are also useful for conducting cell-based assays involving the lipase protein or lipase protein fragments, such as those described above as well as other formats known in the art. Thus, a recombinant host cell expressing a native lipase protein is useful for assaying compounds that stimulate or inhibit lipase protein function.

Host cells are also useful for identifying lipase protein mutants in which these functions are affected. If the mutants naturally occur and give rise to a pathology, host cells containing the mutations are useful to assay compounds that have a desired effect on the mutant lipase protein (for example, stimulating or inhibiting function) which may not be indicated by their effect on the native lipase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a lipase protein and identifying and evaluating modulators of lipase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the lipase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the lipase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, and lipase protein activation, may not be evident from in vitro cell-free or cell-based assays. Accordingly, it is useful to provide non-human transgenic animals to assay in vivo lipase protein function, including substrate interaction, the effect of specific mutant lipase proteins on lipase protein function and substrate interaction, and the effect of chimeric lipase proteins. It is also possible to assess the effect of null mutations, that is mutations that substantially or completely eliminate one or more lipase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a protein comprising the amino acid sequence of SEQ ID NO:2;
   (b) a nucleotide sequence consisting of the nucleic acid sequence of SEQ ID No: 1; and
   (c) a nucleotide sequence that is completely complementary to a nucleotide sequence of (a) or (b).

2. A nucleic acid vector comprising the nucleic acid molecule of claim 1.

3. An isolated host cell containing the vector of claim 2.

4. A process for producing the protein of SEQ ID NO: 2 comprising culturing the host cell of claim 3 under conditions sufficient for the production of said protein, and recovering the protein from the host cell culture.

5. An isolated polynucleotide consisting of the nucleotide sequence set forth in SEQ ID NO:1.

6. The vector according to claim 2, wherein said vector is selected from the group consisting of a plasmid, virus, and bacteriophage.

7. The vector according to claim 2, wherein said isolated nucleic acid molecule is operatively linked to a promoter sequence such that the protein of SEQ ID NO: 2 is expressed by a cell transformed with said vector.

8. The vector according to claim 7, wherein said isolated nucleic acid molecule is operatively linked to a heterologous promoter sequence.

9. An isolated nucleic acid molecule comprising a nucleotide sequence selected from the group consisting of:
   (a) a nucleotide sequence that encodes a protein comprising the amino acid sequence of SEQ ID NO:2;
   (b) a nucleotide sequence comprising the nucleic acid sequence of SEQ ID No: 1; and
   c) a nucleotide sequence that is completely complementary to a nucleotide sequence of (a) or (b).

10. A nucleic acid vector comprising the nucleic acid molecule of claim 9.

11. An isolated host cell containing the vector of claim 10.

12. A process for producing the protein of SEQ ID NO: 2 comprising culturing the host cell of claim 11 under conditions sufficient for the production of said protein, and recovering the protein from the host cell culture.

13. An isolated polynucleotide comprising the nucleotide sequence set forth in SEQ ID NO:1.

14. The vector according to claim 10, wherein said vector is selected from the group consisting of a plasmid, virus, and bacteriophage.

15. The vector according to claim 10, wherein said isolated nucleic acid molecule is operatively linked to a promotor sequence such that the protein of SEQ ID NO: 2 is expressed by a cell transformed with said vector.

16. The vector according to claim 15, wherein said isolated nucleic acid molecule is operatively linked to a heterologous promotor sequence.

* * * * *

SEQUENCE LISTING

<160> NUMBER OF SEQ ID NOS: 30

<210> SEQ ID NO 1
<211> LENGTH: 1206
<212> TYPE: DNA
<213> ORGANISM: Homo Sapiens

<400> SEQUENCE: 1

```
tatatggagc taaaactgct cttcagagat gtcctacgtt gggctgagat gaccaggcct      60
ttagaccgca aacagagtga aatcatccaa catcaaggct atccctgtga ggaatatgaa     120
gtcgcaactg aagatgggta tatcctttct gttaacagga ttcctcgagg cctagtgcaa     180
cctaagaaga caggttccag gcctgtggtg ttactgcagc atggcctagt tggaggtgct     240
agcaactgga tttccaacct gcccaacaat agcctgggct tcattctggc agatgctggt     300
tttgacgtgt ggatggggaa cagcagggga aacgcctggt ctcgaaaaca caagacactc     360
tccatagacc aagatgagtt ctgggctttc agttatgatg agatggctag gtttgacctt     420
cctgcagtga taaactttat tttgcagaaa acgggccagg aaaagatcta ttatgtcggc     480
tattcacagg gcaccaccat gggctttatt gcattttcca ccatgccaga gctggctcag     540
aaaatcaaaa tgtattttgc tttagcaccc atagccactg ttaagcatgc aaaaagcccc     600
gggaccaaat ttttgttgct gccagatatg atgatcaagg gattgtttgg caaaaaagaa     660
tttctgtatc agaccagatt tctcagacaa cttgttattt acctttgtgg ccaggtgatt     720
cttgatcaga tttgtagtaa tatcatgtta cttctgggtg gattcaacac caacaatatg     780
aacatgagcc gagcaagtgt atatgctgcc cacactcttg ctggaacatc tgtgcaaaat     840
attctacact ggagccaggc agtgaattct ggtgaactcc gggcatttga ctgggggagt     900
```

```
gagaccaaaa atctggaaaa atgcaatcag ccaactcctg taaggtacag agtcagagat    960
atgacggtcc ctacagcaat gtggacagga ggtcaggact ggctttcaaa tccagaagac   1020
gtgaaaatgc tgctctctga ggtgaccaac ctcatctacc ataagaatat tcctgaatgg   1080
gctcacgtgg atttcatctg gggtttggat gctcctcacc gtatgtacaa tgaaatcatc   1140
catctgatgc agcaggagga gaccaacctt tcccagggac ggtgtgaggc cgtattgtga   1200
ataaag                                                              1206
```

<210> SEQ ID NO 2
<211> LENGTH: 398
<212> TYPE: PRT
<213> ORGANISM: Homo Sapiens

<400> SEQUENCE: 2

```
Met Glu Leu Lys Leu Leu Phe Arg Asp Val Leu Arg Trp Ala Glu Met
  1               5                  10                  15

Thr Arg Pro Leu Asp Arg Lys Gln Ser Glu Ile Ile Gln His Gln Gly
             20                  25                  30

Tyr Pro Cys Glu Glu Tyr Glu Val Ala Thr Glu Asp Gly Tyr Ile Leu
         35                  40                  45

Ser Val Asn Arg Ile Pro Arg Gly Leu Val Gln Pro Lys Lys Thr Gly
     50                  55                  60

Ser Arg Pro Val Val Leu Leu Gln His Gly Leu Val Gly Gly Ala Ser
 65                  70                  75                  80

Asn Trp Ile Ser Asn Leu Pro Asn Asn Ser Leu Gly Phe Ile Leu Ala
                 85                  90                  95

Asp Ala Gly Phe Asp Val Trp Met Gly Asn Ser Arg Gly Asn Ala Trp
            100                 105                 110

Ser Arg Lys His Lys Thr Leu Ser Ile Asp Gln Asp Glu Phe Trp Ala
        115                 120                 125

Phe Ser Tyr Asp Glu Met Ala Arg Phe Asp Leu Pro Ala Val Ile Asn
    130                 135                 140

Phe Ile Leu Gln Lys Thr Gly Gln Glu Lys Ile Tyr Tyr Val Gly Tyr
145                 150                 155                 160

Ser Gln Gly Thr Thr Met Gly Phe Ile Ala Phe Ser Thr Met Pro Glu
                165                 170                 175

Leu Ala Gln Lys Ile Lys Met Tyr Phe Ala Leu Ala Pro Ile Ala Thr
            180                 185                 190

Val Lys His Ala Lys Ser Pro Gly Thr Lys Phe Leu Leu Leu Pro Asp
        195                 200                 205

Met Met Ile Lys Gly Leu Phe Gly Lys Lys Glu Phe Leu Tyr Gln Thr
    210                 215                 220

Arg Phe Leu Arg Gln Leu Val Ile Tyr Leu Cys Gly Gln Val Ile Leu
225                 230                 235                 240

Asp Gln Ile Cys Ser Asn Ile Met Leu Leu Gly Gly Phe Asn Thr
                245                 250                 255

Asn Asn Met Asn Met Ser Arg Ala Ser Val Tyr Ala Ala His Thr Leu
            260                 265                 270

Ala Gly Thr Ser Val Gln Asn Ile Leu His Trp Ser Gln Ala Val Asn
        275                 280                 285

Ser Gly Glu Leu Arg Ala Phe Asp Trp Gly Ser Glu Thr Lys Asn Leu
    290                 295                 300

Glu Lys Cys Asn Gln Pro Thr Pro Val Arg Tyr Arg Val Arg Asp Met
```

|     |     |     |     |     |     |     |     |     |     |     |     |     |     |     |     |
| --- | --- | --- | --- | --- | --- | --- | --- | --- | --- | --- | --- | --- | --- | --- | --- |
| 305 |     |     |     |     | 310 |     |     |     |     | 315 |     |     |     |     | 320 |
| Thr | Val | Pro | Thr | Ala | Met | Trp | Thr | Gly | Gly | Gln | Asp | Trp | Leu | Ser | Asn |
|     |     |     |     | 325 |     |     |     |     | 330 |     |     |     |     | 335 |     |
| Pro | Glu | Asp | Val | Lys | Met | Leu | Leu | Ser | Glu | Val | Thr | Asn | Leu | Ile | Tyr |
|     |     |     | 340 |     |     |     |     | 345 |     |     |     |     | 350 |     |     |
| His | Lys | Asn | Ile | Pro | Glu | Trp | Ala | His | Val | Asp | Phe | Ile | Trp | Gly | Leu |
|     |     | 355 |     |     |     |     | 360 |     |     |     |     | 365 |     |     |     |
| Asp | Ala | Pro | His | Arg | Met | Tyr | Asn | Glu | Ile | Ile | His | Leu | Met | Gln | Gln |
|     | 370 |     |     |     |     | 375 |     |     |     |     | 380 |     |     |     |     |
| Glu | Glu | Thr | Asn | Leu | Ser | Gln | Gly | Arg | Cys | Glu | Ala | Val | Leu |     |     |
| 385 |     |     |     |     | 390 |     |     |     |     | 395 |     |     |     |     |     |

<210> SEQ ID NO 3
<211> LENGTH: 18554
<212> TYPE: DNA
<213> ORGANISM: Homo Sapiens

<400> SEQUENCE: 3

| agaggagagg | ctacctccag | atgagtaaga | cgatcatgtg | caatgttcat | gttccagaga | 60 |
| --- | --- | --- | --- | --- | --- | --- |
| tttatctaac | aaactctcag | aaaatggaac | tttaacatgt | atttataccg | atttaagacc | 120 |
| cttcctacag | aagcttcctt | atatgggttc | aaaaactgag | aggaaataga | aatattctgt | 180 |
| atctgcatgg | tgctgaatat | caggtttctt | ttgactattc | aatgattagg | tggtttgtct | 240 |
| aggtagttag | cacattggtg | tcagtcctca | ggagtcatcc | ttctggccct | gagactgtcc | 300 |
| cacttgaatt | cctctggttt | ggaggtgagg | ggaatctctg | cagtggcaga | cagagatgat | 360 |
| cttcctgggc | cccacccact | gcgtgtaccc | agcacctata | cactactggg | gcttcaggag | 420 |
| tctgtagact | aaagcccatt | gaattgggct | ctgcctttaa | gcagctatgc | ctggaaaaaa | 480 |
| acaaagtaaa | atagaaaatt | cgtacgattg | gtgtaaattc | aacaaaatag | aataaaagta | 540 |
| gttgcaagtt | tgaactggtt | ctgaggtagg | agaagggcag | gacttacttt | ctggtcccaa | 600 |
| caggatacag | tgaataaaca | agcacaaacc | agcaggtggt | gaaaaaaaaa | cagcaagaac | 660 |
| cagcagtggc | ctggaaggca | tcctttagtt | gccccggctg | ctcattagca | taagacactc | 720 |
| ctaccagaac | catgacagtt | tacaaatgtc | atagcaatga | cccacgagtt | agtaccctt | 780 |
| tccatggcaa | tggcccagaa | gttactgtcc | cgtttctgga | gatttctgaa | taacctgccc | 840 |
| cttaatttgc | atgaaattaa | tagttataag | taggcataaa | tacagctgcc | aatagcccat | 900 |
| acactgctga | ctctgggagc | actgcctatg | aattagctct | gcttttcaag | gagcagtacc | 960 |
| attcagtaaa | agattactgt | ctagtattac | cggctcgccc | ttgaattctt | tcctgggcaa | 1020 |
| agccaagaac | cttcccaggg | taagccccaa | ttttggagct | tgtctgtcct | gcattgattt | 1080 |
| gactctgtat | attcatgcat | atggattatg | gtctatctta | tactttgatg | aataactggc | 1140 |
| cttatgcatg | tattttttaa | gcaagtgttt | actgagcacc | tactaggtcc | atgatattgt | 1200 |
| gttatgtact | aaggttagac | agatctaaga | atattaaaag | ccctgacttt | atggagctta | 1260 |
| tagtccagca | ggaaggacag | atcatcaatt | agtcattata | aaagcaatga | aataaaagaa | 1320 |
| gaaaacataa | aataggggga | actaatccag | aaagctttgc | tgaagaaggg | tttcaaagcc | 1380 |
| tgaaatctga | aagataaatg | gcagttgctt | gagagggtgg | tagcaaaaag | gtcagcacat | 1440 |
| aggacagctg | gagcagctaa | gaacatgcca | gattcaagga | gctgaaagca | gcttatatct | 1500 |
| ggatggtctt | ttaaacattg | acttttttat | actattacaa | aagcaatata | tgctcattat | 1560 |
| agaaaattta | aaaaatacaa | aagaaggcaa | tagtcaccaa | tgtactctgc | accaagaact | 1620 |

-continued

```
gctttgtcat gcctttatct tcattctaaa tctgtgaggt tttgttttct taagaagaaa    1680
tgtcatgcac aatttactat tttccaactt tttttctgct aaacaatgta tatcatgaag    1740
aatttcccaa cgttttaaat acccttctac aacatcattt caccttgctg cattatgttc    1800
cattttttta aataagtatt tgccccaggt tggattttct ggggacaga ctctgaggca     1860 gaattcatac aataatgttt attaaggaga atcatcatca tcgcctgtgg aaaggaagta    1920
gagaatcagg agtaaggaaa gagataaatc aaactgtgat acagacttca aaacagccag    1980
actcaactcc atgaggagct atggagctaa aactgctctt cagagatgtc ctacgttggg    2040
ctgagatgac caggccttta gaccgcaaac aggtcagtca ctggatgtgg caggaaggga    2100
cgtgaacttg gaggaagtgg ctttctacag ctaaggccat tcctacagaa aatgacagcc    2160
aagggtgatc tgttgacagc acttccagtg gatgggacca gtcctttatt gcctgcataa    2220
attttcctgc caagtatagc atgttgacca tcttgccacc tgtagacaat gtttgcagca    2280
tttgtagttc ttttttcttct cagatgtcca tgtccctatc cctacctcct tggctctttt    2340
gagcaacttc tattcaatcc tcaaggccca gttcaaattc ttcctccata agaccttgcc    2400
tgtccagccc tgctcatttt gctcctcctg ctcagaattc ctttgctcct tccttcactc    2460
tcatccttca tccctcatct gacacattac acatatcctc tcaataacta cttgtcagat    2520
gtcctccatt ctcatgtttt tatatatatt tatctcccca aatagttgac aacagtggtt    2580
cctgaaggat agttgtcaga tcagcaacat ctgctttgcc tgggaacttg tatatcaatt    2640
ttttgggttc cacacagacc tgctgtatca gactgtgagt ggggtcccgc aatttgtgtt    2700
ttaacaaacc ctctaagtaa ttctgatgca tgctaaaatt tgagacactt ctataaattt    2760
ttttttcttt gagatggagt ctcgctctgt caccaggttg gagtgcagtg gcgcgatctt    2820
ggctcactgt aacctccgcc tcccagattc aagcaattcc tcttcctcag cctcccaagt    2880
agctaggact ataggcatgc accaccacgc ccggctaatt ttttttatta ttattttagt    2940
agagatggtg tttcaccatg ttggccagga tggtctcgat ctcctgacct tgtgatccac    3000
ccacctcaac ctcccaaagt gctgggatta caggtgtgag ccactgtgcc cggcctatac    3060 attttttaa ggttaagtat acaatggtgt ctcacacaca tacatgcaca catatacact     3120
gcattccata atattcggtt aattgagttt taattatagt ggtagttaat gcttattgag    3180
ttcctactat gtgctgggaa ttacagttag tgttatgtgt gcattatctt tttgcattta    3240
ttgcaacagt cccatggagt atgaaccatt agaattccta atttacagat gcatgaactg    3300
aagcatagga gcagtttaac taaatttctc aagattatac agctagttta tgtaatagtg    3360
ttagaaccag tgttaaaaact caaacagtgg gacccaggag cttctcccta atgactatgc    3420 tttgttttg ccctatattc tacctgggca tgtgatgttt ggccttctct cttgctcttt     3480
tttaaagcag cccctgatgc aaatggttct ctccttctct ctgagtgata acaatgggca    3540
agaatagtga ggatgcttag aagatatttg cagctacaaa ttttccaaag aatgtctaca    3600
tgtaactact gtatagagta aggattctta accaggggtt cgtatgtagg caacaagata    3660
tctgaaactc ctgaaattga atgcaaaacc atgttttttgt atccattgta tatccatttt    3720
tatagttctc ctcaaattca cagagggaac tttaacctga aaatgttagg aatcaatgct    3780
cttgagtctg tggttttaga actggaaaga accttaggaa atgcatggcc caggaatgct    3840
cataagttgt cctggaacag gtgccccact ggctgcttta gaaccatctt atctgtaacc    3900
tgaagtgggc tcaagactct gtatgtttca atgcccagaa gattctgatg cacaacgagg    3960
ttttggaatc aatgttctga tccagtggtt ctcaaacatt agggtacatc aaaattccct    4020
```

```
aaagagcttg agacacaaac tgctgggccc agtcctctga gttcctgatt cagtaggttt    4080
ggttggaatt tgcatatcta acagattagt ccaagtgatg ctgatgcctt tgtcccaagg    4140
cccatacttt gagaaccata attctattcc ggtttccata ttaagacaaa gaaagtaagg    4200
actagagagg gttagcagat ttttctaagg taacatgatt agctagggaa aagcaaggac    4260
tttcactgtg ttttacagca tcaaggaatc tactcttact tttggatcat tgagaatatg    4320
gccacagaga actgaaccta aagaaattg tgctttttcc atagagtgaa atcatccaac     4380
atcaaggcta tccctgtgag gaatatgaag tcgcaactga agatgggtat atcctttctg    4440
ttaacaggat cctcgaggc ctagtgcaac ctaagaagac aggtgtgggt caccccatgt     4500
caccgcaaca cagcagtctt ctctgcagtc acgatttcct tgtgatttga atgtagaaga    4560
gagcctgggt tcttagtgca gagtgaggtc cattgttcag gtcaaaggat ggtgtcagtt    4620
cccccatagt ctccatcacc accaccgtgt ccgtccccac tgccaccaat tatctcaatt    4680
aaacatacag tgtttgcttt tcaaaacact ccttcaagaa aagttcattt cttgacttat    4740
tttagcgctt aacccattcc ccaaaactcc tcctatgtag acattctaaa atatttactg    4800
acaattcctt gaacagacca tatcaacctc tgattatgaa gaattcaagc ttctttatgg    4860
cacctggtac ccgctcctgt atactctgta ttcctcatct aaagagcact taaaatattt    4920
aagatgttgc ctagcttttt actaagggct tttgaaaaac gaaagttcta tacatacatt    4980 ttatttatt ttatttatt ttatttatt ttatttatt tttgaggtgg agttttgcac         5040
ttgttgccca ggctggagtg cagtggtagg atctcagctc accgcaacct ccgcctcctg    5100
ggttcaagca attctcctgc ttcagcctcc caagtagctg ggattacagg catacaccac    5160
cacacctggc taatttttgt attttggta gagacagagt ttctccatgt tggtcaggct     5220
ggtcttgaac tccgacctc aggtgatcca cccgcctcca cctcccaaag tgctgggatt     5280
acaggcatga gccaccgcgc ctggctatac atacatttta aatgtttgat acatgtctcc    5340
atagttcata caattccacc cttttgtatg tgggattttc agctattgtt atttttaaa     5400 catttgtttt cattactaaa atatgcctat ttttcatttc tatttggctg gattcttttt    5460
aatactctag cagtaggttt atagtagcaa ctatattgtc tttcttgtgt ataggtaata    5520
taatttcttg tgttattttg atatgccaga tacactgata agtgctttat ttgtattagt    5580
ctcatttaat tttcacaatt accctaagaa actgctactc acatatgtta agcaacttgc    5640
ccaaaacgtc tgtgctagtg cttgctagtg agttgtaaaa cctgcactca aatcaaatct    5700
gtctctctgc cattatagcc cgtgttctta actaggacca gaaaatgctg gacaaatgct    5760
attgggcttt ggtgtaaaga aacgttgggg ttctgttta ctccaatttg tacttgtgta     5820 gcttttgaa accaccttt ttttctcac tagctgcaca gctgcgcctt atacatgtct       5880
agcgtgcacc tgccttagtg tctttgaact taaatttctc cctctggacc actgtttcat    5940
cagatgtcta tgcagcttgc cttggccctt ctttcagcca actttatcag agttcttccc    6000
tggccaccct attcaaaatt gcagctcttt gctacctatt gagttctagc cccttaccct    6060
gcttactttt ccatatagca cttaccatca cctgatataa tagatatttg catgtttgtc    6120
tattgtctgt ctccccccag tcagagtgta aactcagtga gagcagagac atcatttgtt    6180
ttgctcaagg ctagaaccag taactaaatg agtgctgagc acattctggt gctaataaat    6240
atttgcggga tgaattatag attttgtata aataaatgaa tagcctgggg acacagcccc    6300
acgaatctca ggggagtggt aaaagcacag ttcttccaag cagtcgagtg acttagcaat    6360
```

-continued

```
tactaagcat gggggtcacc tgcagcccct attctatgga tggaatttgt tttcttacat    6420
cctgttgatt cagactgttc acacattgcc caggtgtttg aggttcaagg aatctgcctc    6480
cttgttccag tccgtgcaga atacttccct ctagtggcca atgttgttgg catgtgcctc    6540
ttcagaggca atctcccata tcaaaaaaaa aaaaaaaat tcaccaacca agaaagccaa     6600
tgaaattctt attgaaaaca actgaaaaat gtttactgta aagcttatag cttgtggtag    6660
cggccttttt atctttatca aagaatctta gttggcttca atatcaagag agaaaatagg    6720
ctgggccatc ctcagaaatg acagctgtgt aagtgtagcc cttacacact tacctgctgg    6780
gtgtaaatta aatagaagac ctaggggatg tttgaaatga tataaatgag ccattcctct    6840
tgttagggga atcacaagaa caaactatat gactaagtag aaccaaggtg accttaacca    6900
tgggaaatgc ccggactctc aaggggagca ttgatcacct tggtttgatt gtcctgtgtt    6960
aacacagctg aggtcacctc cctgagaact aagaggatga actaaatgac cagattagat    7020
tttcaaggaa aatctaaaat aacactgagt tccttcctcc tggcccttca ctcacagtcc    7080
acagtgaccc cacgttctc tcccttgaga gacaaaatga ggcagatgga attcatgaag    7140
actgtcaaga tgctggatga gtttggtgta gaaggctttt gtcctacagg gagactgcat    7200
gtgtgttttgg tgcccgttta tagcaataac aacaagagct acccatctga tctgaggtcg    7260
ggcagcatgc tgagtgctta atgcacagta ccgcatttaa ccctcccctg ccaaaaccct    7320
gtgaggtggg caattgtcct cattttgcta atgagaacac tgaagctcag aaagtcactt    7380
gctttagaga attataacaa taataatgaa agcaataagg ctgttttta ctgcaggctt     7440
cttctgagcc aatactgagg tgtgatatt gcattcatga tttgatttaa ttctcacaag     7500
tcctgttgag ggcatgacat attttttact cctaataggg cagcacctta ttaatctttc    7560
agccaaattt gctaatgtca aaataatata tatgccttaa tttattgaac atattagaat    7620
tcttaaaacc cttcatcctt ctctattctc tactgatatt cttataattc tttattttga    7680
tataatttcc aatttatgga aaagtcctgg gaatagtaca agggacttcc atatgcccctt    7740
tgccctgatt taccaactgt ttacagtttt accccattta ttttatcatt atctctcccc    7800
catctcttac gtgtatctta atacttttc caaaaccttt gatggtaaat ttgagacata     7860
catcatgcct atttgcccct aagtacttca gtgagtattt tctaagaaca agagtattct    7920
cttctataac tgcaatacct ttatcaaagt tagaaaacaa acattgattg acattagtgt    7980
ttaattcgta gtctatatcc aaattttgtc aattgtccca aagtccttta cagctgtttt    8040
ccctcctctg gtccataatc taatccagga tcatttacta tacatttggc caccaagtct    8100
gtctccttca taaacaaaca attcctaagg ttttgtcttt ttgattttg catttttgaa     8160
gagttttgga cagggattta atttgcttta tctgatgttt cttcatggtg tgattcaagt    8220
tatatgtttt tggcaggaat aacccaaaag tgaagttata tctttcttgg ttcatcatat    8280
tatgaagcaa ataatgttgg cttgttccaa tactgataat aactttaatg acttcattaa    8340
ggtggtatct gccaggtttt tctaaagtta gtattttcc ttttgtaatt aacaaataag     8400
ttatgggaag ataatttcag gatatgtagt attctgtctt taaattttac tcactaattt    8460
taacattcac tgataatttc aatctttctg aatttgttag tgggtattgt actgtaaatc    8520
aatgttttgt atttactaat tggcattctg taaataagag cttttccttc caattattta    8580
tttgttcatt tatttattgg tctctatatg gacttgaaca ttcttaattt attcaatggg    8640
atataattat ttactataat tattttgatg ctcaatattt ctgtatttga acagtgggag    8700
ctccttcaag ctggcttgtg ggtccttttg acatgaaggt ctcttaatca ctaaaccatt    8760
```

```
atatatatgt ggtatacata taccttaata atcatactat accatctact ggggcactttt   8820 caatatttct gaagagccca gacaagtctg ataataatta cacaaaacaa agaacagaag   8880
ttaaacttta tagattcttt ttctgccggg caacatgcca tccatttctt gtgctctatt   8940
ttattaaagc ataacaaaaa tcttatttta ctgatgagga aatcaaggca cacaccaaag   9000
gtcaagtaat tggccaagat aactaagcta gcaagcagct gaatcaagat ctgaacacag   9060
gtttgtttga tttgaaagct cttattcatt actggacaac aagaaaggga gagaacattt   9120
catacagttg aaattttctc tttttgcagg ttccaggcct gtggtgttac tgcagcatgg   9180
cctagttgga ggtgctagca actggatttc caacctgccc aacaatagcc tgggcttcat   9240
tctggcagat gctggttttg acgtgtggat ggggaacagc aggggaaacg cctggtctcg   9300
aaaacacaag acactctcca tagaccaaga tgagttctgg gctttcaggt atatgataat   9360
ctcgagaaca gaggtagaca tgtctgtctt tcaaaaaaaa tgggtaaaaa attacggctt   9420
ctagtatttg gttgatttat tttggttgag tcatcattat cttaacatga tatcccccag   9480
ttttcttaat taactagtga ttccttggtt gaagtagtga ggaatgctga gttccccatg   9540
tagaaggtgg gtctagctaa tagggtgaga atggtggttg gtgtcaggtg actaagattg   9600
gaatgagaga agtgtagatc aatttcctca tggggagggg cgggtaatag tataatagta   9660
ctccagaagg aaaagagacc aggcagcatt aaaaaaaaag aaaggaaact attaagccta   9720
gtgtgttagt ccgttttcac actgctgtaa agaactgccc gagactaagt aatttataaa   9780
gtaaagggtt ttaatttact cacagttcag cggggctggg gaggcctcag gaaacttaca   9840
atcatggcag aaggtgaagg ggaagcaagg caccctttttc acaaggctgc agcaagaagt   9900
gctgagcaaa aggggaaga gcccttttata aaacaatcag atcttatgag aactcactat   9960
cacgagaaca gcacagggga aaccactccc atgattcaac tacctccacc tggtctctcc  10020
cttgacacat ggggattaca gggattatgg ggattacaat tcaagatgag atttgagtgg  10080
gaacacaagg cctaaccata tcacctaggg accatcgatt tgacttacct ctcatgttct  10140
tacaaaagat ttttaactct tttatttaaa ttacctattg atgttcaact cactttttat  10200
ggctatcaga gacggaccac ttcagcatct ttacaactat tcctgtaaat gaatctgcag  10260
agccctgtgc ggttctgctt aacagtagaa caggacactt ccactagcag ttgcgttatg  10320
tgctcagtaa atattcactg aagatagtta ttgctacgtg ataacatcta gagaaaacag  10380
cagtttgctg acagcctgtg actccagagg cacccatgct tcataggttt gaaagaaatc  10440
cattctgagt gttgtgaggg acacggtaac aagctgtcag agttgacaac tcaagggctt  10500
gtttgtaaac ctggtgtggg ggggagcttt tgtttgtttc tgattataat ttttcatata  10560
actttgtctt ttccccttgt agttatgatg agatggctag gtttgacctt cctgcagtga  10620
taaactttat tttgcagaaa acgggccagg aaaagatcta ttatgtcggc tattcacagg  10680
gcaccaccat gggtaggttc aaagaaaagc aggtttgtat actcggaaga aatgtgagca  10740
tacgacacta gctatccctg aaatctgtca ccttgtgctt ccttcagacc tgctcttttc  10800
atcttcagaa tcatgtagtc cccagcaatg tgtctagcat atagacatat gtgctagata  10860
tagcatatct ctgtgctata tgtgtctaga tatagcatat ctctcaatat aaatattttc  10920
tcaaagccaa catcgtgtta ttcaattatt tatttaactc attgagcacc tactacttga  10980
aagcaaatat gctggtgtca taaggacctt ataatttttat aggagaggta agatgcagtc  11040
acatatatac ttattgaaat atgtatttaa aagcaaaata tacattttat gagttctaaa  11100
```

```
aatatttcgt attcatgttg acatatttct tcttttgcag gctttattgc attttccacc    11160
atgccagagc tggctcagaa aatcaaaatg tattttgctt tagcacccat agccactgtt    11220
aagcatgcaa aaagccccgg gaccaaattt ttgttgctgc cagatatgat gatcaaggta    11280
tgagactcct cagaaaactt cctgtgtacg tagaaaaatc ttccagccca atttcctaaa    11340
acataaactt ttaaattaca gtcacatctt ttctgtctgt catgtctatg tcacttcata    11400
ttttcacagg gattgtttgg caaaaaagaa tttctgtatc agaccagatt tctcagacaa    11460
cttgttattt acctttgtgg ccaggtgatt cttgatcaga tttgtagtaa tatcatgtta    11520
cttctgggtg gattcaacac caacaatatg aacatggtaa gtgggagcct agtaaattcc    11580
cagcatccca gcataaagct gggagtcata tggctcaccc ctggagggag agctaatgcc    11640
agtgaagact cagagtaatg atatattctc agtaactcag ttctctgcaa actgtaagga    11700
aataagggaa atgcttcagt atggactgaa acaaggttaa cataagggca ttgctgatat    11760
taaatcacag attatagatg gaagaggtct gaaagcagct ttactacagt gaattaaatt    11820
aaaaagagca attagcacat gttagacaac agagacaact gtcatgcatc atccacctct    11880
accctgcact ggggtcctgt aggtttgtag tttaagttct ttgatggaac atcagggacc    11940
ttcattttgg cttaggctac cagttggtat cactgggtgg gttccctagg aagcatactc    12000
tgagatggag gttaatgtga acaatgattt gggtcctgct ctaggataa tacctagaga    12060
aggaaaagaa acaggactag gtaggtgaaa aagtcaagta gtgatgcagt ctcaatagga    12120
gacttagttg atcctgcagg gatttttgaa gataggatga cccttcagaa ccgtctcaag    12180
ttaggaagag agggttgggt ctttatacac catatcagtc agtcatttaa tgtagccata    12240
ccagtaacag ggtagcactg ggcaatgtat ctgcctacaa ttggtgcaat cctcaaagca    12300
gactgagagt ggagggctgt ttgccagcag cactcccagc agctggggca acatttcctt    12360
aattctgaat attttttctt cttctttaag attaataatt tgatttatag taaggatatg    12420
aaaagtatat attatgtatc aggctaattt attacctata ccaagcctat gagtgttatt    12480
aatatcccca ctttgcagat tagtatacta agatttagta gattaagtga ctcactcaaa    12540
ttcacctaaa aattaaactg cagaactagg atttgaatac aggcccaatg ctagagccct    12600
catcctaaat atcactagta aaattttttt taattagggg ccagatctct gatgagaacc    12660
tattctcaga tgaaaaatac cggtgtctgg caatacattt aatgacattt tatttacgtg    12720
catgtacata ttttttgtttc atagataatt gctgataact taataatgtt accatttctt    12780
agtctgacac cctggagatt tggtcttgac agggtataca tcttgtgagt ttttctatgt    12840
cccccagaat actcatggtt tgttacagag ccgagcaagt gtatatgctg cccacactct    12900
tgctggaaca tctgtgcaaa atattctaca ctggagccag gtaagaatgt tgaatttgca    12960
gtctttgcta aatgtcctgt tatattttgt gtagaatagt caaaggacac catttagata    13020
agccagggat tatttcacac ttattctaag atgaaatgca gtatcgtcga tgctattttg    13080
atggagaatt tgatctagat cactgaaact tttcaagaaa tgggaagaaa ggacagaagt    13140
agcctaagaa cttctttaga tcttaaaagt atgaatttag atgatccaag tgagacttct    13200
ctctgtctct agacacctca agatgtggc tggagataat tatgtttcta catcttctct    13260
tcagctcctc caacaataca gtcaagtaga aacaaaaatg ctaatgtggg gtctgtcaaa    13320
agagatattc acaggagtcc ttcacactgc aaactttacc tgcaattaca ggaaacacac    13380
acctctgtgt gtctatgtgg tgtgtgtgaa agagagggat gggggaagga gagagttctc    13440
tctgttgaca ggtagggaga gacagagaga gagagagcaa ttgtaccatc aaaaccagag    13500
```

-continued

```
aagaattata agttcaatta aattttggtt gctatcttcc aggatcacca cattgcacaa    13560
ttccagggca cgattcccca ttgtagccca cacagttgtg gaggatacccactcacatta    13620 attacaatga agatgcactt cctggagttg ctaatgcaat gatcaagaat ttatgtagtc    13680
cctctttctt ctcaaaaggc ctcattcttg tcttaccatt ttcctgagac gcttatccca    13740
acattgaatg gaagagcagc tcaaccattg ctctctcctt ccctcatgag tgcacactgg    13800
gtagcacatt tccaccaccc caccacgctt atccactgag acgttggaat tccttgtaaa    13860 ttttttgtctc cttttaggca gtgaattctg gtgaactccg ggcatttgac tggggagtg    13920 agaccaaaaa tctggaaaaa tgcaatcagg taagaaaatc aaataccatc tgctgaaaat    13980
atatacattg gaaatgtatg acagggacgt taatgaca gtttattcta gatatgggaa     14040
taaaatatga aaatttaagc agaaaataat ggttcatgtt tgactccatt tgaaaatggt    14100
taagttcaca gctgatccaa gaaacctctc tgcttttaca atggagtagg aggccttttt    14160
agctgaggct gtctccctaa acaaggtact gggcttctca ggagcaagat gaagtagatt    14220
tagtcaagag aagagtgtag tctatggtgg atactagaag gattatttta gaattaaaaa    14280
aaatgggatg gtggcagtaa gtttgtttca tggcacagta aaaggaacat taaatggcaa    14340
gtgaggattg ctgtgtaagt tttgcctctg cactataaac ttctgtaata ggagggaggc    14400
tgctttaatt tttcaggctt caatttcttt accttgaaaa taaaaatttt gggcttagaa    14460
aatccatagg cattctccct agttatactt taaatgaatc tgtaatttgc aagttacatt    14520
ttttaaaaat gttattacat tacccaagaa aatatgtagc taatgctatg aactaaaatt    14580
agatatcaaa gtgtggagat tcagaattgc acaggtatgc cctttagaac ataaaatctt    14640
ctgaagattt ttggtaatca tgtgtatgaa tgtaaataaa tatttaccat agaaacaata    14700
ctggaagggg cagattagac acagcttagt ctttctttga gaccctcaca tcataaatta    14760
acatccgctg ccatatgtct atctagatgt aaaatgctag gaaactggac aaactgtgca    14820
gtgcccctgg atagcgaact ctcaatctct ggtatcagct gcttctcttg aagtctttct    14880
tcactgtttc ccaaaatatg tctttagaga aagtatttct gttcaaagat gttttttttaa   14940 ttatatttat ttacttttga gacagaatct tgctctgtca cccaggctgg agtgcagtgg    15000
cgcagtctcg gctcactgaa aactctgcct cctagctttg agccattctc ttgcctcagc    15060
ctcccgagta gctgggacta caggtgcacg ccaccatgct cagctaattt tttttttgta    15120
cttttaggga tggggtttca ccatgttggt caggctggtc tcaaactcct gacctcaagt    15180
gatccaccta cctcagcctc ccaaagtgct gggattacag gcgtgagcca ctgtgcccgg    15240
ccctaagatg gctttaattt atcaacattt aatggactga gttctagaga aattgattca    15300
tgcagaatag gcaccagaaa atgggagtgg aagggaagag taaacaaaca cacaaaaaaa    15360
atcatagaat cacagaaact cagagcgaga tatgacattc agttcaatct tttcacctgt    15420
aagatgacaa aaaaaattac tagccccata gaattttca accttcctta tccaaattag    15480
gccataactg agccacaaag agaaaccaga gcatctagga ttggagccaa gactccatgg    15540
tggatttcct gagtaagaaa tgggccttac cacttctgag gaaagttctg gatgctgatt    15600
aatctcaagg gctcagccgg ctaggctaat tctactaaca ctgcataaat acggaaagtt    15660
cccaggtatt aggaatacta attggtatat ttggtgggga agggtgagga ataaggattg    15720
gagcaggtat ttaactttta cttccctta gctcaaatta cctgagtgcc ataggccatg    15780
gttctggcaa atgcagtcaa gccgggtctg cctcaaaggc tgcctgggat cacataaaga    15840
```

```
ctgtgaagat gcagagccct tcccagcaga ttccttgctt ttctctgtgg aatataattc    15900
ttctttcatg aaatgtttgt gaaattatct tttaaaagaa caggggcatt attttttaaaa   15960 acaatttgtt tacaaaatat ttaataggaa gaaaaaagaa atacaaggca ttacatgttt    16020
ttatgtgttt tgtcatttga tctagcaagt tattacagat attatcccca gtcacagaag    16080
aagaaactga ggttcaataa tgttaagtaa ttttaccttta aagtaagggc gggaacagaa    16140
attcttaaca gagttgtgtg gctctaacac ccatgtaccc ttcaccacaa cagatggcat    16200
gtttattatg tctatttgaa acataaatta tgagcctgaa agtccaaatg ttacctagag    16260
ttaagaacta ttccttttct ctagccaact cctgtaaggt acagagtcag agatatgacg    16320
gtccctacag caatgtggac aggaggtcag gactggcttt caaatccaga agacgtgaaa    16380
atgctgctct ctgaggtgac caacctcatc taccataaga atattcctga atgggctcat    16440
gtggatttca tctgggggttt ggatgctcct caccgtatgt acaatgaaat catccatctg   16500
atgcagcagg aggagaccaa cctttcccag ggacggtgtg aggccgtatt gtgaagcatc    16560
tgacactgac gatcttagga caacctcctg agggatgggg ctaggaccca tgaaggcaga    16620
attacggaga gcagagacct agtatacatt tttcagattc cctgcacttg gcactaaatc    16680
cgacacttac atttacatttt tttttctgta aattaaagta cttattaggt aaatagaggt    16740
tttgtatgct attatatatt ctaccatctt gaagggtagg ttttacctga tagccagaaa    16800
atatctagac attctctata tcattcaggt aaatctcttt aaaacaccta ttgttttttc    16860
tataagccat atttttggag cactaaagta aaatggcaaa ttgggacaga tattgaggtc    16920
tggagtctgt ggattattgt tgactttgac aaaataagct agacattttc accttgttgc    16980
cacagagaca taacactacc tcaggaagct gagctgcttt aaggacaaca acaacaaaat    17040
cagtgttaca gtatggatga aatctatgtt aagcattctc agaataaggc caagttttat    17100
agttgcatct cagggaagaa aattttatag gatgtttatg agttctccaa taaatgcatt    17160
ctgcattaca taaagcatgt atgtgcattt cagtgtctag attctagtcc aagcttgttg    17220
gaaggtttac agcttgttgc taggagacct aatgactaaa aatttctggc tcaatttttct   17280 gcctccaaaa attaaaagct agggagaaaa ttgcataatg tcatgagcat gatgaaacaa    17340
attgtcatat actttatcct ttaatcttga caaagttaat gtcagacagt ctctgcaact    17400
cattgacaaa ccatgattta tttcttcaga aaattattcc acttttacac aatttcaaag    17460
atgacagttg taaattacat tggtactatt ttgcaaaatc tctgaaacca aatcaaaggt    17520
ttgtgtgtgt caaaagtata ttgttgaagg tatactggtg tgtgaaattc acttgtgtgg    17580 gtttttttgtc cccaagggtc acctggtagc tcagctcaat gccagtgaat cttaatttat    17640
taagacacgt ttaaagactt cagaatctat atctacacac tattacttcc ttcataaaat    17700
aagtttctta aatcctgtac acagttgaat atatattgct ggatttgatt ttcattagag    17760
ctttcaagga tggtaaatct ttcattctta tactgtactt gttaccacat acaaagaggc    17820
tggcttagtt cctgtctgca gctatgtgag attcagtctt gattttcaaa attcagtcat    17880
atttttaaag tgaatttatt tctactctgt gtcattcaca gaagaagtga gacagatatt    17940
ttgatattcg caatctctca cttagacaaa taatccagat cctacctcat tgtatagctc    18000
tgtttctttt gaagaacttt atccaaataa gttacaataa tatttttacat ctatcaataa    18060 aataaacaaa actaacaagc ttggcaacca ccttgtatatt acaaaaggat catgaagatt    18120 ttttttaaacg aacattttca tagttgcata gtcttgctca aaccaagatg gcttttattt    18180
gtaaaccgaa atctctagtg gtatgctggt aaacgaactt tatggaaagt aaaaaacaaa    18240
```

```
aaaacaaaaa caaactctga tttgtcaatt tgccaatttc tgtggtgtaa acacactcac   18300
cgctgacact tgatagatgt ttttattgaa attccttcac caaaggaata tttacttgtg   18360
aatctctaag cccacacaca tacacaaata ccattctgta caaacatacg tatttaataa   18420
tttgattctt ctgctcaata ctcaaagggg gctgggagga acagtttgtc tcctagggca   18480
tgacatagac tggacagtct ttttataaga gtgatacaac tgggaaggga gaacgctgtt   18540
tcagaagata actc                                                    18554
```

<210> SEQ ID NO 4
<211> LENGTH: 374
<212> TYPE: PRT
<213> ORGANISM: Homo Sapiens

<400> SEQUENCE: 4

```
Ser Glu Ile Ile Gln His Gln Gly Tyr Pro Cys Glu Glu Tyr Glu Val
 1               5                  10                  15

Ala Thr Glu Asp Gly Tyr Ile Leu Ser Val Asn Arg Ile Pro Arg Gly
            20                  25                  30

Leu Val Gln Pro Lys Lys Thr Gly Ser Arg Pro Val Val Leu Leu Gln
        35                  40                  45

His Gly Leu Val Gly Gly Ala Ser Asn Trp Ile Ser Asn Leu Pro Asn
    50                  55                  60

Asn Ser Leu Gly Phe Ile Leu Ala Asp Ala Gly Phe Asp Val Trp Met
65                  70                  75                  80

Gly Asn Ser Arg Gly Asn Ala Trp Ser Arg Lys His Lys Thr Leu Ser
                85                  90                  95

Ile Asp Gln Asp Glu Phe Trp Ala Phe Ser Tyr Asp Glu Met Ala Arg
            100                 105                 110

Phe Asp Leu Pro Ala Val Ile Asn Phe Ile Leu Gln Lys Thr Gly Gln
        115                 120                 125

Glu Lys Ile Tyr Tyr Val Gly Tyr Ser Gln Gly Thr Thr Met Gly Phe
    130                 135                 140

Ile Ala Phe Ser Thr Met Pro Glu Leu Ala Gln Lys Ile Lys Met Tyr
145                 150                 155                 160

Phe Ala Leu Ala Pro Ile Ala Thr Val Lys His Ala Lys Ser Pro Gly
                165                 170                 175

Thr Lys Phe Leu Leu Leu Pro Asp Met Met Ile Lys Gly Leu Phe Gly
            180                 185                 190

Lys Lys Glu Phe Leu Tyr Gln Thr Arg Phe Leu Arg Gln Leu Val Ile
        195                 200                 205

Tyr Leu Cys Gly Gln Val Ile Leu Asp Gln Ile Cys Ser Asn Ile Met
    210                 215                 220

Leu Leu Leu Gly Gly Phe Asn Thr Asn Met Asn Met Ser Arg Ala
225                 230                 235                 240

Ser Val Tyr Ala Ala His Thr Leu Ala Gly Thr Ser Val Gln Asn Ile
                245                 250                 255

Leu His Trp Ser Gln Ala Val Asn Ser Gly Glu Leu Arg Ala Phe Asp
            260                 265                 270

Trp Gly Ser Glu Thr Lys Asn Leu Glu Lys Cys Asn Gln Pro Thr Pro
        275                 280                 285

Val Arg Tyr Arg Val Arg Asp Met Thr Val Pro Thr Ala Met Trp Thr
    290                 295                 300

Gly Gly Gln Asp Trp Leu Ser Asn Pro Glu Asp Val Lys Met Leu Leu
```

```
                305                 310                 315                 320
            Ser Glu Val Thr Asn Leu Ile Tyr His Lys Asn Ile Pro Glu Trp Ala
                            325                 330                 335
            His Val Asp Phe Ile Trp Gly Leu Asp Ala Pro His Arg Met Tyr Asn
                            340                 345                 350
            Glu Ile Ile His Leu Met Gln Gln Glu Glu Thr Asn Leu Ser Gln Gly
                    355                 360                 365
            Arg Cys Glu Ala Val Leu
                    370

<210> SEQ ID NO 5
<211> LENGTH: 601
<212> TYPE: DNA
<213> ORGANISM: Homo Sapiens
<220> FEATURE:
<221> NAME/KEY: variation
<222> LOCATION: (0)...(0)

<400> SEQUENCE: 5
ttgagagggt ggtagcaaaa aggtcagcac ataggacagc tggagcagct aagaacatgc        60
cagattcaag gagctgaaag cagcttatat ctggatggtc ttttaaacat tgactttttt       120
atactattac aaaagcaata tatgctcatt atagaaaatt taaaaaatac aaagaaggc        180 aatagtcacc aatgtactct gcaccaagaa ctgctttgtc atgcctttat cttcattcta       240
aatctgtgag gttttgtttt cttaagaaga aatgtcatgc acaatttact attttccaac       300 ktttttttctg ctaaacaatg tatatcatga agaatttccc aacgttttaa ataccttct       360 acaacatcat ttcaccttgc tgcattatgt tccatttttt taaataagta tttgccccag       420
gttggatttt ctgggggaca gactctgagg cagaattcat acaataatgt ttattaagga       480
gaatcatcat catcgcctgt ggaaggaag tagagaatca ggagtaagga aagagataaa        540
tcaaactgtg atacagactt caaaacagcc agactcaact ccatgaggag ctatgagct        600 a                                                                       601

<210> SEQ ID NO 6
<211> LENGTH: 601
<212> TYPE: DNA
<213> ORGANISM: Homo Sapiens

<400> SEQUENCE: 6
cattgacttt tttatactat tacaaaagca atatatgctc attatagaaa atttaaaaaa        60
tacaaaagaa ggcaatagtc accaatgtac tctgcaccaa gaactgcttt gtcatgcctt       120
tatcttcatt ctaaatctgt gaggttttgt tttcttaaga gaaatgtca tgcacaattt        180 actattttcc aacttttttt ctgctaaaca atgtatatca tgaagaattt cccaacgttt       240
taaataccct tctacaacat catttcacct tgctgcatta tgttccattt ttttaaataa       300
rtatttgccc caggttggat tttctggggg acagactctg aggcagaatt catacaataa       360
tgtttattaa ggagaatcat catcatcgcc tgtggaaagg aagtagagaa tcaggagtaa       420
ggaaagagat aaatcaaact gtgatacaga cttcaaaaca gccagactca actccatgag       480
gagctatgga gctaaaactg ctcttcagag atgtcctacg ttgggctgag atgaccaggc       540
ctttagaccg caaacaggtc agtcactgga tgtggcagga agggacgtga acttggagga       600
a                                                                       601

<210> SEQ ID NO 7
```

```
<211> LENGTH: 601
<212> TYPE: DNA
<213> ORGANISM: Homo Sapiens

<400> SEQUENCE: 7
tgtcatgcac aatttactat ttttccaactt tttttctgct aaacaatgta tatcatgaag      60
aatttcccaa cgttttaaat acccttctac aacatcattt caccttgctg cattatgttc     120
cattttttta aataagtatt tgccccaggt tggattttct gggggacaga ctctgaggca     180
gaattcatac aataatgttt attaaggaga atcatcatca tcgcctgtgg aaaggaagta     240
gagaatcagg agtaaggaaa gagataaatc aaactgtgat acagacttca aaacagccag     300
rctcaactcc atgaggagct atggagctaa aactgctctt cagagatgtc ctacgttggg     360
ctgagatgac caggccttta gaccgcaaac aggtcagtca ctggatgtgg caggaaggga     420
cgtgaacttg gaggaagtgg ctttctacag ctaaggccat tcctacagaa aatgacagcc     480
aagggtgatc tgttgacagc acttccagtg gatgggacca gtcctttatt gcctgcataa     540
attttcctgc caagtatagc atgttgacca tcttgccacc tgtagacaat gtttgcagca     600
t                                                                    601

<210> SEQ ID NO 8
<211> LENGTH: 601
<212> TYPE: DNA
<213> ORGANISM: Homo Sapiens

<400> SEQUENCE: 8
aatgtttatt aaggagaatc atcatcatcg cctgtggaaa ggaagtagag aatcaggagt      60
aaggaaagag ataaatcaaa ctgtgataca gacttcaaaa cagccagact caactccatg     120
aggagctatg agctaaaaac tgctcttcag agatgtccta cgttgggctg agatgaccag     180
gcctttagac cgcaaacagg tcagtcactg gatgtggcag gaagggacgt gaacttggag     240
gaagtggctt tctacagcta aggccattcc tacagaaaat gacagccaag gtgatctgtt     300
wgacagcact tccagtggat gggaccagtc ctttattgcc tgcataaatt ttcctgccaa     360
gtatagcatg ttgaccatct tgccacctgt agacaatgtt tgcagcattt gtagttcttt     420
ttcttctcag atgtccatgt ccctatccct acctccttgg ctcttttgag caacttctat     480
tcaatcctca aggcccagtt caaattcttc ctccataaga ccttgcctgt ccagccctgc     540
tcattttgct cctcctgctc agaattccct tgctccttcc ttcactctca tccttcatcc     600
c                                                                    601

<210> SEQ ID NO 9
<211> LENGTH: 601
<212> TYPE: DNA
<213> ORGANISM: Homo Sapiens

<400> SEQUENCE: 9
aactccatga ggagctatgg agctaaaact gctcttcaga gatgtcctac gttgggctga      60
gatgaccagg cctttagacc gcaaacaggt cagtcactgg atgtggcagg aagggacgtg     120
aacttggagg aagtggcttt ctacagctaa ggccattcct acagaaaatg acagccaagg     180
gtgatctgtt gacagcactt ccagtggatg ggaccagtcc tttattgcct gcataaattt     240
tcctgccaag tatagcatgt tgaccatctt gccacctgta gacaatgttt gcagcatttg     300
yagttctttt tcttctcaga tgtccatgtc cctatcccta cctccttggc tcttttgagc     360
aacttctatt caatcctcaa ggcccagttc aaattcttcc tccataagac cttgcctgtc     420
```

```
cagccctgct cattttgctc ctcctgctca gaattccttt gctccttcct tcactctcat    480
ccttcatccc tcatctgaca cattacacat atcctctcaa taactacttg tcagatgtcc    540
tccattctca tgtttttata tatatttatc tccccaaata gttgacaaca gtggttcctg    600
a                                                                    601
```

<210> SEQ ID NO 10
<211> LENGTH: 601
<212> TYPE: DNA
<213> ORGANISM: Homo Sapiens

<400> SEQUENCE: 10

```
ttgagatgga gtctcgctct gtcaccaggt tggagtgcag tggcgcgatc ttggctcact     60
gtaacctccg cctcccagat tcaagcaatt cctcttcctc agcctcccaa gtagctagga    120
ctataggcat gcaccaccac gcccggctaa tttttttat tattatttta gtagagatgg    180
tgtttcacca tgttggccag gatggtctcg atctcctgac cttgtgatcc acccacctca    240
acctcccaaa gtgctgggat tacaggtgtg agccactgtg cccggcctat acatttttt    300 vaggttaagt atacaatggt gtctcacaca catacatgca cacatataca ctgcattcca    360
taatattcgg ttaattgagt tttaattata gtggtagtta atgcttattg agttcctact    420
atgtgctggg aattacagtt agtgttatgt gtgcattatc tttttgcatt tattgcaaca    480
gtcccatgga gtatgaacca ttagaattcc taatttacag atgcatgaac tgaagcatag    540
gagcagttta actaaatttc tcaagattat acagctagtt tatgtaatag tgttagaacc    600
a                                                                    601
```

<210> SEQ ID NO 11
<211> LENGTH: 601
<212> TYPE: DNA
<213> ORGANISM: Homo Sapiens

<400> SEQUENCE: 11

```
tctgtcacca ggttggagtg cagtggcgcg atcttggctc actgtaacct ccgcctccca     60
gattcaagca attcctcttc ctcagcctcc aagtagcta ggactatagg catgcaccac    120
cacgcccggc taatttttt tattattatt ttagtagaga tggtgtttca ccatgttggc    180
caggatggtc tcgatctcct gaccttgtga tccacccacc tcaacctccc aaagtgctgg    240
gattacaggt gtgagccact gtgcccggcc tatacatttt tttaaggtta agtatacaat    300
kgtgtctcac acacatacat gcacacatat acactgcatt ccataatatt cggttaattg    360
agttttaatt atagtggtag ttaatgctta ttgagttcct actatgtgct gggaattaca    420
gttagtgtta tgtgtgcatt atcttttgc atttattgca acagtcccat ggagtatgaa    480
ccattagaat tcctaattta cagatgcatg aactgaagca taggagcagt ttaactaaat    540
ttctcaagat tatacagcta gtttatgtaa tagtgttaga accagtgtta aaactcaaac    600
a                                                                    601
```

<210> SEQ ID NO 12
<211> LENGTH: 601
<212> TYPE: DNA
<213> ORGANISM: Homo Sapiens

<400> SEQUENCE: 12

```
tgcagtggcg cgatcttggc tcactgtaac ctccgcctcc cagattcaag caattcctct     60
```

```
tcctcagcct cccaagtagc taggactata ggcatgcacc accacgcccg gctaattttt    120
tttattatta ttttagtaga gatggtgttt caccatgttg gccaggatgg tctcgatctc    180
ctgaccttgt gatccaccca cctcaacctc ccaaagtgct gggattacag gtgtgagcca    240
ctgtgcccgg cctatacatt tttttaaggt taagtataca atggtgtctc acacacatac    300
dtgcacacat atacactgca ttccataata ttcggttaat tgagttttaa ttatagtggt    360
agttaatgct tattgagttc ctactatgtg ctgggaatta cagttagtgt tatgtgtgca    420
ttatcttttt gcatttattg caacagtccc atggagtatg aaccattaga attcctaatt    480
tacagatgca tgaactgaag cataggagca gtttaactaa atttctcaag attatacagc    540
tagtttatgt aatagtgtta gaaccagtgt taaaactcaa acagtgggac ccaggagctt    600
t                                                                    601

<210> SEQ ID NO 13
<211> LENGTH: 601
<212> TYPE: DNA
<213> ORGANISM: Homo Sapiens

<400> SEQUENCE: 13
tgatccaccc acctcaacct cccaaagtgc tgggattaca ggtgtgagcc actgtgcccg     60
gcctatacat ttttttaagg ttaagtatac aatggtgtct cacacacata catgcacaca    120
tatacactgc attccataat attcggttaa ttgagttttta attatagtgg tagttaatgc    180
ttattgagtt cctactatgt gctgggaatt acagttagtg ttatgtgtgc attatctttt    240
tgcatttatt gcaacagtcc catggagtat gaaccattag aattcctaat ttacagatgc    300
rtgaactgaa gcataggagc agtttaacta aatttctcaa gattatacag ctagtttatg    360
taatagtgtt agaaccagtg ttaaaactca acagtgggga cccaggagct ttctcctaat    420
gactatgctt tgttttttgcc ctatattcta cctgggcatg tgatgtttgg ccttctctct    480
tgctcttttt taaagcagcc cctgatgcaa atggttctct ccttctctct gagtgataac    540
aatgggcaag aatagtgagg atgcttagaa gatatttgca gctacaaatt ttccaaagaa    600
t                                                                    601

<210> SEQ ID NO 14
<211> LENGTH: 601
<212> TYPE: DNA
<213> ORGANISM: Homo Sapiens

<400> SEQUENCE: 14
ctatacattt ttttaaggtt aagtatacaa tggtgtctca cacacataca tgcacacata    60
tacactgcat tccataatat tcggttaatt gagttttaat tatagtggta gttaatgctt    120
attgagttcc tactatgtgc tgggaattac agttagtgtt atgtgtgcat tatctttttg    180
catttattgc aacagtccca tggagtatga accattagaa ttcctaattt acagatgcat    240
gaactgaagc ataggagcag tttaactaaa tttctcaaga ttatacagct agtttatgta    300
wtagtgttag aaccagtgtt aaaactcaaa cagtgggacc caggagcttt ctcctaatga    360
ctatgctttg tttttgccct atattctacc tgggcatgtg atgtttggcc ttctctcttg    420
ctctttttta aagcagcccc tgatgcaaat ggttctctcc ttctctctga gtgataacaa    480
tgggcaagaa tagtgaggat gcttagaaga tatttgcagc tacaaatttt ccaaagaatg    540
tctacatgta actactgtat agagtaagga ttcttaacca ggggttcgta tgtaggcaac    600
a                                                                    601
```

<210> SEQ ID NO 15
<211> LENGTH: 601
<212> TYPE: DNA
<213> ORGANISM: Homo Sapiens

<400> SEQUENCE: 15

| ggttaagtat | acaatggtgt | ctcacacaca | tacatgcaca | catatacact | gcattccata | 60 |
| atattcggtt | aattgagttt | taattatagt | ggtagttaat | gcttattgag | ttcctactat | 120 |
| gtgctgggaa | ttacagttag | tgttatgtgt | gcattatctt | tttgcattta | ttgcaacagt | 180 |
| cccatggagt | atgaaccatt | agaattccta | atttacagat | gcatgaactg | aagcatagga | 240 |
| gcagtttaac | taaatttctc | aagattatac | agctagttta | tgtaatagtg | ttagaaccag | 300 |
| kgttaaaact | caaacagtgg | gacccaggag | ctttctccta | atgactatgc | tttgtttttg | 360 |
| ccctatattc | tacctgggca | tgtgatgttt | ggccttctct | cttgctcttt | tttaaagcag | 420 |
| cccctgatgc | aaatggttct | ctccttctct | ctgagtgata | acaatgggca | agaatagtga | 480 |
| ggatgcttag | aagatatttg | cagctacaaa | ttttccaaag | aatgtctaca | tgtaactact | 540 |
| gtatagagta | aggattctta | accaggggtt | cgtatgtagg | caacaagata | tctgaaactc | 600 |
| c | | | | | | 601 |

<210> SEQ ID NO 16
<211> LENGTH: 498
<212> TYPE: DNA
<213> ORGANISM: Homo Sapiens

<400> SEQUENCE: 16

| gatgcatgaa | ctgaagcata | ggagcagttt | aactaaattt | ctcaagatta | tacagctagt | 60 |
| ttatgtaata | gtgttagaac | cagtgttaaa | actcaaacag | tgggacccag | gagctttctc | 120 |
| ctaatgacta | tgctttgttt | tgccctata | ttctacctgg | gcatgtgatg | tttggccttc | 180 |
| tctcttgctc | ttttttaaag | cagccccctga | tgcaaatggt | tctctccttc | tctctgagtg | 240 |
| ataacaatgg | gcaagaatag | tgaggatgct | tagaagatat | ttgcagctac | aaattttcca | 300 |
| ragaatgtct | acatgtaact | actgtataga | gtaaggattc | ttaaccaggg | gttcgtatgt | 360 |
| aggcaacaag | atatctgaaa | ctcctgaaat | tgaatgcaaa | accatgtttt | tgtatccatt | 420 |
| gtatatccat | tttatagtt | ctcctcaaat | tcacagaggg | aactttaacc | tgaaaatgtt | 480 |
| aggaatcaat | gctcttga | | | | | 498 |

<210> SEQ ID NO 17
<211> LENGTH: 601
<212> TYPE: DNA
<213> ORGANISM: Homo Sapiens

<400> SEQUENCE: 17

| taaagagctt | gagacacaaa | ctgctgggcc | cagtcctctg | agttcctgat | tcagtaggtt | 60 |
| tggttggaat | ttgcatatct | aacagattag | tccaagtgat | gctgatgcct | ttgtcccaag | 120 |
| gcccatactt | tgagaaccat | aattctattc | cggtttccat | attaagacaa | agaaagtaag | 180 |
| gactagagag | ggttagcaga | ttttttctaag | gtaacatgat | tagctaggga | aaagcaagga | 240 |
| ctttcactgt | gttttacagc | atcaaggaat | ctactcttac | ttttggatca | ttgagaatat | 300 |
| rgccacagag | aactgaacct | aaaagaaatt | gtgcttttc | catagagtga | aatcatccaa | 360 |
| catcaaggct | atccctgtga | ggaatatgaa | gtcgcaactg | aagatgggta | tatccttct | 420 |

```
gttaacagga ttcctcgagg cctagtgcaa cctaagaaga caggtgtggg tcacccatg      480 tcaccgcaac acagcagtct tctctgcagt cacgatttcc ttgtgatttg aatgtagaag     540
agagcctggg ttcttagtgc agagtgaggt ccattgttca ggtcaaagga tggtgtcagt     600
t                                                                     601

<210> SEQ ID NO 18
<211> LENGTH: 601
<212> TYPE: DNA
<213> ORGANISM: Homo Sapiens

<400> SEQUENCE: 18
ctgccaccaa ttatctcaat taaacataca gtgtttgctt ttcaaaacac tccttcaaga      60
aaagttcatt tcttgactta ttttagcgct taacccattc cccaaaactc ctcctatgta     120
gacattctaa aatatttact gacaattcct tgaacagacc atatcaacct ctgattatga     180
agaattcaag cttctttatg gcacctggta cccgctcctg tatactctgt attcctcatc     240
taaagagcac ttaaaatatt taagatgttg cctagctttt tactaagggc ttttgaaaaa     300
ygaaagttct atacatacat tttatttat tttattttat tttattttat tttattttat     360
ttttgaggtg gagttttgca cttgttgccc aggctggagt gcagtggtag gatctcagct     420
caccgcaacc tccgcctcct gggttcaagc aattctcctg cttcagcctc ccaagtagct     480
gggattacag gcatacacca ccacacctgg ctaattttg tattttggt agagacagag       540 tttctccatg ttggtcaggc tggtcttgaa ctcccgacct caggtgatcc acccgcctcc     600
a                                                                     601

<210> SEQ ID NO 19
<211> LENGTH: 601
<212> TYPE: DNA
<213> ORGANISM: Homo Sapiens

<400> SEQUENCE: 19
tatgcctatt tttcatttct atttggctgg attctttta atactctagc agtaggttta       60
tagtagcaac tatattgtct ttcttgtgta taggtaatat aatttcttgt gttattttga     120
tatgccagat acactgataa gtgctttatt tgtattagtc tcatttaatt ttcacaatta     180
ccctaagaaa ctgctactca catatgttaa gcaacttgcc caaaacgtct gtgctagtgc     240
ttgctagtga gttgtaaaac ctgcactcaa atcaaatctg tctctctgcc attatagccc     300
rtgttcttaa ctaggaccag aaaatgctgg acaaatgcta ttgggctttg gtgtaaagaa     360
acgttggggt tctgttttac tccaatttgt acttgtgtag cttttttgaaa ccacttttt     420 ttttctcact agctgcacag ctgcgcctta tacatgtcta gcgtgcacct gccttagtgt     480
ctttgaactt aaatttctcc ctctggacca ctgtttcatc agatgtctat gcagcttgcc     540
ttggcccttc tttcagccaa ctttatcaga gttcttccct ggccacccta ttcaaaattg     600
c                                                                     601

<210> SEQ ID NO 20
<211> LENGTH: 601
<212> TYPE: DNA
<213> ORGANISM: Homo Sapiens

<400> SEQUENCE: 20
gcccgtgttc ttaactagga ccagaaaatg ctggacaaat gctattgggc tttggtgtaa      60
agaaacgttg gggttctgtt ttactccaat ttgtacttgt gtagcttttt gaaaccacct    120
```

-continued

```
tttttttct cactagctgc acagctgcgc cttatacatg tctagcgtgc acctgcctta    180
gtgtctttga acttaaattt ctccctctgg accactgttt catcagatgt ctatgcagct    240
tgccttggcc cttctttcag ccaactttat cagagttctt ccctggccac cctattcaaa    300
rttgcagctc tttgctacct attgagttct agcccettac cctgcttact tttccatata    360
gcacttacca tcacctgata taatagatat ttgcatgttt gtctattgtc tgtctccccc    420

cagtcagagt gtaaactcag tgagagcaga gacatcattt gttttgctca aggctagaac    480
cagtaactaa atgagtgctg agcacattct ggtgctaata aatatttgcg ggatgaatta    540
tagattttgt ataaataaat gaatagcctg gggacacagc cccacgaatc tcaggggagt    600
g                                                                    601
```

<210> SEQ ID NO 21
<211> LENGTH: 601
<212> TYPE: DNA
<213> ORGANISM: Homo Sapiens
<220> FEATURE:
<221> NAME/KEY: variation
<222> LOCATION: (301)...(301)
<223> OTHER INFORMATION: A may be either present or absent

<400> SEQUENCE: 21

```
tttgtataaa taaatgaata gcctggggac acagccccac gaatctcagg ggagtggtaa     60
aagcacagtt cttccaagca gtcgagtgac ttagcaatta ctaagcatgg gggtcacctg    120
cagcccctat tctatggatg gaatttgttt tcttacatcc tgttgattca gactgttcac    180
acattgccca ggtgtttgag gttcaaggaa tctgcctcct tgttccagtc cgtgcagaat    240
acttccctct agtggccaat gttgttggca tgtgcctctt cagaggcaat ctcccatatc    300
aaaaaaaaaa aaaaaaattc accaaccaag aaagccaatg aaattcttat tgaaaacaac    360
tgaaaaatgt ttactgtaaa gcttatagct tgtggtagcg gcctttttat ctttatcaaa    420
gaatcttagt tggcttcaat atcaagagag aaaataggct gggccatcct cagaaatgac    480
agctgtgtaa gtgtagccct tacacactta cctgctgggt gtaaattaaa tagaagacct    540
aggggatgtt tgaaatgata taaatgagcc attcctcttg ttaggggaat cacaagaaca    600
a                                                                    601
```

<210> SEQ ID NO 22
<211> LENGTH: 601
<212> TYPE: DNA
<213> ORGANISM: Homo Sapiens
<220> FEATURE:
<221> NAME/KEY: variation
<222> LOCATION: (301)...(301)
<223> OTHER INFORMATION: A may be either present or absent

<400> SEQUENCE: 22

```
aaatgaatag cctggggaca cagccccacg aatctcaggg gagtggtaaa agcacagttc     60
ttccaagcag tcgagtgact tagcaattac taagcatggg ggtcacctgc agcccctatt    120
ctatggatgg aatttgtttt cttacatcct gttgattcag actgttcaca cattgcccag    180
gtgtttgagg ttcaaggaat ctgcctcctt gttccagtcc gtgcagaata cttccctcta    240
gtggccaatg ttgttggcat gtgcctcttc agaggcaatc tcccatatca aaaaaaaaaa    300
aaaaaattca ccaaccaaga aagccaatga aattcttatt gaaaacaact gaaaaatgtt    360
tactgtaaag cttatagctt gtggtagcgg cctttttatc tttatcaaag aatcttagtt    420
```

```
ggcttcaata tcaagagaga aaataggctg ggccatcctc agaaatgaca gctgtgtaag    480
tgtagccctt acacacttac ctgctgggtg taaattaaat agaagaccta ggggatgttt    540
gaaatgatat aaatgagcca ttcctcttgt taggggaatc acaagaacaa actatatgac    600
t                                                                    601
```

<210> SEQ ID NO 23
<211> LENGTH: 601
<212> TYPE: DNA
<213> ORGANISM: Homo Sapiens

<400> SEQUENCE: 23

```
cacgaatctc aggggagtgg taaaagcaca gttcttccaa gcagtcgagt gacttagcaa     60
ttactaagca tgggggtcac ctgcagcccc tattctatgg atggaatttg ttttcttaca    120
tcctgttgat tcagactgtt cacacattgc ccaggtgttt gaggttcaag gaatctgcct    180
ccttgttcca gtccgtgcag aatacttccc tctagtggcc aatgttgttg gcatgtgcct    240
cttcagaggc aatctcccat atcaaaaaaa aaaaaaaaaa ttcaccaacc aagaaagcca    300
rtgaaattct tattgaaaac aactgaaaaa tgtttactgt aaagcttata gcttgtggta    360
gcggcctttt tatctttatc aaagaatctt agttggcttc aatatcaaga gagaaaatag    420
gctgggccat cctcagaaat gacagctgtg taagtgtagc ccttacacac ttacctgctg    480
ggtgtaaatt aaatagaaga cctaggggat gtttgaaatg atataaatga gccattcctc    540
ttgttagggg aatcacaaga acaaactata tgactaagta gaaccaaggt gaccttaacc    600
a                                                                    601
```

<210> SEQ ID NO 24
<211> LENGTH: 601
<212> TYPE: DNA
<213> ORGANISM: Homo Sapiens

<400> SEQUENCE: 24

```
cacttcagca tctttacaac tattcctgta aatgaatctg cagagccctg tgcggttctg     60
cttaacagta gaacaggaca cttccactag cagttgcgtt atgtgctcag taaatattca    120
ctgaagatag ttattgctac gtgataacat ctagagaaaa cagcagtttg ctgacagcct    180
gtgactccag aggcacccat gcttcatagg tttgaaagaa atccattctg agtgttgtga    240
gggacacggt aacaagctgt cagagttgac aactcaaggg cttgtttgta aacctggtgt    300 sgggggggagc ttttgtttgt ttctgattat aatttttcat ataactttgt cttttcccct    360
tgtagttatg atgagatggc taggtttgac cttcctgcag tgataaactt tattttgcag    420
aaaacgggcc aggaaaagat ctattatgtc ggctattcac agggcaccac catgggtagg    480
ttcaaagaaa agcaggtttg tatactcgga agaaatgtga gcatacgaca ctagctatcc    540
ctgaaatctg tcaccttgtg cttccttcag acctgctctt ttcatcttca gaatcatgta    600
g                                                                    601
```

<210> SEQ ID NO 25
<211> LENGTH: 601
<212> TYPE: DNA
<213> ORGANISM: Homo Sapiens

<400> SEQUENCE: 25

```
tataactttg tcttttcccc ttgtagttat gatgagatgg ctaggtttga ccttcctgca     60
gtgataaact tattttgca gaaaacgggc caggaaaaga tctattatgt cggctattca    120
```

```
caggcacca ccatgggtag gttcaaagaa aagcaggttt gtatactcgg aagaaatgtg      180
agcatacgac actagctatc cctgaaatct gtcaccttgt gcttccttca gacctgctct     240
tttcatcttc agaatcatgt agtccccagc aatgtgtcta gcatatagac atatgtgcta    300
satatagcat atctctgtgc tatatgtgtc tagatatagc atatctctca atataaatat    360
tttctcaaag ccaacatcgt gttattcaat tatttattta actcattgag cacctactac    420
ttgaaagcaa atatgctggt gtcataagga ccttataatt ttataggaga ggtaagatgc    480
agtcacatat atacttattg aaatatgtat ttaaaagcaa aatatacatt ttatgagttc    540
taaaaatatt tcgtattcat gttgacatat ttcttctttt gcaggcttta ttgcattttc    600
c                                                                    601

<210> SEQ ID NO 26
<211> LENGTH: 601
<212> TYPE: DNA
<213> ORGANISM: Homo Sapiens

<400> SEQUENCE: 26
aatcatgtag tccccagcaa tgtgtctagc atatagacat atgtgctaga tatagcatat     60
ctctgtgcta tatgtgtcta gatatagcat atctctcaat ataaatattt tctcaaagcc    120
aacatcgtgt tattcaatta tttatttaac tcattgagca cctactactt gaaagcaaat    180
atgctggtgt cataaggacc ttataatttt ataggagagg taagatgcag tcacatatat    240
acttattgaa atatgtattt aaaagcaaaa tatacatttt atgagttcta aaaatatttc    300
rtattcatgt tgacatattt cttcttttgc aggctttatt gcattttcca ccatgccaga    360
gctggctcag aaaatcaaaa tgtattttgc tttagcaccc atagccactg ttaagcatgc    420
aaaaagcccc gggaccaaat ttttgttgct gccagatatg atgatcaagg tatgagactc    480
ctcagaaaac ttcctgtgta cgtagaaaaa tcttccagcc caatttccta aaacataaac    540
ttttaaatta cagtcacatc ttttctgtct gtcatgtcta tgtcacttca tattttcaca    600
g                                                                    601

<210> SEQ ID NO 27
<211> LENGTH: 601
<212> TYPE: DNA
<213> ORGANISM: Homo Sapiens

<400> SEQUENCE: 27
gggtatacat cttgtgagtt tttctatgtc ccccagaata tcatggtttt gttacagagc      60
cgagcaagtg tatatgctgc ccacactctt gctggaacat ctgtgcaaaa tattctacac    120
tggagccagg taagaatgtt gaatttgcag tctttgctaa atgtcctgtt atattttgtg    180
tagaatagtc aaaggacacc atttagataa gccaggatt atttcacact tattctaaga    240
tgaaatgcag tatcgtcgat gctattttga tggagaattt gatctagatc actgaaactt    300
ytcaagaaat gggaagaaag gacagaagta gcctaagaac ttctttagat cttaaaagta    360
tgaatttaga tgatccaagt gagacttctc tctgtctcta gacacctcaa agatgtggct    420
ggagataatt atgtttctac atcttctctt cagctcctcc aacaatacag tcaagtagaa    480
acaaaaatgc taatgtgggg tctgtcaaaa gagatattca caggagtcct tcacactgca    540
aactttacct gcaattacag gaaacacaca cctctgtgtg tctatgtggt gtgtgtgaaa    600
g                                                                    601
```

<210> SEQ ID NO 28
<211> LENGTH: 601
<212> TYPE: DNA
<213> ORGANISM: Homo Sapiens

<400> SEQUENCE: 28

| | | | | | |
|---|---|---|---|---|---|
| tcaagggctc | agccggctag | gctaattcta | ctaacactgc | ataaatacgg | aaagttccca | 60 |
| ggtattagga | atactaattg | gtatatttgg | tggggaaggg | tgaggaataa | ggattggagc | 120 |
| aggtatttaa | cttttacttc | cctttagctc | aaattacctg | agtgccatag | gccatggttc | 180 |
| tggcaaatgc | agtcaagccg | gtctgcctc | aaaggctgcc | tgggatcaca | taaagactgt | 240 |
| gaagatgcag | agcccttccc | agcagattcc | ttgcttttct | ctgtggaata | taattcttct | 300 |
| ytcatgaaat | gtttgtgaaa | ttatctttta | aaagaacagg | ggcattattt | ttaaaaacaa | 360 |
| tttgtttaca | aaatatttaa | taggaagaaa | aaagaaatac | aaggcattac | atgttttat | 420 |
| gtgttttgtc | atttgatcta | gcaagttatt | acagatatta | tccccagtca | cagaagaaga | 480 |
| aactgaggtt | caataatgtt | aagtaatttt | accttaaagt | aagggcggga | acagaaattc | 540 |
| ttaacagagt | tgtgtggctc | taacacccat | gtacccttca | ccacaacaga | tggcatgttt | 600 |
| a | | | | | | 601 |

<210> SEQ ID NO 29
<211> LENGTH: 601
<212> TYPE: DNA
<213> ORGANISM: Homo Sapiens

<400> SEQUENCE: 29

| | | | | | |
|---|---|---|---|---|---|
| attaggaata | ctaattggta | tatttggtgg | ggaagggtga | ggaataagga | ttggagcagg | 60 |
| tatttaactt | ttacttccct | ttagctcaaa | ttacctgagt | gccataggcc | atggttctgg | 120 |
| caaatgcagt | caagccgggt | ctgcctcaaa | ggctgcctgg | gatcacataa | agactgtgaa | 180 |
| gatgcagagc | ccttcccagc | agattccttg | cttttctctg | tggaatataa | ttcttctttc | 240 |
| atgaaatgtt | tgtgaaatta | tcttttaaaa | gaacaggggc | attattttta | aaacaatttt | 300 |
| rtttacaaaa | tatttaatag | gaagaaaaaa | gaaatacaag | gcattacatg | ttttatgtg | 360 |
| ttttgtcatt | tgatctagca | agttattaca | gatattatcc | ccagtcacag | aagaaaac | 420 |
| tgaggttcaa | taatgttaag | taattttacc | ttaaagtaag | ggcgggaaca | gaaattctta | 480 |
| acagagttgt | gtggctctaa | cacccatgta | cccttcacca | acagatggc | atgtttatt | 540 |
| atgtctattt | gaaacataaa | ttatgagcct | gaaagtccaa | atgttaccta | gagttaagaa | 600 |
| c | | | | | | 601 |

<210> SEQ ID NO 30
<211> LENGTH: 601
<212> TYPE: DNA
<213> ORGANISM: Homo Sapiens

<400> SEQUENCE: 30

| | | | | | |
|---|---|---|---|---|---|
| tacagcaatg | tggacaggag | gtcaggactg | gctttcaaat | ccagaagacg | tgaaaatgct | 60 |
| gctctctgag | gtgaccaacc | tcatctacca | taagaatatt | cctgaatggg | ctcatgtgga | 120 |
| tttcatctgg | ggtttggatg | ctcctcaccg | tatgtacaat | gaaatcatcc | atctgatgca | 180 |
| gcaggaggag | accaaccttt | cccagggacg | gtgtgaggcc | gtattgtgaa | gcatctgaca | 240 |
| ctgacgatct | taggacaacc | tcctgaggga | tgggctagg | acccatgaag | gcagaattac | 300 |
| rgagagcaga | gacctagtat | acattttca | gattccctgc | acttggcact | aaatccgaca | 360 |

```
cttacattta catttttttt ctgtaaatta aagtacttat taggtaaata gaggttttgt      420
atgctattat atattctacc atcttgaagg gtaggtttta cctgatagcc agaaaatatc      480
tagacattct ctatatcatt caggtaaatc tctttaaaac acctattgtt ttttctataa      540
gccatatttt tggagcacta aagtaaaatg gcaaattggg acagatattg aggtctggag      600
t                                                                     601
```